US011345908B2

(12) United States Patent
Slovic et al.

(10) Patent No.: US 11,345,908 B2
(45) Date of Patent: May 31, 2022

(54) MODIFIED MICROORGANISMS COMPRISING AN OPTIMIZED SYSTEM FOR OLIGOSACCHARIDE UTILIZATION AND METHODS OF USING SAME

(71) Applicant: BRASKEM S.A., Camaçari (BR)

(72) Inventors: Avram Michael Slovic, Camaçari (BR); Daniel Johannes Koch, Camaçari (BR)

(73) Assignee: BRASKEM S.A., Camacari (BR)

( * ) Notice: Subject to any disclaimer, the term of this patent is extended or adjusted under 35 U.S.C. 154(b) by 0 days.

(21) Appl. No.: 15/327,616

(22) PCT Filed: May 29, 2015

(86) PCT No.: PCT/US2015/033286
§ 371 (c)(1),
(2) Date: Jan. 19, 2017

(87) PCT Pub. No.: WO2015/184327
PCT Pub. Date: Dec. 3, 2015

(65) Prior Publication Data

US 2017/0204394 A1 Jul. 20, 2017

Related U.S. Application Data

(60) Provisional application No. 62/005,603, filed on May 30, 2014.

(51) Int. Cl.

| | |
|---|---|
| ***C12N 9/90*** | (2006.01) |
| ***C12N 9/10*** | (2006.01) |
| ***C12N 9/12*** | (2006.01) |
| ***C12P 5/00*** | (2006.01) |
| ***C12P 7/06*** | (2006.01) |
| ***C12P 19/32*** | (2006.01) |

(52) U.S. Cl.
CPC ............. *C12N 9/90* (2013.01); *C12N 9/1048* (2013.01); *C12N 9/1051* (2013.01); *C12N 9/12* (2013.01); *C12P 5/007* (2013.01); *C12P 7/06* (2013.01); *C12P 19/32* (2013.01); *C12Y 204/01001* (2013.01); *C12Y 504/02002* (2013.01); *Y02E 50/10* (2013.01)

(58) Field of Classification Search
CPC .......... C12N 9/90; C12N 9/1048; C12N 9/12; C12Y 204/01001
See application file for complete search history.

(56) References Cited

U.S. PATENT DOCUMENTS

2006/0275319 A1 12/2006 Muller et al.

FOREIGN PATENT DOCUMENTS

WO WO 2012/109274 A1 8/2012
WO WO 2015/184327 A1 12/2015

OTHER PUBLICATIONS

I. González-Rodriguez et al. "Catabolism of Glucose and Lactose in *Bifidobacterium animalis* subsp. *lactis*, Studied by 13C Nuclear Magnetic Resonance", Applied and Environmental Microbiology 79+(24):7628-7638 (Year: 2013).*

S.J. Reid et al. "Sucrose Utilization in Bacteria: Genetic Organization and Regulation", Applied Microbiology and Biotechnology 67: 312-321 (Year: 2005).*

S. de Kok et al. "Energy coupling in *Saccharomyces cerevisiae*: selected opportunities for metabolic engineering", FEMS Yeast Research, 12: 387-397. (Year: 2012).*

H. Kawasaki et al. "Cloning and Expression in *Escherichia coli* of Sucrose Phosphorylase Gene from Leuconostoc mesenteroides No. 165", Biosci. Biotech. Biochem. 60 (2): 322-3241 (Year: 1996).*

A.S. Batista et al. "Sucrose Fermentation by *Saccharomyces cerevisiae* Lacking Hexose Transport", J Mol. Microbiol. Biotechnol. 8: 26-22 (Year: 2004).*

Extended European Search Report for European Application No. EP 15800180.0, dated Oct. 18, 2017, 8 pages.

Galazka, et al., "Cellodextrin Transport in Yeast for Improved Biofuel Production." Science (2010); 330 (6000): 84-86.

Ha, et al., "Engineered *Saccharomyces cerevisiae* capable of simultaneous cellobiose and xylose fermentation." PNAS (2011); 108(2): 504-509.

Helaszek and White, "Cellobiose uptake and metabolism by Ruminococcus flavefaciens." Appl. Environ. Microbiol. (1991); 57(1): 64-68.

Li, et al., "Overcoming glucose repression in mixed sugar fermentation by co-expressing a cellobiose transporter and a β-glucosidase in *Saccharomyces cerevisiae*." Molecular Biosystems (2010); 11(6): 2129-2132.

Strobel, et al., "Carbohydrate Transport by the Anaerobic Thermophile Clostridium thermocellum LQRI." Appl. Environ. Microbiol. Nov. 1995; 61(11): 4012-4015.

Boles et al., "A family of hexosephosphate mutases in *Saccharomyces cerevisiue*," Eur. J. Biochem. (1994) 220, 83-96.

Chaudhuri et al., "Protonophore- and pH-insensitive glucose and sucrose accumulation detected by FRET nanosensors in *Arabidopsis* root tips," The Plant Journal (2008) 56, 948-962.

(Continued)

*Primary Examiner* — Tekchand Saidha
(74) *Attorney, Agent, or Firm* — Morgan, Lewis & Bockius LLP

(57) ABSTRACT

The present disclosure generally relates to modified microorganisms comprising an optimized system for oligosaccharide utilization comprising one or more polynucleotides coding for one or more energy independent oligosaccharide transporters for transporting an oligosaccharide into the microorganism, one or more polynucleotides coding for enzymes that catalyze the conversion of the oligosaccharide into at least one phosphorylated saccharide, and one or more polynucleotides coding for enzymes that catalyze the conversion of the phosphorylated saccharide into an isomer of the phosphorylated saccharide that is utilized in one or more enzymatic pathways in the microorganism for the production of an organic molecule such as acetic acid, acrylic acid, 3-hydroxypropionic acid, lactic acid, etc. The present disclosure also generally relates to methods of using the optimized system for oligosaccharide utilization.

13 Claims, 4 Drawing Sheets

Specification includes a Sequence Listing.

(56) References Cited

OTHER PUBLICATIONS

Chen et al., "Sucrose efflux mediated by Sweet proteins as a key step for phloem transport," Science. Jan. 13, 2012; 335(6065):207-211.
Chen et al. "Sugar transporters for intercellular exchange and nutrition of pathogens," Nature. Nov. 25, 2010; 468(7323):527-532.
Goedl et al., "Recombinant sucrose phosphorylase from Leuconostoc mesenteroides: Characterization, kinetic studies of transglucosylation, and application of immobilised enzyme for production of α-d-glucose 1-phosphate," Journal of Biotechnology, Mar. 2007, vol. 129, Issue 1, pp. 77-86.
Mwesigye et al., "Transport of sucrose by *Saccharomyces cerevisiae*," Journal of Fermentation and Bioengineering, 1994, vol. 77, Issue 6, pp. 687-690.
Overvoorde et al., "A Soybean Sucrose Binding Protein Independently Mediates Nonsaturable Sucrose Uptake in Yeast," The Plant Cell, Feb. 1996, vol. 8, 271-280.
Pirovani et al., "A sucrose binding protein homologue from soybean exhibits GTP-binding activity that functions independently of sucrose transport activity," Eur. J. Biochem., (2002) 269, 3998-4008.
Riesmeier et al., "Isolation and characterization of a sucrose carrier cDNA from spinach by functional expression in yeast," The EMBO Journal, 1992, vol. 11, No. 13, pp. 4705-4713.
Stambuk et al., "Active a-glucoside transport in *Saccharomyces cerevisiae*," FEMS Microbiology Letters (1999) 170:105-110.
Xuan et al., "Functional role of oligomerization for bacterial and plant Sweet sugar transporter family," PNAS, Sep. 2013 110(39): E3685-E3694.
PCT/US2015/033286, International Search Report and Written Opinion dated Aug. 25, 2015, 11 pages.
PCT/US2015/033286, International Preliminary Reporton Patentability dated Dec. 6, 2016, 9 pages.
Zhou, Y., et al., "A suite of sucrose transporters expressed in coats of developing legume seeds includes novel pH-independent facilitators." Plant J. (2007); 49(4):750-764. Epub Jan. 23, 2007.

* cited by examiner

SEQUENCE LISTING

```
<160> NUMBER OF SEQ ID NOS: 79

<210> SEQ ID NO 1
<211> LENGTH: 511
<212> TYPE: PRT
<213> ORGANISM: Artificial sequence
<220> FEATURE:
<223> OTHER INFORMATION: Synthesized: PsSUF1 (Pisum sativum)

<400> SEQUENCE: 1

Met Asp Asn Pro Ser Thr Asn Glu Ser Ser Asn Ile Ser Ser Ile His
1               5                   10                  15

Leu Glu Ser Ala Ser Asn Arg Lys Pro Thr Pro Leu Ile Lys Met Ile
            20                  25                  30

Ala Val Ala Ser Ile Ala Ala Gly Ile Gln Phe Gly Trp Ala Leu Gln
        35                  40                  45

Leu Ser Leu Leu Thr Pro Tyr Ile Gln Leu Leu Gly Val Pro His Lys
    50                  55                  60

Trp Ala Ala Asn Ile Trp Leu Cys Gly Pro Ile Ser Gly Met Ile Ile
65                  70                  75                  80

Gln Pro Ile Val Gly Tyr Tyr Ser Asp Arg Asn Arg Ser Arg Phe Gly
                85                  90                  95

Arg Arg Arg Pro Phe Ile Phe Phe Gly Ala Ile Ala Val Ala Val Ala
            100                 105                 110

Val Phe Leu Ile Gly Phe Ala Ala Asp Ile Gly His Ser Phe Gly Asp
        115                 120                 125

Asp Leu Lys Lys Lys Thr Arg Pro Lys Ala Val Val Ile Phe Val Phe
    130                 135                 140

Gly Phe Trp Ile Leu Asp Val Ala Asn Asn Met Leu Gln Gly Pro Cys
145                 150                 155                 160

Arg Ala Phe Ile Gly Asp Leu Ala Ala Asp Asp His Arg Arg Met Arg
                165                 170                 175

Thr Gly Asn Ala Leu Phe Ser Phe Phe Met Thr Val Gly Asn Val Leu
            180                 185                 190

Gly Tyr Ala Ala Gly Ser Tyr Arg Lys Leu Phe Met Met Leu Pro Phe
        195                 200                 205

Thr Lys Thr Glu Ala Cys Asn Glu Phe Cys Ala Asn Leu Lys Thr Cys
    210                 215                 220

Phe Phe Ile Ala Ile Phe Leu Leu Ile Leu Leu Ser Thr Phe Ala Leu
225                 230                 235                 240

Leu Tyr Val Glu Asp Ile Pro Leu Pro Ser Ile Glu Ser Gln Ser Gln
                245                 250                 255

Thr Gln Thr Gln Thr Gln Ser Glu Pro Glu Gln Gln Val Ser Cys Phe
            260                 265                 270

Gly Glu Ile Leu Gly Ala Phe Asn Gly Leu Gln Lys Pro Met Trp Met
        275                 280                 285

Leu Met Leu Val Thr Ala Ile Asn Trp Ile Ala Trp Phe Pro Phe Phe
    290                 295                 300

Leu Phe Asp Thr Asp Trp Met Gly His Glu Val Tyr Gly Gly Asn Pro
305                 310                 315                 320
```

-continued

```
Gly Asp Asp Ala Tyr Asn Arg Gly Val Arg Ala Gly Ala Met Gly Leu
                325                 330                 335

Met Ile Asn Ala Val Val Leu Ala Leu Met Ser Leu Ala Val Glu Pro
            340                 345                 350

Leu Gly Arg Phe Val Gly Gly Ala Lys Arg Leu Trp Gly Ile Val Asn
        355                 360                 365

Ile Ile Leu Ala Val Gly Leu Ala Met Thr Ile Val Ile Thr Lys Ala
    370                 375                 380

Ala Gln His Glu Arg His Val Ser Asn Gly Asn Thr Pro Ser Ala Gly
385                 390                 395                 400

Ile Ser Ala Ala Ser Phe Ala Phe Phe Ala Leu Leu Gly Ile Pro Leu
                405                 410                 415

Ala Ile Asn Phe Ser Val Pro Phe Ala Leu Ala Ser Ile Tyr Ser Ser
            420                 425                 430

Ala Ser Gly Ala Gly Gln Gly Leu Ser Leu Gly Val Leu Asn Ile Ala
        435                 440                 445

Ile Val Val Pro Gln Met Ile Val Ser Ala Leu Ser Gly Pro Trp Asp
    450                 455                 460

Ser Leu Phe Gly Gly Gly Asn Leu Pro Ala Phe Val Val Gly Ile Gly
465                 470                 475                 480

Ala Ala Val Ile Ser Gly Val Leu Ala Ile Ile Ile Leu Pro Thr Pro
                485                 490                 495

Lys Ala Thr Asp Val Ala Lys Val Pro Ile Ala Gly Gly Phe His
            500                 505                 510


<210> SEQ ID NO 2
<211> LENGTH: 1536
<212> TYPE: DNA
<213> ORGANISM: Artificial sequence
<220> FEATURE:
<223> OTHER INFORMATION: Synthesized: PsSUF1 (Pisum sativum)

<400> SEQUENCE: 2

atggataatc cttccaccaa tgaaagttcc aacatttctt ctattcattt agagtctgct     60

tcaaaccgaa aaccaacccc tctcattaag atgatagcag ttgcttccat cgcagccggt    120

atccagtttg gttgggccct acagctatct ttgctaacac cgtacatcca gctgcttggc    180

gtcccacata aatgggcagc caatatctgg ctgtgcggcc caatttctgg catgatcatc    240

caaccgatcg tcggttacta cagtgatcgg aaccgttctc gtttcggtcg ccgccgtcca    300

ttcatcttct tcggcgccat tgccgtcgcg gtcgcagtct ttctcatcgg gttcgctgct    360

gatatcggtc actcattcgg cgacgatctc aagaagaaaa cacgacccaa agcggttgtc    420

atctttgtat ttggtttctg gatactcgac gtcgctaata acatgctcca aggaccatgt    480

cgtgccttca tcggggacct cgctgctgac gaccatagaa gaatgagaac cggtaatgct    540

ctgttctcat tcttcatgac agtaggtaat gtccttggtt atgccgcggg ctcttaccgt    600

aagctcttca tgatgctccc tttcacaaaa accgaagctt gcaacgagtt ttgcgcaaat    660

cttaaaactt gtttcttcat tgcaatattt ctccttatct tactttcaac cttcgctctt    720

ctttacgtag aagacatccc gttaccatca atagaatcac aatcgcagac gcaaacacag    780

acacagtcgg aaccagaaca acaggtttcg tgtttcggag agatactagg tgcattcaac    840

ggactacaaa aaccgatgtg gatgttaatg ttagtgacag ctataaactg gatagcttgg    900

ttcccatttt tcttgtttga cactgattgg atgggtcacg aagtgtacgg cggcaatccc    960

ggagacgatg cttacaaccg tggcgtccgt gccggagcaa tgggactcat gatcaatgct   1020
```

```
gttgtgcttg ctttaatgtc gttagcggtg gagccattag ggcgttttgt ggggggtgca   1080

aagagacttt gggggattgt gaatattatt cttgcagttg gacttgccat gactatagtc   1140

attaccaagg cagctcagca tgaacgccac gtcagcaatg gtaatacgcc ttcggctggt   1200

atttcggctg cctcgttcgc tttcttcgct ctcctgggaa tccctcttgc gattaatttc   1260

agtgtcccat ttgctttagc atctatttac tccagtgctt ctggggctgg acaaggttta   1320

tctttgggag ttctcaatat tgcaattgtg gttccacaaa tgatagtatc cgcattgagt   1380

ggaccatggg actctctgtt tggcggaggc aacttaccgg cgtttgtggt cggtatcggg   1440

gcggccgtca tcagtggtgt attagcaatt attattttac ctaccccaaa ggcaaccgat   1500

gtggccaagg ttccaattgc gggtggattt cattag                              1536
```

```
<210> SEQ ID NO 3
<211> LENGTH: 507
<212> TYPE: PRT
<213> ORGANISM: Artificial sequence
<220> FEATURE:
<223> OTHER INFORMATION: Synthesized: PsSUF (Pisum sativum)

<400> SEQUENCE: 3

Met Pro Asn Pro Asp Ser Ser Arg Gln Pro His Arg Ser Lys Thr Arg
1               5                   10                  15

Pro Ser Ser Ser Ser Val Arg Ser Lys Pro Arg Pro Lys Asp Arg Val
            20                  25                  30

Pro Leu Thr Lys Leu Leu Arg Val Ala Ser Val Ala Gly Gly Ile Gln
        35                  40                  45

Phe Gly Trp Ala Leu Gln Leu Ser Leu Leu Thr Pro Tyr Val Gln Gln
    50                  55                  60

Leu Gly Ile Pro His Ala Trp Ala Ser Ile Ile Trp Leu Cys Gly Pro
65                  70                  75                  80

Leu Ser Gly Leu Ile Val Gln Pro Leu Val Gly His Leu Ser Asp Arg
                85                  90                  95

Cys Thr Ser Arg Phe Gly Arg Arg Arg Pro Phe Ile Leu Gly Gly Ala
            100                 105                 110

Ile Ser Ile Ala Leu Ser Val Leu Ile Ile Gly His Ala Ala Asp Leu
        115                 120                 125

Gly Trp Lys Phe Gly Asp Thr Lys Glu His Arg Arg Ser Ala Val Ala
    130                 135                 140

Phe Phe Val Phe Gly Phe Trp Ile Leu Asp Val Ala Asn Asn Val Thr
145                 150                 155                 160

Gln Gly Pro Cys Arg Ala Leu Leu Gly Asp Leu Thr Gly Lys Asp His
                165                 170                 175

Arg Arg Thr Arg Val Ala Asn Ala Tyr Phe Ser Leu Phe Met Ala Ile
            180                 185                 190

Gly Asn Ile Leu Gly Tyr Ala Thr Gly Ser Tyr Ser Gly Trp Tyr Arg
        195                 200                 205

Val Phe Pro Phe Thr Leu Thr Pro Ala Cys Asn Ile Ser Cys Ala Asn
    210                 215                 220

Leu Lys Ser Ala Phe Phe Leu Asp Ile Val Phe Met Leu Ile Thr Thr
225                 230                 235                 240

Tyr Ile Ser Ile Thr Ser Ala Asn Glu Val Pro Leu Gly Ser Ser Gly
                245                 250                 255

Glu Pro Asp Ala Glu Ala Glu Gly Glu Ser Gly Gly Ser Ala Glu Glu
            260                 265                 270
```

-continued

Ala Phe Leu Trp Glu Leu Phe Gly Thr Phe Lys Tyr Phe Ser Lys Pro
275 280 285

Ile Trp Ile Val Leu Ser Val Thr Ala Leu Thr Trp Val Gly Trp Phe
290 295 300

Pro Phe Leu Leu Phe Asp Thr Asp Trp Met Gly Arg Glu Ile Tyr Gly
305 310 315 320

Gly Glu Pro Asn Glu Gly Thr Asn Tyr Asp Ser Gly Val Arg Met Gly
325 330 335

Ala Leu Gly Leu Leu Leu Asn Ser Val Val Leu Gly Val Thr Ser Leu
340 345 350

Leu Met Glu Lys Leu Cys Arg Lys Arg Gly Ala Gly Phe Val Trp Gly
355 360 365

Ile Ala Asn Ile Leu Met Ala Val Cys Phe Ile Ala Met Leu Val Leu
370 375 380

Thr Tyr Val Ala Asn Asp Ile Gly Tyr Leu Gly Lys Asp Leu Pro Pro
385 390 395 400

Thr Ser Ile Val Ile Ala Ala Leu Thr Ile Phe Thr Val Leu Gly Phe
405 410 415

Pro Leu Ala Ile Thr Tyr Ser Val Pro Tyr Ala Leu Ile Ser Thr His
420 425 430

Ile Gln Pro Leu Gly Leu Gly Gln Gly Leu Ser Met Gly Val Leu Asn
435 440 445

Leu Ala Ile Val Phe Pro Gln Met Ile Val Ser Leu Gly Ser Gly Pro
450 455 460

Arg Asp Gln Leu Phe Gly Gly Gly Asn Ser Pro Ala Phe Ala Val Ala
465 470 475 480

Ala Ile Ala Ala Leu Val Ser Gly Gly Ile Ala Val Phe Ala Ile Pro
485 490 495

Arg Thr Gly Ser Gln Lys Pro Arg Asn Pro Val
500 505

<210> SEQ ID NO 4
<211> LENGTH: 1524
<212> TYPE: DNA
<213> ORGANISM: Artificial sequence
<220> FEATURE:
<223> OTHER INFORMATION: Synthesized: PsSUF (Pisum sativum)

<400> SEQUENCE: 4
atgccgaatc ccgactcttc ccgtcaaccc caccgctcca aaactcgtcc ctcatcttca 60
tcggttcgat ccaagcctcg ccctaaagac agagttccgc tcaccaagct actccgagta 120
gcgtcagttg ccggtgggat tcagttcgga tgggctttgc agttatctct tctaacgccc 180
tatgttcagc agctcggaat cccgcatgcg tgggccagta ttatatggct ctgcggcccg 240
ctttcggggc ttatcgttca gccgttggtt ggccatttga gtgatcgctg caccagtcga 300
ttcggccgga ggagaccgtt tatcttaggc ggagctattt cgattgcttt gtctgttctc 360
atcattggtc acgctgcgga tttgggatgg aagtttggtg ataccaagga acatcggcgg 420
tccgccgtcg cctttttcgt gttcgggttt tggattttgg atgttgctaa taatgtcact 480
caaggtcctt gtagagcatt gctcggtgat ctcaccggta aggatcatcg aaggacacga 540
gtcgcaaatg cttatttttc cctatttatg gctatcggta acattcttgg atatgcaact 600
ggatcataca gtggttggta cagggtcttt cctttcacac ttacccctgc atgcaatatt 660
agttgtgcaa atctcaagtc tgctttcttt ctggacattg ttttcatgct catcaccacc 720

```
tatatcagta tcacgtcagc taatgaagtg cctcttgggt caagtgggga acccgatgct    780

gaagcagaag gggagtcagg tggtagtgcg gaagaagctt ttttatggga actatttggg    840

acattcaaat atttttcaaa gcctatatgg atagtattgt ctgttactgc tctaacatgg    900

gttggatggt tcccatttct tctattcgat actgattgga tgggccgaga aatttatggc    960

ggtgagccaa atgaaggcac taattatgat tccggagtta gaatgggggc acttggttta   1020

ttgcttaatt cagttgttct tggagtaaca tcattactca tggagaagct atgcaggaag   1080

cggggggctg ggtttgtgtg ggaatcgcaa aatatcctaa tggcagtctg ctttatagca   1140

atgcttgttt taacctatgt ggcaaatgac attggttatt taggaaaaga tctgccaccc   1200

actagcatcg tgatagctgc actgacaatc tttaccgttc tcgggtttcc attggcaatc   1260

acttacagtg ttccatatgc cttaatttcc acacatattc agccattggg gctcggccaa   1320

ggattgtcaa tgggagttct aaatcttgca atagtgttcc cacagatgat agtgtcctta   1380

ggaagtggac cacgggatca gttatttggc ggaggaaact ctccggcgtt tgctgtggca   1440

gctattgcag ctcttgtcag tggaggcata gctgtctttg ctattccccg aactggttct   1500

caaaagccta gaaacccagt atga                                          1524
```

<210> SEQ ID NO 5
<211> LENGTH: 509
<212> TYPE: PRT
<213> ORGANISM: Artificial sequence
<220> FEATURE:
<223> OTHER INFORMATION: Synthesized: PvSUF1 (Phaseolus vulgaris)

<400> SEQUENCE: 5

```
Met Glu Ala Pro Ser Pro Thr Lys Pro Ile Asp Pro Thr Lys Pro Ser
1               5                   10                  15

Ile Thr Thr Leu Ser Val Glu Gly Ser Gln Gly Glu Pro Ser Pro Leu
            20                  25                  30

Arg Lys Met Phe Ala Val Ala Ser Ile Ala Ala Gly Ile Gln Phe Gly
        35                  40                  45

Trp Ala Leu Gln Leu Ser Leu Leu Thr Pro Tyr Val Gln Leu Leu Gly
    50                  55                  60

Val Pro His Ala Ala Ala Ser Phe Ile Trp Leu Cys Gly Pro Ile Ser
65                  70                  75                  80

Gly Leu Val Val Gln Pro Ile Val Gly Tyr Tyr Ser Asp Arg Ser Thr
                85                  90                  95

Ser Arg Tyr Gly Arg Arg Arg Pro Phe Ile Leu Gly Gly Ala Val Ala
            100                 105                 110

Val Ala Ile Ala Val Phe Leu Ile Gly Tyr Ala Ala Asp Ile Gly Tyr
        115                 120                 125

Ser Ala Gly Asp Asp Ile Thr Lys Lys Thr Arg Pro Arg Ala Val Ala
    130                 135                 140

Val Phe Val Ile Gly Phe Trp Ile Leu Asp Val Ala Asn Asn Met Leu
145                 150                 155                 160

Gln Gly Pro Cys Arg Ala Phe Leu Ala Asp Leu Ala Ala Gly Asp Gln
                165                 170                 175

Arg Lys Thr Arg Ile Ala Asn Gly Phe Phe Ser Phe Phe Met Ala Val
            180                 185                 190

Gly Asn Val Leu Gly Tyr Ala Ala Gly Ser Phe Ser Gly Leu His Lys
        195                 200                 205

Ile Phe Pro Phe Thr Gln Thr Lys Ala Cys Asp Val Phe Cys Ala Asn
```

```
    210                 215                 220

Leu Lys Ser Cys Phe Phe Phe Ser Ile Leu Leu Leu Leu Phe Leu Ser
225                 230                 235                 240

Thr Val Ala Leu Ile Tyr Val Lys Asp Lys Pro Val Ala Ala Arg Ala
                245                 250                 255

Val Gln Glu Asp Ala Gln Pro Ser Cys Phe Phe Gln Leu Phe Gly Ala
            260                 265                 270

Leu Lys Glu Leu Lys Arg Pro Met Trp Met Leu Met Leu Val Thr Ala
        275                 280                 285

Val Asn Trp Ile Gly Trp Phe Pro Tyr Phe Leu Phe Asp Thr Asp Trp
    290                 295                 300

Met Gly Arg Glu Val Tyr Gly Gly Thr Ala Gly Glu Asp Ala Tyr Ala
305                 310                 315                 320

Glu Gly Val Arg Val Gly Ser Leu Gly Leu Met Ile Asn Ala Val Val
                325                 330                 335

Leu Gly Phe Met Ser Leu Ala Val Glu Pro Leu Asp Arg Met Val Gly
            340                 345                 350

Gly Val Lys Arg Leu Trp Gly Ile Val Asn Phe Ile Leu Ala Ile Gly
        355                 360                 365

Phe Gly Met Thr Val Val Ile Thr Lys Met Ala Glu His Gln Arg His
    370                 375                 380

Leu Asn Pro Ala Ala Val Gly His Pro Ser Asp Gly Val Lys Ile Gly
385                 390                 395                 400

Ser Met Val Phe Phe Ala Val Leu Gly Val Pro Leu Ala Ile Thr Phe
                405                 410                 415

Ser Val Pro Phe Ala Leu Ala Ser Ile Tyr Ser Ser Ala Ser Gly Ala
            420                 425                 430

Gly Gln Gly Leu Ser Leu Gly Val Leu Asn Leu Ala Ile Val Val Pro
        435                 440                 445

Gln Met Val Val Ser Ala Leu Ser Gly Pro Trp Asp Ala Leu Phe Gly
    450                 455                 460

Gly Gly Asn Leu Pro Ala Phe Met Val Gly Ala Ala Ala Ala Ala Leu
465                 470                 475                 480

Ser Ala Ile Met Ala Ile Val Leu Leu Pro Thr Pro Lys Pro Ala Asp
                485                 490                 495

Glu Ala Lys Ala Ala Ser Met Val Ala Gly Gly Phe His
            500                 505


<210> SEQ ID NO 6
<211> LENGTH: 1530
<212> TYPE: DNA
<213> ORGANISM: Artificial sequence
<220> FEATURE:
<223> OTHER INFORMATION: Synthesized: PvSUF1 (Phaseolus vulgaris)

<400> SEQUENCE: 6

atggaggcac catctccaac caaacccatt gacccaacaa agccttccat caccaccctt      60

agtgtggagg gcagccaggg cgagcccagc ccactccgaa aaatgtttgc tgtggcgtcc     120

atagccgctg gcatacaatt cggatgggct cttcagctct ctctgctcac cccttacgtt     180

cagctcttgg gagtcccaca cgccgcagcc tccttcatct ggctctgtgg ccccatctcc     240

ggacttgtgg tgcagcccat tgtgggctac tacagcgaca gaagcacttc tcgctacggt     300

cgcagacgcc cttttattct tggaggtgca gtggctgtgg ccatagctgt atttctcatc     360

ggttatgcag ccgatatagg atactcagct ggcgacgaca taaccaagaa aacccgtcct     420
```

```
cgggctgttg cggtgtttgt cataggattt tggatcctag atgttgccaa caacatgtta    480

caaggacctt gccgtgcctt tctagcagac ttagctgctg gggaccagcg aaaaacgaga    540

atagccaatg ggtttttctc gttcttcatg gccgtgggca acgtcttggg atacgcagca    600

gggtctttca gtggtctgca taagatcttt cccttcacgc agaccaaggc gtgcgatgtt    660

ttctgcgcaa acctcaaaag ctgtttcttt ttctcgatct tgttgctgct gttcttgtcc    720

acggtggctc tcatttacgt aaaggacaag cccgtggcgg cacgggcggt gcaagaggac    780

gcccagccct cgtgtttctt tcagctcttc ggggcgttga aggagctcaa aagacccatg    840

tggatgctca tgttggtgac agctgtcaac tggatcgggt ggttccccta cttcctcttc    900

gacaccgact ggatgggtcg cgaggtgtac ggcggaacgg cgggcgagga cgcgtacgcg    960

gagggggtgc gcgtggggtc gctgggactc atgataaacg ccgtcgtttt ggggttcatg   1020

tcgctggcgg ttgaaccctt ggaccgcatg gttgggggag tgaagaggct gtgggggatc   1080

gtgaacttca ttctcgcgat tggcttcgga atgaccgtgg tcataaccaa gatggcagag   1140

caccagcgcc acttgaaccc cgccgccgtg ggtcacccct ccgacggcgt caaaattggc   1200

tccatggttt tcttcgcggt tctcggagtt ccccttgcga ttactttcag tgttcctttt   1260

gctcttgcat caatatactc cagcgcttca ggagcagggc aaggtttatc attgggagtc   1320

ctcaatcttg caattgttgt accacagatg gtggtgtctg cactgagtgg tccttgggat   1380

gctttgtttg gtggtggcaa cttgccggct ttcatggtgg gggcagcggc ggccgccttg   1440

agcgccataa tggcgattgt cttgctgcca accccaaaac cagctgatga ggccaaggct   1500

gcaagcatgg ttgcaggggg ctttcactag                                    1530
```

<210> SEQ ID NO 7
<211> LENGTH: 511
<212> TYPE: PRT
<213> ORGANISM: Artificial sequence
<220> FEATURE:
<223> OTHER INFORMATION: Synthesized: LjSUT4 (Lotus japonicus)

<400> SEQUENCE: 7

```
Met Pro Gly Asp Pro Asp Asn Arg His His His His Pro Arg Ser Lys
1               5                   10                  15

Asn Arg Pro Ser Thr Ser Ser Ala Arg Pro Pro Pro Ser Arg Pro Pro
            20                  25                  30

Pro Ala Arg Val Pro Leu Arg Gln Leu Leu Arg Val Ala Ser Val Ala
        35                  40                  45

Ser Gly Ile Gln Phe Gly Trp Ala Leu Gln Leu Ser Leu Leu Thr Pro
    50                  55                  60

Tyr Val Gln Gln Leu Gly Ile Pro His Gln Trp Ala Ser Ile Ile Trp
65                  70                  75                  80

Leu Cys Gly Pro Val Ser Gly Leu Phe Val Gln Pro Leu Val Gly His
                85                  90                  95

Leu Ser Asp Lys Cys Thr Ser Arg Phe Gly Arg Arg Arg Pro Phe Ile
            100                 105                 110

Leu Ala Gly Ala Ala Ser Ile Val Val Ala Val Leu Ile Ile Gly Tyr
        115                 120                 125

Ala Ala Asp Ile Gly Trp Met Leu Gly Asp Thr Glu Ser Phe Arg Pro
    130                 135                 140

Ala Ala Ile Thr Val Phe Val Ile Gly Phe Trp Ile Leu Asp Val Ala
145                 150                 155                 160
```

-continued

```
Asn Asn Val Thr Gln Gly Pro Cys Arg Ala Leu Leu Ala Asp Leu Thr
                165                 170                 175

Ser Lys Asp Asn Arg Arg Thr Arg Val Ala Asn Ala Tyr Phe Ser Leu
            180                 185                 190

Phe Met Ala Ile Gly Asn Ile Leu Gly Tyr Ala Thr Gly Ala Tyr Ser
        195                 200                 205

Gly Trp Tyr Arg Ile Phe Thr Phe Thr Leu Ser Pro Ala Cys Thr Ile
    210                 215                 220

Ser Cys Ala Asn Leu Lys Ser Ala Phe Phe Leu Asp Val Ala Phe Ile
225                 230                 235                 240

Ala Val Thr Thr Tyr Val Ser Ile Thr Ala Ala His Glu Val Pro Leu
                245                 250                 255

Asn Ser Ser Gly Ala Ala His Ala Gly Glu Gly Ala Gly Glu Ser Gly
            260                 265                 270

Ser Thr Glu Glu Ala Phe Met Trp Glu Leu Phe Gly Thr Phe Lys Tyr
        275                 280                 285

Phe Ser Ser Thr Val Trp Ile Ile Leu Ser Val Thr Ala Leu Asn Trp
    290                 295                 300

Thr Gly Trp Phe Pro Phe Ile Leu Phe Asp Thr Asp Trp Met Gly Arg
305                 310                 315                 320

Glu Ile Tyr Gly Ala Asp Pro Asn Gly Gly Pro Asn Tyr Asp Ala Gly
                325                 330                 335

Val Arg Met Gly Ala Leu Gly Leu Met Leu Asn Ser Val Val Leu Gly
            340                 345                 350

Val Thr Ser Leu Leu Met Glu Lys Leu Cys Arg Lys Arg Gly Ala Gly
        355                 360                 365

Phe Val Trp Gly Ile Ser Asn Ile Leu Met Ala Val Cys Phe Leu Ala
    370                 375                 380

Met Leu Val Val Thr Tyr Val Ala Asn Thr Ile Gly Tyr Val Gly Lys
385                 390                 395                 400

Asp Leu Pro Pro Thr Gly Ile Val Ile Ala Ala Leu Ile Ile Phe Thr
                405                 410                 415

Ile Leu Gly Phe Pro Leu Ala Ile Thr Tyr Ser Val Pro Tyr Ala Leu
            420                 425                 430

Ile Ser Lys His Thr Glu Pro Leu Gly Leu Gly Gln Gly Leu Ser Met
        435                 440                 445

Gly Val Leu Asn Leu Ala Ile Val Ile Pro Gln Ile Val Val Ser Leu
    450                 455                 460

Gly Ser Gly Pro Trp Asp Gln Leu Phe Gly Gly Gly Asn Ser Ala Ala
465                 470                 475                 480

Phe Ala Val Gly Ala Val Ala Ala Ile Met Ser Gly Leu Leu Ala Val
                485                 490                 495

Leu Ala Ile Pro Arg Thr Gly Thr Gln Lys Pro Gln Ile Arg Val
            500                 505                 510
```

<210> SEQ ID NO 8
<211> LENGTH: 1536
<212> TYPE: DNA
<213> ORGANISM: Artificial sequence
<220> FEATURE:
<223> OTHER INFORMATION: Synthesized: LjSUT4 (Lotus japonicus)

<400> SEQUENCE: 8

```
atgccgggtg atccggataa ccgtcatcac caccatcccc ggtccaaaaa ccgaccatcc      60

acgtcatcgg ctcgaccacc accatcacga ccaccaccgg cgagggttcc gttacggcag     120
```

```
ttactccgtg tggcctcggt ggcgagcggt attcagttcg gctgggctct acagctctct    180

ctcttaaccc cttacgttca gcagctcggg atccctcacc aatgggcgag catcatctgg    240

ctctgcggcc ctgtctccgg cctcttcgtc cagccgctcg tcggccacct cagcgacaaa    300

tgcaccagcc gcttcggccg ccgccggccg ttcattctcg ccggcgccgc ctcgatcgtt    360

gttgccgttc tcattattgg ctacgccgcc gacatcgggt ggatgcttgg tgacaccgag    420

agcttccggc cggccgccat caccgtgttt gtcatcgggt tttggattct cgacgtcgct    480

aataacgtca ctcaaggtcc ttgcagagcc ttgcttgctg atcttactag caaggataat    540

cgaaggactc gtgtcgcaaa tgcttacttc tccttgttta tggccattgg taacattctt    600

ggctatgcga ctggagcata cagtggttgg tacaggattt ttactttcac actttcccct    660

gcatgcacta ttagttgtgc aaatctcaag tctgctttct ttctcgacgt tgctttcatt    720

gcggtcacga catatgtcag cattacggca gctcatgaag tgcctctaaa ctcaagtggg    780

gcagcccatg caggagaagg ggcaggggag tcaggtagca cggaagaagc tttcatgtgg    840

gaattatttg ggacatttaa atatttttca agcactgtat ggataatact gtccgtaact    900

gctctgaatt ggactgggtg gttcccgttt attctctttg atactgattg gatgggacga    960

gaaatttatg gtgctgatcc aaatggaggc cctaattatg atgctggagt tagaatggga   1020

gcacttgggt taatgcttaa ttcagttgtt cttggagtta catcattgct catggagaag   1080

ctatgtagga agcggggggc tggttttgtg tggggaatct caaatatctt aatggctgtt   1140

tgctttcttg caatgttagt tgtaacctat gtggcaaata ccattggcta tgtgggcaaa   1200

gatctaccac caactggcat tgtgattgct gcactgataa tctttaccat tcttgggttt   1260

ccattggcaa tcacttacag tgttccttat gccttaattt ccaagcatac tgaaccattg   1320

ggacttggcc aagggttatc gatgggtgtc ctgaatctgg caatagtgat cccacagata   1380

gtggtctccc tgggaagtgg accatgggat cagctatttg gtggaggaaa ctccgcagcc   1440

tttgctgtgg gagctgttgc agccattatg agcggactct tagctgtctt ggcaattccc   1500

cgaactggta cccaaaagcc tcaaatccgt gtatga                              1536
```

```
<210> SEQ ID NO 9
<211> LENGTH: 240
<212> TYPE: PRT
<213> ORGANISM: Artificial sequence
<220> FEATURE:
<223> OTHER INFORMATION: Synthesized: SIP1-1 (Arabidopsis thaliana)

<400> SEQUENCE: 9

Met Met Gly Val Leu Lys Ser Ala Ile Gly Asp Met Leu Met Thr Phe
1               5                   10                  15

Ser Trp Val Val Leu Ser Ala Thr Phe Gly Ile Gln Thr Ala Ala Ile
            20                  25                  30

Ile Ser Ala Gly Asp Phe Gln Ala Ile Thr Trp Ala Pro Leu Val Ile
        35                  40                  45

Leu Thr Ser Leu Ile Phe Val Tyr Val Ser Ile Phe Thr Val Ile Phe
    50                  55                  60

Gly Ser Ala Ser Phe Asn Pro Thr Gly Ser Ala Ala Phe Tyr Val Ala
65                  70                  75                  80

Gly Val Pro Gly Asp Thr Leu Phe Ser Leu Ala Ile Arg Leu Pro Ala
                85                  90                  95

Gln Ala Ile Gly Ala Ala Gly Gly Ala Leu Ala Ile Met Glu Phe Ile
            100                 105                 110
```

```
Pro Glu Lys Tyr Lys His Met Ile Gly Gly Pro Ser Leu Gln Val Asp
        115                 120                 125

Val His Thr Gly Ala Ile Ala Glu Thr Ile Leu Ser Phe Gly Ile Thr
    130                 135                 140

Phe Ala Val Leu Leu Ile Ile Leu Arg Gly Pro Arg Arg Leu Leu Ala
145                 150                 155                 160

Lys Thr Phe Leu Leu Ala Leu Ala Thr Ile Ser Phe Val Val Ala Gly
                165                 170                 175

Ser Lys Tyr Thr Gly Pro Ala Met Asn Pro Ala Ile Ala Phe Gly Trp
            180                 185                 190

Ala Tyr Met Tyr Ser Ser His Asn Thr Trp Asp His Ile Tyr Val Tyr
        195                 200                 205

Trp Ile Ser Ser Phe Val Gly Ala Leu Ser Ala Ala Leu Leu Phe Arg
    210                 215                 220

Ser Ile Phe Pro Pro Pro Arg Pro Gln Lys Lys Lys Gln Lys Lys Ala
225                 230                 235                 240
```

<210> SEQ ID NO 10
<211> LENGTH: 723
<212> TYPE: DNA
<213> ORGANISM: Artificial sequence
<220> FEATURE:
<223> OTHER INFORMATION: Synthesized: SIP1-1 (Arabidopsis thaliana)

<400> SEQUENCE: 10

```
atgatgggtg tgttgaagtc ggcgattggg gatatgttga tgaccttctc ttgggttgtc     60

ctctccgcta cctttggaat tcagacggcg gcgattatct ccgccggtga ttttcaggca    120

atcacttggg ctccgttggt gattttgacg tcgttgattt tcgtctacgt ctcgatcttc    180

accgttatct tcggtagcgc tagcttcaat cctaccggaa gcgctgcctt ttatgtcgcc    240

ggtgtccccg gagatactct tttctccttg gcgattagat tacctgctca ggcaattggt    300

gctgcaggag gtgcattggc gatcatggag ttcataccag agaaatacaa gcatatgatt    360

ggaggtcctt ctcttcaggt tgatgtgcac actggagcta ttgctgaaac gatcttaagt    420

tttggtatta cctttgcggt tttgctaatt atcctcaggg gtccacggag attgcttgct    480

aagacgttct tgcttgctct tgcaaccatc tcatttgttg tcgccggatc taaatacact    540

ggaccagcca tgaatcctgc cattgcgttt ggatgggcat acatgtacag ctcccacaac    600

acatgggacc atatctacgt ctactggatc agttctttcg taggagcatt atctgctgca    660

ttgcttttcc gttctatctt cccgccacct cggccccaga agaagaaaca aaagaaagcc    720

tga                                                                  723
```

<210> SEQ ID NO 11
<211> LENGTH: 243
<212> TYPE: PRT
<213> ORGANISM: Artificial sequence
<220> FEATURE:
<223> OTHER INFORMATION: Synthesized: SIP1-2 (Arabidopsis thaliana)

<400> SEQUENCE: 11

```
Met Ser Ala Val Lys Ser Ala Leu Gly Asp Met Val Ile Thr Phe Leu
1               5                   10                  15

Trp Val Ile Leu Ser Ala Thr Phe Gly Ile Gln Thr Ala Ala Ile Val
            20                  25                  30

Ser Ala Val Gly Phe His Gly Ile Thr Trp Ala Pro Leu Val Ile Ser
        35                  40                  45
```

-continued

```
Thr Leu Val Val Phe Val Ser Ile Ser Ile Phe Thr Val Ile Gly Asn
    50                  55                  60

Val Leu Gly Gly Ala Ser Phe Asn Pro Cys Gly Asn Ala Ala Phe Tyr
65                  70                  75                  80

Thr Ala Gly Val Ser Ser Asp Ser Leu Phe Ser Leu Ala Ile Arg Ser
                85                  90                  95

Pro Ala Gln Ala Ile Gly Ala Ala Gly Gly Ala Ile Thr Ile Met Glu
            100                 105                 110

Met Ile Pro Glu Lys Tyr Lys Thr Arg Ile Gly Gly Lys Pro Ser Leu
        115                 120                 125

Gln Phe Gly Ala His Asn Gly Ala Ile Ser Glu Val Val Leu Ser Phe
    130                 135                 140

Ser Val Thr Phe Leu Val Leu Leu Ile Ile Leu Arg Gly Pro Arg Lys
145                 150                 155                 160

Leu Leu Ala Lys Thr Phe Leu Leu Ala Leu Ala Thr Val Ser Val Phe
                165                 170                 175

Val Val Gly Ser Lys Phe Thr Arg Pro Phe Met Asn Pro Ala Ile Ala
            180                 185                 190

Phe Gly Trp Ala Tyr Ile Tyr Lys Ser His Asn Thr Trp Asp His Phe
        195                 200                 205

Tyr Val Tyr Trp Ile Ser Ser Tyr Thr Gly Ala Ile Leu Ser Ala Met
    210                 215                 220

Leu Phe Arg Ile Ile Phe Pro Ala Pro Pro Leu Val Gln Lys Lys Gln
225                 230                 235                 240

Lys Lys Ala
```

<210> SEQ ID NO 12
<211> LENGTH: 732
<212> TYPE: DNA
<213> ORGANISM: Artificial sequence
<220> FEATURE:
<223> OTHER INFORMATION: Synthesized: SIP1-2 (Arabidopsis thaliana)

<400> SEQUENCE: 12

```
atgagtgcgg taaaatcggc gttaggtgat atggtgataa ccttttgtg ggttattctc      60

tcggcgacgt ttgggataca gacggcggcg attgtttccg ccgtagggtt tcatggtatc     120

acttgggctc ctcttgtgat ctcaacgttg gttgtttttg tctccatctc gatttttacg     180

gttattggaa acgttcttgg tggtgctagc ttcaatcctt gtggaaacgc agcgttttat     240

accgccggtg tttccagtga ttctctcttc tccttggcca ttagatctcc tgctcaggca     300

attggtgcgg caggcggtgc gataacgatc atggagatga taccggaaaa gtataagact     360

aggattggag gaaagccttc attgcaattt ggtgcacaca atggagctat ttctgaagtg     420

gtcctaagtt ttagtgttac atttttggtt ttactaatta tcctaagagg tcctcgaaaa     480

ctgctcgcga aaacgttctt gctcgcactc gctaccgtat cggtgtttgt cgtaggttct     540

aaattcacta gaccattcat gaatcctgcc attgcgtttg ggtgggcata tatctacaag     600

tctcacaaca catgggacca tttttatgtg tattggatca gctcctacac cggagctatt     660

ttatctgcga tgctctttag aattatattt ccggctccac ctctggttca gaaaaaacag     720

aagaaagctt ga                                                        732
```

<210> SEQ ID NO 13
<211> LENGTH: 524
<212> TYPE: PRT

```
<213> ORGANISM: Artificial sequence
<220> FEATURE:
<223> OTHER INFORMATION: Synthesized: SBP1 (Glycine max)

<400> SEQUENCE: 13

Met Gly Met Arg Thr Lys Leu Ser Leu Ala Ile Phe Phe Phe Phe Leu
1               5                   10                  15

Leu Ala Leu Phe Ser Asn Leu Ala Phe Gly Lys Cys Lys Glu Thr Glu
            20                  25                  30

Val Glu Glu Glu Asp Pro Glu Leu Val Thr Cys Lys His Gln Cys Gln
        35                  40                  45

Gln Gln Gln Gln Tyr Thr Glu Gly Asp Lys Arg Val Cys Leu Gln Ser
    50                  55                  60

Cys Asp Arg Tyr His Arg Met Lys Gln Glu Arg Glu Lys Gln Ile Gln
65                  70                  75                  80

Glu Glu Thr Arg Glu Lys Lys Glu Glu Glu Ser Arg Glu Arg Glu Glu
                85                  90                  95

Glu Gln Gln Glu Gln His Glu Glu Gln Asp Glu Asn Pro Tyr Ile Phe
            100                 105                 110

Glu Glu Asp Lys Asp Phe Glu Thr Arg Val Glu Thr Glu Gly Gly Arg
        115                 120                 125

Ile Arg Val Leu Lys Lys Phe Thr Glu Lys Ser Lys Leu Leu Gln Gly
    130                 135                 140

Ile Glu Asn Phe Arg Leu Ala Ile Leu Glu Ala Arg Ala His Thr Phe
145                 150                 155                 160

Val Ser Pro Arg His Phe Asp Ser Glu Val Val Phe Phe Asn Ile Lys
                165                 170                 175

Gly Arg Ala Val Leu Gly Leu Val Ser Glu Ser Glu Thr Glu Lys Ile
            180                 185                 190

Thr Leu Glu Pro Gly Asp Met Ile His Ile Pro Ala Gly Thr Pro Leu
        195                 200                 205

Tyr Ile Val Asn Arg Asp Glu Asn Asp Lys Leu Phe Leu Ala Met Leu
    210                 215                 220

His Ile Pro Val Ser Val Ser Thr Pro Gly Lys Phe Glu Glu Phe Phe
225                 230                 235                 240

Ala Pro Gly Gly Arg Asp Pro Glu Ser Val Leu Ser Ala Phe Ser Trp
                245                 250                 255

Asn Val Leu Gln Ala Ala Leu Gln Thr Pro Lys Gly Lys Leu Glu Asn
            260                 265                 270

Val Phe Asp Gln Gln Asn Glu Gly Ser Ile Phe Arg Ile Ser Arg Glu
        275                 280                 285

Gln Val Arg Ala Leu Ala Pro Thr Lys Lys Ser Ser Trp Trp Pro Phe
    290                 295                 300

Gly Gly Glu Ser Lys Pro Gln Phe Asn Ile Phe Ser Lys Arg Pro Thr
305                 310                 315                 320

Ile Ser Asn Gly Tyr Gly Arg Leu Thr Glu Val Gly Pro Asp Asp Asp
                325                 330                 335

Glu Lys Ser Trp Leu Gln Arg Leu Asn Leu Met Leu Thr Phe Thr Asn
            340                 345                 350

Ile Thr Gln Arg Ser Met Ser Thr Ile His Tyr Asn Ser His Ala Thr
        355                 360                 365

Lys Ile Ala Leu Val Ile Asp Gly Arg Gly His Leu Gln Ile Ser Cys
    370                 375                 380

Pro His Met Ser Ser Arg Ser Ser His Ser Lys His Asp Lys Ser Ser
```

-continued

```
385                 390                 395                 400

Pro Ser Tyr His Arg Ile Ser Ser Asp Leu Lys Pro Gly Met Val Phe
                405                 410                 415

Val Val Pro Pro Gly His Pro Phe Val Thr Ile Ala Ser Asn Lys Glu
            420                 425                 430

Asn Leu Leu Met Ile Cys Phe Glu Val Asn Ala Arg Asp Asn Lys Lys
        435                 440                 445

Phe Thr Phe Ala Gly Lys Asp Asn Ile Val Ser Ser Leu Asp Asn Val
    450                 455                 460

Ala Lys Glu Leu Ala Phe Asn Tyr Pro Ser Glu Met Val Asn Gly Val
465                 470                 475                 480

Phe Leu Leu Gln Arg Phe Leu Glu Arg Lys Leu Ile Gly Arg Leu Tyr
                485                 490                 495

His Leu Pro His Lys Asp Arg Lys Glu Ser Phe Phe Phe Pro Phe Glu
            500                 505                 510

Leu Pro Arg Glu Glu Arg Gly Arg Arg Ala Asp Ala
        515                 520
```

<210> SEQ ID NO 14
<211> LENGTH: 1575
<212> TYPE: DNA
<213> ORGANISM: Artificial sequence
<220> FEATURE:
<223> OTHER INFORMATION: Synthesized: SBP1 (Glycine max)

<400> SEQUENCE: 14

```
atgggcatga gaaccaaact ttctttagct atctttttct tttttctttt agccttattt     60

tcaaacctag cctttggcaa atgtaaagaa accgaggtag aagaagaaga ccctgagctc    120

gtaacttgca aacaccaatg ccaacagcaa cagcaataca ctgagggtga caagcgggta    180

tgcttgcaaa gttgtgacag gtatcatcgt atgaagcaag agcgagagaa acaaatccaa    240

gaggaaactc gtgagaagaa agaggaggaa agccgtgaaa gggaagaaga acaacaagag    300

cagcatgagg aacaagatga aaatccctac atttttgagg aagataagga ttttgagacc    360

agagtcgaaa ctgaaggtgg cagaattcgg gttctcaaga agttcactga aaaatccaag    420

cttcttcagg gcattgagaa cttccgtttg gccattttgg aagctagagc acacacgttc    480

gtgtctcctc gccactttga ttccgaggtt gttttttca acatcaaggg gcgagccgta     540

cttgggttgg tgagtgaaag tgaaacagaa aaaatcaccc ttgaacctgg ggacatgata    600

cacataccag ctggcacccc actgtacatc gttaacagag atgagaatga taagctcttc    660

cttgccatgc tccatatacc tgtctctgtc tctactcctg gaaaatttga ggaatttttc    720

gcgcctggag gacgagaccc agaatcggtc ctctcagcat tcagctggaa tgtgctgcaa    780

gctgcgctcc aaaccccaaa aggaaagtta gaaaacgttt ttgatcaaca gaacgaggga    840

agtattttcc gaataagcag agaacaggtg cgtgcgttgg cccctaccaa gaaaagctct    900

tggtggccat tcggtggcga atccaagcct caattcaata ttttcagcaa gcgtcccact    960

atctccaacg gatatggtcg tttaactgaa gttggtcctg acgatgatga aaagagttgg   1020

cttcaaagac tcaatctcat gcttaccttt accaacatca cccagagatc tatgagtact   1080

attcactaca actcacatgc aacgaagata gcactggtga tcgatggcag agggcatctt   1140

caaatatcat gtccacacat gtcatcaagg tcgtcacact cgaagcatga taagagtagc   1200

ccttcatacc atagaatcag ttccgatttg aagcctggaa tggtgtttgt tgtccctccc   1260

ggtcatccct tcgtcaccat agcttccaat aaagagaatc tcctcatgat ttgcttcgag   1320
```

gttaacgctc gagacaacaa gaagtttaca tttgcaggga aggacaacat tgtgagttct 1380
ctggacaacg ttgctaagga gcttgccttt aactatcctt ctgagatggt gaacggagta 1440
ttcctgttgc aacgattcct cgaacggaaa ttgataggaa gactctacca cttgcctcat 1500
aaggaccgaa aggagagttt ctttttccct tttgagttgc cgagagagga gcgtggtcgt 1560
cgcgctgatg cgtga 1575

<210> SEQ ID NO 15
<211> LENGTH: 489
<212> TYPE: PRT
<213> ORGANISM: Artificial sequence
<220> FEATURE:
<223> OTHER INFORMATION: Synthesized: SBP2 (Glycine max)

<400> SEQUENCE: 15

Met Ala Thr Arg Ala Lys Leu Ser Leu Ala Ile Phe Leu Phe Phe Leu
1 5 10 15

Leu Ala Leu Ile Ser Asn Leu Ala Leu Gly Lys Leu Lys Glu Thr Glu
20 25 30

Val Glu Glu Asp Pro Glu Leu Val Thr Cys Lys His Gln Cys Gln Gln
35 40 45

Gln Arg Gln Tyr Thr Glu Ser Asp Lys Arg Thr Cys Leu Gln Gln Cys
50 55 60

Asp Ser Met Lys Gln Glu Arg Glu Lys Gln Val Glu Glu Glu Thr Arg
65 70 75 80

Glu Lys Glu Glu Glu His Gln Glu Gln His Glu Glu Glu Glu Asp Glu
85 90 95

Asn Pro Tyr Val Phe Glu Glu Asp Lys Asp Phe Ser Thr Arg Val Glu
100 105 110

Thr Glu Gly Gly Ser Ile Arg Val Leu Lys Lys Phe Thr Glu Lys Ser
115 120 125

Lys Leu Leu Gln Gly Ile Glu Asn Phe Arg Leu Ala Ile Leu Glu Ala
130 135 140

Arg Ala His Thr Phe Val Ser Pro Arg His Phe Asp Ser Glu Val Val
145 150 155 160

Leu Phe Asn Ile Lys Gly Arg Ala Val Leu Gly Leu Val Arg Glu Ser
165 170 175

Glu Thr Glu Lys Ile Thr Leu Glu Pro Gly Asp Met Ile His Ile Pro
180 185 190

Ala Gly Thr Pro Leu Tyr Ile Val Asn Arg Asp Glu Asn Glu Lys Leu
195 200 205

Leu Leu Ala Met Leu His Ile Pro Val Ser Thr Pro Gly Lys Phe Glu
210 215 220

Glu Phe Phe Gly Pro Gly Gly Arg Asp Pro Glu Ser Val Leu Ser Ala
225 230 235 240

Phe Ser Trp Asn Val Leu Gln Ala Ala Leu Gln Thr Pro Lys Gly Lys
245 250 255

Leu Glu Arg Leu Phe Asn Gln Gln Asn Glu Gly Ser Ile Phe Lys Ile
260 265 270

Ser Arg Glu Arg Val Arg Ala Leu Ala Pro Thr Lys Lys Ser Ser Trp
275 280 285

Trp Pro Phe Gly Gly Glu Ser Lys Ala Gln Phe Asn Ile Phe Ser Lys
290 295 300

Arg Pro Thr Phe Ser Asn Gly Tyr Gly Arg Leu Thr Glu Val Gly Pro

-continued

```
305                 310                 315                 320

Asp Asp Glu Lys Ser Trp Leu Gln Arg Leu Asn Leu Met Leu Thr Phe
                325                 330                 335

Thr Asn Ile Thr Gln Arg Ser Met Ser Thr Ile His Tyr Asn Ser His
            340                 345                 350

Ala Thr Lys Ile Ala Leu Val Met Asp Gly Arg Gly His Leu Gln Ile
        355                 360                 365

Ser Cys Pro His Met Ser Ser Arg Ser Asp Ser Lys His Asp Lys Ser
    370                 375                 380

Ser Pro Ser Tyr His Arg Ile Ser Ala Asp Leu Lys Pro Gly Met Val
385                 390                 395                 400

Phe Val Val Pro Pro Gly His Pro Phe Val Thr Ile Ala Ser Asn Lys
                405                 410                 415

Glu Asn Leu Leu Ile Ile Cys Phe Glu Val Asn Val Arg Asp Asn Lys
            420                 425                 430

Lys Phe Thr Phe Ala Gly Lys Asp Asn Ile Val Ser Ser Leu Asp Asn
        435                 440                 445

Val Ala Lys Glu Leu Ala Phe Asn Tyr Pro Ser Glu Met Val Asn Gly
    450                 455                 460

Val Ser Glu Arg Lys Glu Ser Leu Phe Phe Pro Phe Glu Leu Pro Ser
465                 470                 475                 480

Glu Glu Arg Gly Arg Arg Ala Val Ala
                485
```

<210> SEQ ID NO 16
<211> LENGTH: 1470
<212> TYPE: DNA
<213> ORGANISM: Artificial sequence
<220> FEATURE:
<223> OTHER INFORMATION: Synthesized: SBP2 (Glycine max)

<400> SEQUENCE: 16

```
atggcgacca gagccaagct ttctttagct atcttccttt tctttctttt agccttgatt      60

tcaaacctag ccttgggcaa acttaaagaa accgaggtcg aagaagatcc cgagctcgta     120

acatgcaaac accagtgcca acagcaacgg caatacactg agagtgacaa gcgaacatgc     180

ttgcaacaat gtgacagtat gaagcaagag cgagagaaac aagtcgaaga ggaaactcgc     240

gagaaggaag aagaacatca agagcagcat gaggaggagg aagacgaaaa tccctacgtt     300

tttgaagaag ataaggattt ttcgaccaga gtcgaaacag aaggtggcag cattcgggtt     360

ctcaagaagt tcactgagaa atccaagctt cttcaaggca ttgagaattt ccgtttggcc     420

atcttagaag ctagagcaca cacgttcgtg tccccacgcc actttgattc cgaggttgtc     480

ttgttcaaca ttaaggggag agccgtactt gggttggtga gggaaagtga aacagaaaaa     540

atcaccctag aacctggaga catgatacac ataccagcag gcacaccact gtacatcgtt     600

aacagagatg agaatgagaa gctcctcctt gccatgctcc atatacctgt ctctactcct     660

ggaaaatttg aggaattttt cgggcctgga ggacgagacc cagaatcggt cctctcagca     720

ttcagctgga atgtgctgca agctgcgctc caaaccccaa aaggaaagtt agaaaggctt     780

tttaatcaac agaacgaggg aagtattttc aaaataagca gagaacgggt gcgtgcgttg     840

gcccccacca agaaaagctc ttggtggcca ttcggcggcg aatccaaggc tcaattcaat     900

attttcagca agcgtcccac tttctccaac ggatatggcc gtttaactga agttggtcct     960

gatgatgaaa agagttggct tcaaagactc aacctcatgc ttacctttac caacatcacc    1020
```

```
cagagatcta tgagtactat tcactacaac tcacatgcaa cgaagatagc actggtgatg   1080

gatggtagag ggcatcttca aatatcatgt ccacacatgt catcaaggtc agactcaaag   1140

catgataaga gtagcccctc ataccataga atcagtgcgg acttgaagcc tggaatggtg   1200

tttgttgtcc ctcctggtca tcccttcgtc actatagctt ccaataaaga gaatctcctc   1260

ataatttgct tcgaggttaa cgttcgagac aacaagaagt ttacgtttgc agggaaggac   1320

aacattgtga gctctctgga caacgtagct aaggagctgg cctttaacta tccttctgag   1380

atggtgaacg gagtctccga aagaaaggag agtctctttt tccccttcga gttgccgagc   1440

gaggagcgtg gtcgtcgcgc tgttgcgtga                                    1470
```

<210> SEQ ID NO 17
<211> LENGTH: 289
<212> TYPE: PRT
<213> ORGANISM: Artificial sequence
<220> FEATURE:
<223> OTHER INFORMATION: Synthesized: AtSWEET10 (Arabidopsis thaliana)

<400> SEQUENCE: 17

```
Met Ala Ile Ser Gln Ala Val Leu Ala Thr Val Phe Gly Ile Leu Gly
1               5                   10                  15

Asn Ile Ile Ser Phe Phe Val Cys Leu Ala Pro Ile Pro Thr Phe Val
            20                  25                  30

Arg Ile Tyr Lys Arg Lys Ser Ser Glu Gly Tyr Gln Ser Ile Pro Tyr
        35                  40                  45

Val Ile Ser Leu Phe Ser Ala Met Leu Trp Met Tyr Tyr Ala Met Ile
    50                  55                  60

Lys Lys Asp Ala Met Met Leu Ile Thr Ile Asn Ser Phe Ala Phe Val
65                  70                  75                  80

Val Gln Ile Val Tyr Ile Ser Leu Phe Phe Phe Tyr Ala Pro Lys Lys
                85                  90                  95

Glu Lys Thr Leu Thr Val Lys Phe Val Leu Phe Val Asp Val Leu Gly
            100                 105                 110

Phe Gly Ala Ile Phe Val Leu Thr Tyr Phe Ile Ile His Ala Asn Lys
        115                 120                 125

Arg Val Gln Val Leu Gly Tyr Ile Cys Met Val Phe Ala Leu Ser Val
    130                 135                 140

Phe Val Ala Pro Leu Gly Ile Ile Arg Lys Val Ile Lys Thr Lys Ser
145                 150                 155                 160

Ala Glu Phe Met Pro Phe Gly Leu Ser Phe Phe Leu Thr Leu Ser Ala
                165                 170                 175

Val Met Trp Phe Phe Tyr Gly Leu Leu Leu Lys Asp Met Asn Ile Ala
            180                 185                 190

Leu Pro Asn Val Leu Gly Phe Ile Phe Gly Val Leu Gln Met Ile Leu
        195                 200                 205

Phe Leu Ile Tyr Lys Lys Pro Gly Thr Lys Val Leu Glu Pro Pro Gly
    210                 215                 220

Ile Lys Leu Gln Asp Ile Ser Glu His Val Val Asp Val Val Arg Leu
225                 230                 235                 240

Ser Thr Met Val Cys Asn Ser Gln Met Arg Thr Leu Val Pro Gln Asp
                245                 250                 255

Ser Ala Asp Met Glu Ala Thr Ile Asp Ile Asp Glu Lys Ile Lys Gly
            260                 265                 270

Asp Ile Glu Lys Asn Lys Asp Glu Lys Glu Val Phe Leu Ile Ser Lys
        275                 280                 285
```

Asn

<210> SEQ ID NO 18
<211> LENGTH: 870
<212> TYPE: DNA
<213> ORGANISM: Artificial sequence
<220> FEATURE:
<223> OTHER INFORMATION: Synthesized: AtSWEET10 (Arabidopsis thaliana)

<400> SEQUENCE: 18
atggcaattt cacaagccgt cttggctact gtctttggca tcctagggaa tatcatctcc 60
tttttcgtct gccttgcccc aataccgacg ttcgttcgta tatacaagag gaagtcatct 120
gaagggtatc agtcgatccc ttacgtgatt tctctgttca gcgcgatgct atggatgtac 180
tacgcaatga tcaagaaaga tgctatgatg ttgatcacta tcaactcctt tgcctttgtc 240
gtacaaatcg tctacatctc cttattcttc ttctacgctc ctaagaagga aaagactcta 300
acggtgaagt tcgtcctctt tgtggatgtt ttgggtttcg gcgcaatctt cgtgttgaca 360
tactttataa ttcatgccaa taaacgtgtt caagttcttg gatacatttg tatggtcttt 420
gctctatctg tttttgttgc tccccttggc ataattagga aagtgatcaa aacgaagagc 480
gccgagttca tgccattcgg tctctccttc ttcctcacct tatcggctgt catgtggttt 540
ttctacggac ttctccttaa agacatgaac attgccctgc caaatgtttt gggtttcatc 600
tttggagtac ttcagatgat tcttttcttg atctacaaga aaccagggac taaagtcttg 660
gagccaccag ggattaagct tcaggacata tctgagcatg tagtcgatgt tgtgaggcta 720
agtacgatgg tttgcaactc acagatgaga actttggtgc cacaagacag tgccgatatg 780
gaagcaacca ttgatataga tgagaagatc aaaggagata ttgagaagaa taaggatgaa 840
aaagaagtat ttctcatttc taagaattaa 870

<210> SEQ ID NO 19
<211> LENGTH: 289
<212> TYPE: PRT
<213> ORGANISM: Artificial sequence
<220> FEATURE:
<223> OTHER INFORMATION: Synthesized: AtSWEET11 (Arabidopsis thaliana)

<400> SEQUENCE: 19

Met Ser Leu Phe Asn Thr Glu Asn Thr Trp Ala Phe Val Phe Gly Leu
1               5                   10                  15

Leu Gly Asn Leu Ile Ser Phe Ala Val Phe Leu Ser Pro Val Pro Thr
            20                  25                  30

Phe Tyr Arg Ile Trp Lys Lys Lys Thr Thr Glu Gly Phe Gln Ser Ile
        35                  40                  45

Pro Tyr Val Val Ala Leu Phe Ser Ala Thr Leu Trp Leu Tyr Tyr Ala
    50                  55                  60

Thr Gln Lys Lys Asp Val Phe Leu Leu Val Thr Ile Asn Ala Phe Gly
65                  70                  75                  80

Cys Phe Ile Glu Thr Ile Tyr Ile Ser Met Phe Leu Ala Tyr Ala Pro
                85                  90                  95

Lys Pro Ala Arg Met Leu Thr Val Lys Met Leu Leu Leu Met Asn Phe
            100                 105                 110

Gly Gly Phe Cys Ala Ile Leu Leu Leu Cys Gln Phe Leu Val Lys Gly
        115                 120                 125

Ala Thr Arg Ala Lys Ile Ile Gly Gly Ile Cys Val Gly Phe Ser Val
    130                 135                 140

```
Cys Val Phe Ala Ala Pro Leu Ser Ile Ile Arg Thr Val Ile Lys Thr
145                 150                 155                 160

Arg Ser Val Glu Tyr Met Pro Phe Ser Leu Ser Leu Thr Leu Thr Ile
                165                 170                 175

Ser Ala Val Ile Trp Leu Leu Tyr Gly Leu Ala Leu Lys Asp Ile Tyr
            180                 185                 190

Val Ala Phe Pro Asn Val Leu Gly Phe Ala Leu Gly Ala Leu Gln Met
        195                 200                 205

Ile Leu Tyr Val Val Tyr Lys Tyr Cys Lys Thr Ser Pro His Leu Gly
    210                 215                 220

Glu Lys Glu Val Glu Ala Ala Lys Leu Pro Glu Val Ser Leu Asp Met
225                 230                 235                 240

Leu Lys Leu Gly Thr Val Ser Ser Pro Glu Pro Ile Ser Val Val Arg
                245                 250                 255

Gln Ala Asn Lys Cys Thr Cys Gly Asn Asp Arg Arg Ala Glu Ile Glu
            260                 265                 270

Asp Gly Gln Thr Pro Lys His Gly Lys Gln Ser Ser Ser Ala Ala Ala
        275                 280                 285

Thr
```

<210> SEQ ID NO 20
<211> LENGTH: 870
<212> TYPE: DNA
<213> ORGANISM: Artificial sequence
<220> FEATURE:
<223> OTHER INFORMATION: Synthesized: AtSWEET11 (Arabidopsis thaliana)

<400> SEQUENCE: 20

```
atgagtctct tcaacactga aaacacatgg gcctttgtct ttggcttgct cggcaacctt      60

atctcctttg ccgtgttcct atctcctgtg ccaacgttct ataggatttg gaagaagaag     120

acaacagaag ggtttcagtc tattccttat gttgtggcgc tcttcagtgc gacgctttgg     180

ctttactatg cgacacagaa gaaagatgtc ttcctcctcg taaccattaa cgcctttggt     240

tgcttcatcg aaaccatcta catctctatg ttccttgcct acgctcccaa gccagctcgg     300

atgttgacag tgaagatgct acttcttatg aactttggag gattctgtgc gattctcctt     360

ctttgccaat tcttggtaaa aggagccaca cgtgctaaga ttatcggagg aatctgtgtc     420

ggattctctg tttgtgtttt cgctgctcct ctaagcataa tcaggacggt aataaagaca     480

agaagtgtgg agtacatgcc ctttagctta tccttaaccc ttaccatcag tgctgtcata     540

tggctccttt atggtcttgc tctcaaggac atctatgttg ctttcccgaa tgtgcttggt     600

tttgctctcg gtgcactcca aatgatactc tacgttgtct acaaatactg taaaacgtcg     660

ccgcatctag gagagaaaga agtcgaagct gctaagttac cggaggtgag cctcgatatg     720

ttgaagctag gcacagtttc atcccctgag ccaatctcag tggttcgtca agcgaacaag     780

tgtacctgcg gaaatgatcg aagggctgag attgaagatg gacaaacccc taaacatggc     840

aagcagtcct cttccgcagc agctacatga                                      870
```

<210> SEQ ID NO 21
<211> LENGTH: 285
<212> TYPE: PRT
<213> ORGANISM: Artificial sequence
<220> FEATURE:
<223> OTHER INFORMATION: Synthesized: AtSWEET12 (Arabidopsis thaliana)

<400> SEQUENCE: 21

-continued

```
Met Ala Leu Phe Asp Thr His Asn Thr Trp Ala Phe Val Phe Gly Leu
1               5                   10                  15

Leu Gly Asn Leu Ile Ser Phe Ala Val Phe Leu Ser Pro Val Pro Thr
            20                  25                  30

Phe Tyr Arg Ile Cys Lys Lys Lys Thr Thr Glu Gly Phe Gln Ser Ile
        35                  40                  45

Pro Tyr Val Val Ala Leu Phe Ser Ala Met Leu Trp Leu Tyr Tyr Ala
    50                  55                  60

Thr Gln Lys Lys Asp Val Phe Leu Leu Val Thr Ile Asn Ser Phe Gly
65                  70                  75                  80

Cys Phe Ile Glu Thr Ile Tyr Ile Ser Ile Phe Val Ala Phe Ala Ser
                85                  90                  95

Lys Lys Ala Arg Met Leu Thr Val Lys Leu Leu Leu Leu Met Asn Phe
            100                 105                 110

Gly Gly Phe Cys Leu Ile Leu Leu Leu Cys Gln Phe Leu Ala Lys Gly
        115                 120                 125

Thr Thr Arg Ala Lys Ile Ile Gly Gly Ile Cys Val Gly Phe Ser Val
    130                 135                 140

Cys Val Phe Ala Ala Pro Leu Ser Ile Ile Arg Thr Val Ile Lys Thr
145                 150                 155                 160

Lys Ser Val Glu Tyr Met Pro Phe Ser Leu Ser Leu Thr Leu Thr Ile
                165                 170                 175

Ser Ala Val Ile Trp Leu Leu Tyr Gly Leu Ala Leu Lys Asp Ile Tyr
            180                 185                 190

Val Ala Phe Pro Asn Val Ile Gly Phe Val Leu Gly Ala Leu Gln Met
        195                 200                 205

Ile Leu Tyr Val Val Tyr Lys Tyr Cys Lys Thr Pro Ser Asp Leu Val
    210                 215                 220

Glu Lys Glu Leu Glu Ala Ala Lys Leu Pro Glu Val Ser Ile Asp Met
225                 230                 235                 240

Val Lys Leu Gly Thr Leu Thr Ser Pro Glu Pro Val Ala Ile Thr Val
                245                 250                 255

Val Arg Ser Val Asn Thr Cys Asn Cys Asn Asp Arg Asn Ala Glu Ile
            260                 265                 270

Glu Asn Gly Gln Gly Val Arg Asn Ser Ala Ala Thr Thr
        275                 280                 285
```

<210> SEQ ID NO 22
<211> LENGTH: 858
<212> TYPE: DNA
<213> ORGANISM: Artificial sequence
<220> FEATURE:
<223> OTHER INFORMATION: Synthesized: AtSWEET12 (Arabidopsis thaliana)

<400> SEQUENCE: 22

```
atggctctct tcgacactca taacacatgg gcctttgttt tcggcttgct cggaaacctc      60

atttcctttg ctgttttcct ctctcccgtg ccaacgttct ataggatttg taagaagaaa     120

accacagaag gatttcaatc tattccctat gtggtggcgc tcttcagcgc gatgctttgg     180

ctctactacg ctactcagaa gaaagatgtc ttccttctcg tcaccatcaa cagctttggt     240

tgcttcattg aaaccatata catctccatc tttgttgcct tcgcatccaa gaaagcccga     300

atgctaacgg tgaagctctt gttgctaatg aactttggag ggttctgttt gattctcctc     360

ctctgccaat tcttggcaaa aggaaccaca cgtgcgaaga tcattggagg tatctgtgtc     420
```

```
ggattctctg tctgcgtttt tgctgcgccg cttagcatta tcagaacggt gataaagacg    480

aaaagtgtgg agtacatgcc gtttagctta tccttgactc ttaccatcag tgcggtcata    540

tggctccttt atggtcttgc tcttaaggat atctatgttg ccttcccaaa cgtgattggg    600

tttgttctag gtgcacttca aatgatactc tatgtggttt acaaatactg caaaacgccg    660

tcggatttgg ttgagaaaga acttgaggct gcgaaattgc cagaagtgag catcgatatg    720

gtgaagttag gtacactcac atctcctgaa ccagtagcga tcaccgtcgt ccgatcggtg    780

aacacatgta actgtaacga tcgaaatgct gagattgaaa atggtcaggg agttagaaac    840

agtgctgcaa ctacttga                                                  858


<210> SEQ ID NO 23
<211> LENGTH: 294
<212> TYPE: PRT
<213> ORGANISM: Artificial sequence
<220> FEATURE:
<223> OTHER INFORMATION: Synthesized: AtSWEET13 (Arabidopsis thaliana)

<400> SEQUENCE: 23

Met Ala Leu Thr Asn Asn Leu Trp Ala Phe Val Phe Gly Ile Leu Gly
1               5                   10                  15

Asn Ile Ile Ser Phe Val Val Phe Leu Ala Pro Val Pro Thr Phe Val
            20                  25                  30

Arg Ile Cys Lys Lys Lys Ser Thr Glu Gly Phe Gln Ser Leu Pro Tyr
        35                  40                  45

Val Ser Ala Leu Phe Ser Ala Met Leu Trp Ile Tyr Tyr Ala Met Gln
    50                  55                  60

Lys Asp Gly Thr Ala Phe Leu Leu Ile Thr Ile Asn Ala Phe Gly Cys
65                  70                  75                  80

Val Ile Glu Thr Ile Tyr Ile Val Leu Phe Val Ser Tyr Ala Asn Lys
                85                  90                  95

Lys Thr Arg Ile Ser Thr Leu Lys Val Leu Gly Leu Leu Asn Phe Leu
            100                 105                 110

Gly Phe Ala Ala Ile Val Leu Val Cys Glu Leu Leu Thr Lys Gly Ser
        115                 120                 125

Thr Arg Glu Lys Val Leu Gly Gly Ile Cys Val Gly Phe Ser Val Ser
    130                 135                 140

Val Phe Ala Ala Pro Leu Ser Ile Met Arg Val Val Val Arg Thr Arg
145                 150                 155                 160

Ser Val Glu Phe Met Pro Phe Ser Leu Ser Leu Phe Leu Thr Ile Ser
                165                 170                 175

Ala Val Thr Trp Leu Phe Tyr Gly Leu Ala Ile Lys Asp Phe Tyr Val
            180                 185                 190

Ala Leu Pro Asn Val Leu Gly Ala Phe Leu Gly Ala Val Gln Met Ile
        195                 200                 205

Leu Tyr Ile Ile Phe Lys Tyr Tyr Lys Thr Pro Val Ala Gln Lys Thr
    210                 215                 220

Asp Lys Ser Lys Asp Val Ser Asp His Ser Ile Asp Ile Ala Lys Leu
225                 230                 235                 240

Thr Thr Val Ile Pro Gly Ala Val Leu Asp Ser Ala Val His Gln Pro
                245                 250                 255

Pro Ala Leu His Asn Val Pro Glu Thr Lys Ile Gln Leu Thr Glu Val
            260                 265                 270

Lys Ser Gln Asn Met Thr Asp Pro Lys Asp Gln Ile Asn Lys Asp Val
        275                 280                 285
```

```
Gln Lys Gln Ser Gln Val
    290


<210> SEQ ID NO 24
<211> LENGTH: 885
<212> TYPE: DNA
<213> ORGANISM: Artificial sequence
<220> FEATURE:
<223> OTHER INFORMATION: Synthesized: AtSWEET13 (Arabidopsis thaliana)

<400> SEQUENCE: 24

atggctctaa ctaacaattt atgggcattt gtgtttggaa tcttgggtaa catcatatca      60

ttcgtcgtgt tcttggcccc agtgcccact tttgtaagga tatgcaagaa gaaatcaacc     120

gaaggttttc agtctctacc ctatgtttca gcacttttta gcgcgatgct ttggatttac     180

tacgctatgc aaaaagatgg cacagccttt cttctcatca ccataaacgc ttttggatgc     240

gtcatcgaaa ccatctacat cgtcctcttt gtctcctatg ctaacaagaa aactagaata     300

tccactttga aagttcttgg tctcttgaac tttttgggat ttgccgccat tgttcttgtc     360

tgcsagctct taaccaaagg ttcaacacgt gagaaagttc tcggagggat ttgcgttgga     420

ttttccgtca gtgttttcgc agctcctttg agtatcatga gagtggtggt acgaacaaga     480

agtgtggagt ttatgccttt ctctttatcg ttgtttctta caattagcgc cgtcacgtgg     540

ctcttctacg gtctcgctat taaagacttc tacgttgccc ttccaaatgt attaggcgcg     600

ttcttaggag ctgttcaaat gattctctac ataattttca aatactacaa aactcctgtg     660

gctcagaaga cagataaatc caaagacgtg tccgatcatt ccatcgacat agcaaagcta     720

acgaccgtca tacccggtgc agttttggat tccgcggttc atcaaccgcc tgctcttcac     780

aatgttcccg agactaaaat tcaattgacc gaggtcaaga gccagaacat gaccgatccg     840

aaagaccaga tcaacaagga tgtccagaaa caaagtcaag tttaa                     885


<210> SEQ ID NO 25
<211> LENGTH: 281
<212> TYPE: PRT
<213> ORGANISM: Artificial sequence
<220> FEATURE:
<223> OTHER INFORMATION: Synthesized: AtSWEET14 (Arabidopsis thaliana)

<400> SEQUENCE: 25

Met Val Leu Thr His Asn Val Leu Ala Val Thr Phe Gly Val Leu Gly
1               5                   10                  15

Asn Ile Ile Ser Phe Ile Val Phe Leu Ala Pro Val Pro Thr Phe Val
            20                  25                  30

Arg Ile Cys Lys Lys Lys Ser Ile Glu Gly Phe Glu Ser Leu Pro Tyr
        35                  40                  45

Val Ser Ala Leu Phe Ser Ala Met Leu Trp Ile Tyr Tyr Ala Leu Gln
    50                  55                  60

Lys Asp Gly Ala Gly Phe Leu Leu Ile Thr Ile Asn Ala Val Gly Cys
65                  70                  75                  80

Phe Ile Glu Thr Ile Tyr Ile Ile Leu Phe Ile Thr Tyr Ala Asn Lys
                85                  90                  95

Lys Ala Arg Ile Ser Thr Leu Lys Val Leu Gly Leu Leu Asn Phe Leu
            100                 105                 110

Gly Phe Ala Ala Ile Ile Leu Val Cys Glu Leu Leu Thr Lys Gly Ser
        115                 120                 125

Asn Arg Glu Lys Val Leu Gly Gly Ile Cys Val Gly Phe Ser Val Cys
```

```
    130                 135                 140

Val Phe Ala Ala Pro Leu Ser Ile Met Arg Val Val Ile Arg Thr Lys
145                 150                 155                 160

Ser Val Glu Phe Met Pro Phe Ser Leu Ser Leu Phe Leu Thr Ile Ser
                165                 170                 175

Ala Ile Thr Trp Leu Phe Tyr Gly Leu Ala Ile Lys Asp Phe Tyr Val
            180                 185                 190

Ala Leu Pro Asn Ile Leu Gly Ala Phe Leu Gly Ala Val Gln Met Ile
        195                 200                 205

Leu Tyr Val Ile Phe Lys Tyr Tyr Lys Thr Pro Leu Val Val Asp Glu
    210                 215                 220

Thr Glu Lys Pro Lys Thr Val Ser Asp His Ser Ile Asn Met Val Lys
225                 230                 235                 240

Leu Ser Ser Thr Pro Ala Ser Gly Asp Leu Thr Val Gln Pro Gln Thr
                245                 250                 255

Asn Pro Asp Val Ser His Pro Ile Lys Thr His Gly Gly Asp Leu Glu
            260                 265                 270

Asp Gln Met Asp Lys Lys Met Pro Asn
        275                 280


<210> SEQ ID NO 26
<211> LENGTH: 846
<212> TYPE: DNA
<213> ORGANISM: Artificial sequence
<220> FEATURE:
<223> OTHER INFORMATION: Synthesized: AtSWEET14 (Arabidopsis thaliana)

<400> SEQUENCE: 26

atggttctca ctcacaacgt attggcagtt acatttggag tcctgggtaa catcatatcg     60

ttcatcgttt tcttggcacc agtgccaact tttgtaagaa tctgcaagaa aaaatcgata    120

gaaggttttg aatcacttcc ctacgtgtca gccctcttta gcgcgatgct atggatttac    180

tatgctctgc aaaaagatgg agcaggcttc cttctcatta ccataaacgc tgtgggatgc    240

ttcatcgaaa ccatctacat catcctcttc atcacctatg ctaacaagaa agctagaata    300

tcaactttga aggttcttgg gctcttgaat ttcttgggtt ttgctgctat tattctcgtc    360

tgcgagctcc taaccaaagg atcgaaccgt gagaaagtcc ttggagggat ttgcgtcgga    420

ttttctgttt gtgttttcgc agctcctttg agcatcatga gagtggtgat acgaacaaag    480

agtgtggagt ttatgccttt ctctctatca ttgtttctta caatcagcgc cattacgtgg    540

ctcttctacg gtcttgctat taaagacttc tacgttgcgc ttccaaatat attgggtgcg    600

tttctcggag cagtccaaat gattctatac gtcatattca agtactacaa aactccacta    660

gtggttgatg agacagagaa gcccaaaacg gtgtcggatc attccatcaa catggtcaag    720

ctttcatcta ctccggcttc tggtgatctt acggttcagc cgcagactaa tcctgacgtg    780

agtcatccta ttaaaactca tggtggtgac ttagaggacc agatggacaa gaaaatgcca    840

aactaa                                                                846


<210> SEQ ID NO 27
<211> LENGTH: 292
<212> TYPE: PRT
<213> ORGANISM: Artificial sequence
<220> FEATURE:
<223> OTHER INFORMATION: Synthesized: AtSWEET15 (Arabidopsis thaliana)

<400> SEQUENCE: 27
```

-continued

```
Met Gly Val Met Ile Asn His His Phe Leu Ala Phe Ile Phe Gly Ile
1               5                   10                  15

Leu Gly Asn Val Ile Ser Phe Leu Val Phe Leu Ala Pro Val Pro Thr
            20                  25                  30

Phe Tyr Arg Ile Tyr Lys Arg Lys Ser Thr Glu Ser Phe Gln Ser Leu
        35                  40                  45

Pro Tyr Gln Val Ser Leu Phe Ser Cys Met Leu Trp Leu Tyr Tyr Ala
    50                  55                  60

Leu Ile Lys Lys Asp Ala Phe Leu Leu Ile Thr Ile Asn Ser Phe Gly
65                  70                  75                  80

Cys Val Val Glu Thr Leu Tyr Ile Ala Met Phe Phe Ala Tyr Ala Thr
                85                  90                  95

Arg Glu Lys Arg Ile Ser Ala Met Lys Leu Phe Ile Ala Met Asn Val
            100                 105                 110

Ala Phe Phe Ser Leu Ile Leu Met Val Thr His Phe Val Val Lys Thr
        115                 120                 125

Pro Pro Leu Gln Val Ser Val Leu Gly Trp Ile Cys Val Ala Ile Ser
    130                 135                 140

Val Ser Val Phe Ala Ala Pro Leu Met Ile Val Ala Arg Val Ile Lys
145                 150                 155                 160

Thr Lys Ser Val Glu Tyr Met Pro Phe Thr Leu Ser Phe Phe Leu Thr
                165                 170                 175

Ile Ser Ala Val Met Trp Phe Ala Tyr Gly Leu Phe Leu Asn Asp Ile
            180                 185                 190

Cys Ile Ala Ile Pro Asn Val Val Gly Phe Val Leu Gly Leu Leu Gln
        195                 200                 205

Met Val Leu Tyr Leu Val Tyr Arg Asn Ser Asn Glu Lys Pro Glu Lys
    210                 215                 220

Ile Asn Ser Ser Glu Gln Gln Leu Lys Ser Ile Val Val Met Ser Pro
225                 230                 235                 240

Leu Gly Val Ser Glu Val His Pro Val Val Thr Glu Ser Val Asp Pro
                245                 250                 255

Leu Ser Glu Ala Val His His Glu Asp Leu Ser Lys Val Thr Lys Val
            260                 265                 270

Glu Glu Pro Ser Ile Glu Asn Gly Lys Cys Tyr Val Glu Ala Thr Arg
        275                 280                 285

Pro Glu Thr Val
    290
```

<210> SEQ ID NO 28
<211> LENGTH: 879
<212> TYPE: DNA
<213> ORGANISM: Artificial sequence
<220> FEATURE:
<223> OTHER INFORMATION: Synthesized: AtSWEET15 (Arabidopsis thaliana)

<400> SEQUENCE: 28

```
atgggagtca tgatcaatca ccatttcctc gcttttatct tcggcatctt aggaaacgtg      60

atatccttcc ttgtattcct cgctccagtg ccaacttttt atagaatata caagagaaaa     120

tcgacggaaa gtttccagtc gctaccgtac caagtgtcgc tatttagctg catgctatgg     180

ctctactacg cattgattaa gaaagacgct tttctcctaa ttaccatcaa ctcctttggc     240

tgcgtcgtgg agactctcta catagccatg ttcttcgctt acgccaccag ggagaaaagg     300

atatcggcta tgaagttgtt catagcaatg aacgttgcct tcttctcgtt gattctaatg     360
```

```
gtaacacatt tcgtggttaa aactcctccc ctccaagtct ctgtactcgg ctggatttgt    420

gttgccattt ctgtttctgt tttcgctgcc cctctaatga tcgtggctcg tgtgataaag    480

acaaagagtg tggagtacat gcccttcacg ctttctttct tcctcactat aagcgccgtt    540

atgtggttcg cttatggttt attcctcaat gacatatgca tagcgattcc aaacgtggtg    600

ggattcgtac tagggctgtt gcaaatggtt ttgtacttgg tttacaggaa ctcaaatgag    660

aaaccagaga agattaattc gtcagaacaa caacttaaga gtattgtcgt gatgagtccg    720

ttaggtgtgt cggaagtgca cccagttgtg acggaatcgg tggacccact ctctgaagcc    780

gttcatcatg aggatctgtc caaagttact aaagtggagg agccgtcaat tgaaaacggc    840

aagtgctacg tggaggctac tcgtcctgaa accgtttga                           879
```

```
<210> SEQ ID NO 29
<211> LENGTH: 307
<212> TYPE: PRT
<213> ORGANISM: Artificial sequence
<220> FEATURE:
<223> OTHER INFORMATION: Synthesized: OzSWEET11 (Oryza sativa japonica)

<400> SEQUENCE: 29

Met Ala Gly Gly Phe Leu Ser Met Ala Asn Pro Ala Val Thr Leu Ser
1               5                   10                  15

Gly Val Ala Gly Asn Ile Ile Ser Phe Leu Val Phe Leu Ala Pro Val
            20                  25                  30

Ala Thr Phe Leu Gln Val Tyr Lys Lys Lys Ser Thr Gly Gly Tyr Ser
        35                  40                  45

Ser Val Pro Tyr Val Val Ala Leu Phe Ser Ser Val Leu Trp Ile Phe
    50                  55                  60

Tyr Ala Leu Val Lys Thr Asn Ser Arg Pro Leu Leu Thr Ile Asn Ala
65                  70                  75                  80

Phe Gly Cys Gly Val Glu Ala Ala Tyr Ile Val Leu Tyr Leu Val Tyr
                85                  90                  95

Ala Pro Arg Arg Ala Arg Leu Arg Thr Leu Ala Phe Phe Leu Leu Leu
            100                 105                 110

Asp Val Ala Ala Phe Ala Leu Ile Val Val Thr Thr Leu Tyr Leu Val
        115                 120                 125

Pro Lys Pro His Gln Val Lys Phe Leu Gly Ser Val Cys Leu Ala Phe
    130                 135                 140

Ser Met Ala Val Phe Val Ala Pro Leu Ser Ile Ile Phe Lys Val Ile
145                 150                 155                 160

Lys Thr Lys Ser Val Glu Phe Met Pro Ile Gly Leu Ser Val Cys Leu
                165                 170                 175

Thr Leu Ser Ala Val Ala Trp Phe Cys Tyr Gly Leu Phe Thr Lys Asp
            180                 185                 190

Pro Tyr Val Met Tyr Pro Asn Val Gly Gly Phe Phe Phe Ser Cys Val
        195                 200                 205

Gln Met Gly Leu Tyr Phe Trp Tyr Arg Lys Pro Arg Asn Thr Ala Val
    210                 215                 220

Leu Pro Thr Thr Ser Asp Ser Met Ser Pro Ile Ser Ala Ala Ala Ala
225                 230                 235                 240

Ala Thr Gln Arg Val Ile Glu Leu Pro Ala Gly Thr His Ala Phe Thr
                245                 250                 255

Ile Leu Ser Val Ser Pro Ile Pro Ile Leu Gly Val His Lys Val Glu
            260                 265                 270
```

-continued

```
Val Val Ala Ala Glu Gln Ala Ala Asp Gly Val Ala Ala Ala Ala Ala
        275                 280                 285

Ala Asp Lys Glu Leu Leu Gln Asn Lys Pro Glu Val Ile Glu Ile Thr
    290                 295                 300

Ala Ala Val
305


<210> SEQ ID NO 30
<211> LENGTH: 924
<212> TYPE: DNA
<213> ORGANISM: Artificial sequence
<220> FEATURE:
<223> OTHER INFORMATION: Synthesized: OzSWEET11 (Oryza sativa japonica)

<400> SEQUENCE: 30

atggcaggag gtttcttgtc catggctaac ccggcggtca ccctctccgg tgttgcagga     60

aacatcatct ccttcctggt gttccttgca ccagtggcga cgttcttgca ggtgtacaag    120

aagaagtcga cgggagggta cagctcggtg ccgtacgtgg tggcgctctt cagctcggtg    180

ctgtggatct tctacgcgct ggtgaagacc aactcgaggc cgctgctgac catcaacgcc    240

ttcggctgcg gcgtcgaggc cgcctacatc gtcctctacc tcgtctacgc gccgcgccgc    300

gccaggctcc gcaccctcgc cttcttcctc ctcctcgacg tcgccgcctt cgccctcatc    360

gtcgtcacca ccctctacct cgtccccaag ccccaccagg tcaagttcct cggcagcgtc    420

tgcctcgcct tctccatggc cgtcttcgtc gcccctctct ccatcatctt caaggtgatc    480

aagaccaaga gcgtcgagtt catgccgatc gggctctccg tctgcctcac gctcagcgcc    540

gtcgcgtggt tctgctacgg cctcttcacc aaggacccct acgtcatgta cccgaacgtg    600

ggcggcttct tcttcagctg cgtgcagatg ggctctact tctggtaccg gaagccgagg    660

aacacggccg tgctgccgac gacgtccgac tccatgtccc cgatctccgc cgccgccgcc    720

gccacgcaga gggtgatcga gctccccgcc ggcacgcacg ccttcaccat cctgtccgtg    780

agccccatcc cgatcctcgg cgtgcacaag gtcgaggtgg tggccgccga gcaggcggcc    840

gacggcgtcg ccgccgccgc cgccgccgac aaggagctgc tgcagaacaa gccggaggtg    900

atcgagatca ccgccgccgt gtga                                           924


<210> SEQ ID NO 31
<211> LENGTH: 303
<212> TYPE: PRT
<213> ORGANISM: Artificial sequence
<220> FEATURE:
<223> OTHER INFORMATION: Synthesized: OzSWEET14 (Oryza sativa japonica)

<400> SEQUENCE: 31

Met Ala Gly Met Ser Leu Gln His Pro Trp Ala Phe Ala Phe Gly Leu
1               5                   10                  15

Leu Gly Asn Ile Ile Ser Phe Met Thr Tyr Leu Ala Pro Leu Pro Thr
            20                  25                  30

Phe Tyr Arg Ile Tyr Lys Ser Lys Ser Thr Gln Gly Phe Gln Ser Val
        35                  40                  45

Pro Tyr Val Val Ala Leu Phe Ser Ala Met Leu Trp Ile Tyr Tyr Ala
    50                  55                  60

Leu Leu Lys Ser Asp Glu Cys Leu Leu Ile Thr Ile Asn Ser Ala Gly
65                  70                  75                  80

Cys Val Ile Glu Thr Ile Tyr Ile Ala Val Tyr Leu Val Tyr Ala Pro
                85                  90                  95
```

-continued

Lys Lys Ala Lys Met Phe Thr Ala Lys Leu Leu Leu Leu Val Asn Val
100 105 110

Gly Val Phe Gly Leu Ile Leu Leu Leu Thr Leu Leu Leu Ser Ala Gly
115 120 125

Asp Arg Arg Ile Val Val Leu Gly Trp Val Cys Val Gly Phe Ser Val
130 135 140

Ser Val Phe Val Ala Pro Leu Ser Ile Ile Arg Leu Val Val Arg Thr
145 150 155 160

Lys Ser Val Glu Phe Met Pro Phe Ser Leu Ser Phe Ser Leu Thr Ile
165 170 175

Ser Ala Val Val Trp Phe Leu Tyr Gly Leu Leu Ile Lys Asp Lys Tyr
180 185 190

Val Ala Leu Pro Asn Val Leu Gly Phe Ser Phe Gly Val Ile Gln Met
195 200 205

Gly Leu Tyr Ala Met Tyr Arg Asn Ser Thr Pro Lys Ala Val Leu Thr
210 215 220

Lys Glu Val Glu Ala Ala Thr Ala Thr Gly Asp Asp Asp His Ser Ala
225 230 235 240

Ala Gly Val Lys Glu His Val Val Asn Ile Ala Lys Leu Ser Ala Ala
245 250 255

Val Asp Val Val Lys Thr Arg Glu Val His Pro Val Asp Val Glu Ser
260 265 270

Pro Pro Ala Glu Ala Pro Pro Glu Glu Asp Asp Lys Ala Ala Ala Ala
275 280 285

Thr Ala Ala Ala Val Ala Gly Ala Gly Glu Lys Lys Val Ala Ala
290 295 300

<210> SEQ ID NO 32
<211> LENGTH: 912
<212> TYPE: DNA
<213> ORGANISM: Artificial sequence
<220> FEATURE:
<223> OTHER INFORMATION: Synthesized: OzSWEET14 (Oryza sativa japonica)

<400> SEQUENCE: 32
atggctggca tgtctcttca gcatccctgg gccttcgcct ttggtctcct aggcaacatc 60
atctccttca tgacctacct ggccccactg ccgacgttct acaggatcta caagagcaag 120
tcgacgcagg ggttccagtc ggtaccctac gtggtggcgc tgttcagcgc gatgctgtgg 180
atctactacg cgctgctcaa gtccgacgag tgcctcctca tcaccatcaa ctccgctggc 240
tgcgtcatcg agaccatcta catcgccgtc tacctcgtct acgcccccaa gaaggccaag 300
atgttcaccg ccaagctcct cctcctcgtc aacgtcggcg tcttcggcct catcctcctc 360
ctcaccctcc tcctctccgc cggcgaccgc cgcatcgtgg ttcttggttg ggtctgcgtt 420
ggcttctccg tcagcgtctt cgtcgccccc cttagcatca tcaggctggt ggtgcgcacc 480
aagagcgtgg agttcatgcc gttctcgctc tccttctccc tcaccatcag cgccgtcgtc 540
tggttcctct acggcctcct catcaaggac aaatatgtcg ctcttcccaa cgtgctgggc 600
ttctccttcg gcgtcatcca gatggggctg tacgccatgt acaggaactc gacgcccaag 660
gccgtgctga ccaaggaggt cgaggcggcg acggccaccg gcgacgacga ccactccgcc 720
gccggcgtca aggagcacgt cgtcaacatc gccaagctct ctgccgccgt cgacgtcgtc 780
aagacccgcg aggtgcaccc cgtcgacgtc gagtccccgc cggcagaggc gccgcctgag 840
gaggacgaca aggccgccgc cgccaccgcc gccgccgtcg ccggcgccgg cgagaagaag 900

```
gtagctgcat ga                                                       912


<210> SEQ ID NO 33
<211> LENGTH: 281
<212> TYPE: PRT
<213> ORGANISM: Artificial sequence
<220> FEATURE:
<223> OTHER INFORMATION: Synthesized: glpF (Escherichia coli)

<400> SEQUENCE: 33

Met Ser Gln Thr Ser Thr Leu Lys Gly Gln Cys Ile Ala Glu Phe Leu
1               5                   10                  15

Gly Thr Gly Leu Leu Ile Phe Phe Gly Val Gly Cys Val Ala Ala Leu
            20                  25                  30

Lys Val Ala Gly Ala Ser Phe Gly Gln Trp Glu Ile Ser Val Ile Trp
        35                  40                  45

Gly Leu Gly Val Ala Met Ala Ile Tyr Leu Thr Ala Gly Val Ser Gly
    50                  55                  60

Ala His Leu Asn Pro Ala Val Thr Ile Ala Leu Trp Leu Phe Ala Cys
65                  70                  75                  80

Phe Asp Lys Arg Lys Val Ile Pro Phe Ile Val Ser Gln Val Ala Gly
                85                  90                  95

Ala Phe Cys Ala Ala Ala Leu Val Tyr Gly Leu Tyr Tyr Asn Leu Phe
            100                 105                 110

Phe Asp Phe Glu Gln Thr His His Ile Val Arg Gly Ser Val Glu Ser
        115                 120                 125

Val Asp Leu Ala Gly Thr Phe Ser Thr Tyr Pro Asn Pro His Ile Asn
    130                 135                 140

Phe Val Gln Ala Phe Ala Val Glu Met Val Ile Thr Ala Ile Leu Met
145                 150                 155                 160

Gly Leu Ile Leu Ala Leu Thr Asp Asp Gly Asn Gly Val Pro Arg Gly
                165                 170                 175

Pro Leu Ala Pro Leu Leu Ile Gly Leu Leu Ile Ala Val Ile Gly Ala
            180                 185                 190

Ser Met Gly Pro Leu Thr Gly Phe Ala Met Asn Pro Ala Arg Asp Phe
        195                 200                 205

Gly Pro Lys Val Phe Ala Trp Leu Ala Gly Trp Gly Asn Val Ala Phe
    210                 215                 220

Thr Gly Gly Arg Asp Ile Pro Tyr Phe Leu Val Pro Leu Phe Gly Pro
225                 230                 235                 240

Ile Val Gly Ala Ile Val Gly Ala Phe Ala Tyr Arg Lys Leu Ile Gly
                245                 250                 255

Arg His Leu Pro Cys Asp Ile Cys Val Val Glu Glu Lys Glu Thr Thr
            260                 265                 270

Thr Pro Ser Glu Gln Lys Ala Ser Leu
        275                 280


<210> SEQ ID NO 34
<211> LENGTH: 846
<212> TYPE: DNA
<213> ORGANISM: Artificial sequence
<220> FEATURE:
<223> OTHER INFORMATION: Synthesized: glpF (Escherichia coli)

<400> SEQUENCE: 34

atgagtcaaa catcaacctt gaaaggccag tgcattgctg aattcctcgg taccgggttg      60

ttgattttct tcggtgtggg ttgcgttgca gcactaaaag tcgctggtgc gtcttttggt     120
```

```
cagtgggaaa tcagtgtcat ttggggactg ggggtggcaa tggccatcta cctgaccgca    180

ggggtttccg gcgcgcatct taatcccgct gttaccattg cattgtggct gtttgcctgt    240

ttcgacaagc gcaaagttat tccttttatc gtttcacaag ttgccggcgc tttctgtgct    300

gcggctttag tttacgggct ttactacaat ttatttttcg acttcgagca gactcatcac    360

attgttcgcg gcagcgttga aagtgttgat ctggctggca ctttctctac ttaccctaat    420

cctcatatca attttgtgca ggctttcgca gttgagatgg tgattaccgc tattctgatg    480

gggctgatcc tggcgttaac ggtcgatggc aacggtgtac cacgcggccc tttggctccc    540

ttgctgattg gtctactgat tgcggtcatt ggcgcatcta tgggcccatt gacaggtttt    600

gccatgaacc cagcgcgtga cttcggtccg aaagtctttg cctggctggc gggctggggc    660

aatgtcgcct ttaccggcgg cagagacatt ccttacttcc tggtgccgct tttcggccct    720

atcgttggcg cgattgtagg tgcatttgcc taccgcaaac tgattggtcg ccatttgcct    780

tgcgatatct gtgttgtgga agaaaaggaa accacaactc cttcagaaca aaaagcttcg    840

ctgtaa                                                               846
```

<210> SEQ ID NO 35
<211> LENGTH: 492
<212> TYPE: PRT
<213> ORGANISM: Artificial sequence
<220> FEATURE:
<223> OTHER INFORMATION: Synthesized: Suc (Xanthomonas campestris campestris)

<400> SEQUENCE: 35

```
Met Lys Ala Lys Pro Thr Leu Ser Phe Trp Gln Ile Trp Asn Met Cys
1               5                   10                  15

Phe Gly Phe Leu Gly Ile Gln Phe Gly Phe Ala Leu Gln Asn Ala Asn
            20                  25                  30

Ala Ser Arg Ile Phe Gln Thr Leu Gly Ala Gln Val Asp Asp Val Pro
        35                  40                  45

Gly Leu Trp Ile Ala Ala Pro Leu Thr Gly Leu Ile Val Gln Pro Ile
    50                  55                  60

Ile Gly Tyr Leu Ser Asp Arg Thr Trp Thr Gly Trp Gly Arg Arg Arg
65                  70                  75                  80

Pro Tyr Phe Met Ile Gly Ala Val Phe Thr Thr Leu Ala Leu Leu Val
                85                  90                  95

Met Pro Asn Ala Pro Val Leu Trp Ile Ala Ala Gly Thr Leu Trp Val
            100                 105                 110

Leu Asp Ala Ser Ile Asn Ile Ser Met Glu Pro Phe Arg Ala Leu Val
        115                 120                 125

Gly Asp Gln Leu Pro Ala Glu Gln Arg Pro Ser Gly Tyr Ala Met Gln
    130                 135                 140

Ser Phe Phe Ile Gly Val Gly Ala Ile Val Ala Ser Phe Leu Pro Trp
145                 150                 155                 160

Leu Leu Thr Arg Trp Gly Val Asp Asn Thr Ala Pro Ala Gly Glu Leu
                165                 170                 175

Pro Asp Ser Val Arg Tyr Ala Phe Tyr Leu Gly Ala Ala Val Leu Phe
            180                 185                 190

Leu Ser Ile Ser Trp Thr Val Leu Arg Thr Arg Glu Tyr Ser Pro Ala
        195                 200                 205

Glu Leu Ala Ala Phe Glu Pro Ala Pro Ala Pro Ala Ala Ala Gln Leu
    210                 215                 220
```

```
Ala Ala Thr Asp Gln Pro Ser Leu Gln Ala Ser Val Leu Trp Cys Leu
225                 230                 235                 240

Gly Gly Leu Leu Leu Ala Ala Ala Ile Ala Trp Gln His Gly Asp Arg
                245                 250                 255

Met Leu Tyr Val Leu Ala Gly Leu Cys Val Ala Tyr Gly Val Leu Leu
            260                 265                 270

Ala Phe Ala Arg Val Leu Pro Arg Gly Gly Met Leu Val Ala Ile Met
        275                 280                 285

His Asp Leu Arg His Met Pro Gln Thr Met Arg Arg Leu Ala Trp Val
    290                 295                 300

Gln Phe Phe Ser Trp Phe Ala Leu Phe Ala Met Trp Ile Tyr Thr Thr
305                 310                 315                 320

Ala Ala Val Thr Gln Val His Phe Gly Ala Arg Asp Thr Val Ser Ala
                325                 330                 335

Ala Tyr Asn Asp Gly Ala Asn Trp Val Gly Val Leu Phe Gly Ala Tyr
            340                 345                 350

Asn Gly Phe Ala Ala Leu Ala Ala Ile Val Ile Pro Leu Met Val Arg
        355                 360                 365

Ala Ile Gly Leu Arg Trp Ser His Leu Cys Asn Leu Trp Leu Gly Ala
    370                 375                 380

Ala Gly Leu Leu Ser Met Leu Val Ile Arg Asp Pro Tyr Trp Leu Leu
385                 390                 395                 400

Leu Ser Met Leu Gly Val Gly Phe Ala Trp Ala Ser Ile Leu Ser Leu
                405                 410                 415

Pro Tyr Ala Leu Leu Ser Asp Ser Val Pro Ala Ala Lys Met Gly Val
            420                 425                 430

Tyr Met Gly Ile Phe Asn Phe Phe Ile Val Ile Pro Gln Leu Val Ala
        435                 440                 445

Ala Ser Ala Leu Gly Phe Val Leu Arg Val Trp Leu Gly Gly Gln Pro
    450                 455                 460

Ile Tyr Ala Leu Ala Ile Gly Gly Leu Ser Leu Ile Val Ala Gly Val
465                 470                 475                 480

Cys Val Val Arg Val Pro Ser Ala Gln Gly Gly Gln
                485                 490
```

<210> SEQ ID NO 36
<211> LENGTH: 1479
<212> TYPE: DNA
<213> ORGANISM: Artificial sequence
<220> FEATURE:
<223> OTHER INFORMATION: Synthesized: Suc (Xanthomonas campestris campestris)

<400> SEQUENCE: 36

```
atgaaggcca agccaacgct gagtttctgg cagatctgga acatgtgctt tggattcctc      60

ggcatccagt tcgggtttgc gctgcaaaac gccaatgcca gccgcatctt ccagacgctg     120

ggcgcgcagg tcgacgatgt gcccgggctg tggattgccg cgccgctgac cgggctgatc     180

gtgcagccca tcatcggcta tctctccgac cgcacctgga ccggctgggg ccgccgccgg     240

ccgtacttca tgatcggtgc ggtgttcacc acgctggcgt tgctggtgat gcccaacgcg     300

ccggtgctgt ggatcgcagc cggcacgctg tgggtactgg acgcgtccat caacatttcg     360

atggagccat tccgcgcctt ggtcggtgac cagctgccgg ccgagcaacg ccccagcggc     420

tacgcgatgc agagcttttt cattggcgtc ggcgcgattg tggcgagctt tctgccctgg     480
```

```
ctgctgacgc gctggggcgt agacaacact gcacctgccg gcgagctgcc cgatagcgtg    540

cgctacgcgt tctacctagg tgcggcggtg ttgttcctgt cgatcagctg gacggtgctg    600

cgcacgcgcg aatacagccc ggccgagctg gcggcgtttg aaccggcgcc ggcaccggct    660

gccgcgcaac tggccgccac cgatcaaccc agcctgcagg ccagtgtgct gtggtgtctg    720

ggcgggttgc tgctggccgc tgccatcgcc tggcagcacg gcgatcgcat gttgtacgtg    780

ctggcgggcc tgtgcgtcgc ctatggcgtg ctgctggcat ttgcgcgcgt gctgccgcgt    840

ggcggcatgt tggtggcgat catgcacgat ctgcgccaca tgccgcagac gatgcggcgc    900

ctggcctggg tgcagttctt ttcgtggttt gcgctgtttg cgatgtggat ctacaccacc    960

gcggcagtga cgcaggtgca tttcggcgca cgcgataccg tctcggccgc ctacaacgac   1020

ggggcgaact gggtgggtgt gttgttcggc gcctacaacg gctttgccgc gctcgccgcc   1080

atcgtcatcc cgctgatggt gcgtgcgatc gggctgcgct ggagccacct gtgcaatctg   1140

tggctgggtg cggcggggtt gttgtcgatg ctggtcatcc gcgacccgta ctggctgctg   1200

ctgtcgatgc tgggcgtcgg ttttgcctgg gcctcgatcc tgtccttgcc ctatgcactg   1260

ctgtccgaca gcgtgcccgc cgccaagatg ggcgtgtaca tgggcatctt caatttcttt   1320

atcgtgattc cgcaattggt tgccgccagc gccctgggct tcgtgctccg cgtgtggctg   1380

ggcgggcaac cgatctacgc gctggcgatc ggcggcttga gcctgatcgt ggccggtgtg   1440

tgcgtggtgc gggtcccaag cgcccaggga gggcaatga                          1479
```

<210> SEQ ID NO 37
<211> LENGTH: 579
<212> TYPE: PRT
<213> ORGANISM: Artificial sequence
<220> FEATURE:
<223> OTHER INFORMATION: Synthesized: Cdt-1 (Neurospora crassa)

<400> SEQUENCE: 37

```
Met Ser Ser His Gly Ser His Asp Gly Ala Ser Thr Glu Lys His Leu
1               5                   10                  15

Ala Thr His Asp Ile Ala Pro Thr His Asp Ala Ile Lys Ile Val Pro
            20                  25                  30

Lys Gly His Gly Gln Thr Ala Thr Lys Pro Gly Ala Gln Glu Lys Glu
        35                  40                  45

Val Arg Asn Ala Ala Leu Phe Ala Ala Ile Lys Glu Ser Asn Ile Lys
    50                  55                  60

Pro Trp Ser Lys Glu Ser Ile His Leu Tyr Phe Ala Ile Phe Val Ala
65                  70                  75                  80

Phe Cys Cys Ala Cys Ala Asn Gly Tyr Asp Gly Ser Leu Met Thr Gly
                85                  90                  95

Ile Ile Ala Met Asp Lys Phe Gln Asn Gln Phe His Thr Gly Asp Thr
            100                 105                 110

Gly Pro Lys Val Ser Val Ile Phe Ser Leu Tyr Thr Val Gly Ala Met
        115                 120                 125

Val Gly Ala Pro Phe Ala Ala Ile Leu Ser Asp Arg Phe Gly Arg Lys
    130                 135                 140

Lys Gly Met Phe Ile Gly Gly Ile Phe Ile Ile Val Gly Ser Ile Ile
145                 150                 155                 160

Val Ala Ser Ser Ser Lys Leu Ala Gln Phe Val Val Gly Arg Phe Val
                165                 170                 175

Leu Gly Leu Gly Ile Ala Ile Met Thr Val Ala Ala Pro Ala Tyr Ser
            180                 185                 190
```

-continued

```
Ile Glu Ile Ala Pro Pro His Trp Arg Gly Arg Cys Thr Gly Phe Tyr
        195                 200                 205

Asn Cys Gly Trp Phe Gly Gly Ser Ile Pro Ala Ala Cys Ile Thr Tyr
    210                 215                 220

Gly Cys Tyr Phe Ile Lys Ser Asn Trp Ser Trp Arg Ile Pro Leu Ile
225                 230                 235                 240

Leu Gln Ala Phe Thr Cys Leu Ile Val Met Ser Ser Val Phe Phe Leu
                245                 250                 255

Pro Glu Ser Pro Arg Phe Leu Phe Ala Asn Gly Arg Asp Ala Glu Ala
            260                 265                 270

Val Ala Phe Leu Val Lys Tyr His Gly Asn Gly Asp Pro Asn Ser Lys
        275                 280                 285

Leu Val Leu Leu Glu Thr Glu Glu Met Arg Asp Gly Ile Arg Thr Asp
    290                 295                 300

Gly Val Asp Lys Val Trp Trp Asp Tyr Arg Pro Leu Phe Met Thr His
305                 310                 315                 320

Ser Gly Arg Trp Arg Met Ala Gln Val Leu Met Ile Ser Ile Phe Gly
                325                 330                 335

Gln Phe Ser Gly Asn Gly Leu Gly Tyr Phe Asn Thr Val Ile Phe Lys
            340                 345                 350

Asn Ile Gly Val Thr Ser Thr Ser Gln Gln Leu Ala Tyr Asn Ile Leu
        355                 360                 365

Asn Ser Val Ile Ser Ala Ile Gly Ala Leu Thr Ala Val Ser Met Thr
    370                 375                 380

Asp Arg Met Pro Arg Arg Ala Val Leu Ile Ile Gly Thr Phe Met Cys
385                 390                 395                 400

Ala Ala Ala Leu Ala Thr Asn Ser Gly Leu Ser Ala Thr Leu Asp Lys
                405                 410                 415

Gln Thr Gln Arg Gly Thr Gln Ile Asn Leu Asn Gln Gly Met Asn Glu
            420                 425                 430

Gln Asp Ala Lys Asp Asn Ala Tyr Leu His Val Asp Ser Asn Tyr Ala
        435                 440                 445

Lys Gly Ala Leu Ala Ala Tyr Phe Leu Phe Asn Val Ile Phe Ser Phe
    450                 455                 460

Thr Tyr Thr Pro Leu Gln Gly Val Ile Pro Thr Glu Ala Leu Glu Thr
465                 470                 475                 480

Thr Ile Arg Gly Lys Gly Leu Ala Leu Ser Gly Phe Ile Val Asn Ala
                485                 490                 495

Met Gly Phe Ile Asn Gln Phe Ala Gly Pro Ile Ala Leu His Asn Ile
            500                 505                 510

Gly Tyr Lys Tyr Ile Phe Val Phe Val Gly Trp Asp Leu Ile Glu Thr
        515                 520                 525

Val Ala Trp Tyr Phe Phe Gly Val Glu Ser Gln Gly Arg Thr Leu Glu
    530                 535                 540

Gln Leu Glu Trp Val Tyr Asp Gln Pro Asn Pro Val Lys Ala Ser Leu
545                 550                 555                 560

Lys Val Glu Lys Val Val Val Gln Ala Asp Gly His Val Ser Glu Ala
                565                 570                 575

Ile Val Ala
```

<210> SEQ ID NO 38
<211> LENGTH: 1883
<212> TYPE: DNA

-continued

<213> ORGANISM: Artificial sequence
<220> FEATURE:
<223> OTHER INFORMATION: Synthesized: Cdt-1 (Neurospora crassa)

<400> SEQUENCE: 38
atgtcgtctc acggctccca tgacggggcc agcaccgaga agcatcttgc tactcatgac 60
attgcgccca cccacgacgc catcaagata gtgcccaagg gccatggcca gacagccaca 120
aagcccggtg cccaagagaa ggaggtccgc aacgccgccc tatttgcggc catcaaggag 180
tccaatatca agccctggag caaggagtcc atccacctct atttcgccat cttcgtcgcc 240
ttttgttgtg catgcgccaa cggttacgat ggttcactca tgaccggaat catcgctatg 300
gacaagttcc agaaccaatt ccacactggt gacactggtc ctaaagtctc tgtcatcttt 360
tctctctata ccgtgtaagt gattagggat ttagcaaatc actccttttt ggtttggggc 420
ttttctaaca cctcgagtct tccagtggtg ccatggttgg agctcccttc gctgctatcc 480
tctctgatcg ttttggccgt aagaagggca tgttcatcgg tggtatcttt atcattgtcg 540
gctccattat tgttgctagc tcctccaagc tcgctcagtt tgtcgttggc cgcttcgttc 600
ttggcctcgg tatcgccatc atgaccgttg ctgccccggc ctactccatc gaaatcgccc 660
ctcctcactg gcgcggccgc tgcactggct tctacaactg cggttggttc ggaggttcga 720
ttcctgccgc ctgcatcacc tatggctgct acttcattaa gagcaactgg tcatggcgta 780 tcccccttgat ccttcaggct ttcacgtgcc ttatcgtcat gtcctccgtc ttcttcctcc 840
cagaatcccc tcgcttccta tttgccaacg gccgcgacgc tgaggctgtt gcctttcttg 900
tcaagtatca cggcaacggc gatcccaatt ccaagctggt gttgctcgag actgaggaga 960
tgagggacgg tatcaggacc gacggtgtcg acaaggtctg gtgggattac cgcccgctct 1020
tcatgaccca cagcggccgc tggcgcatgg cccaggtgct catgatctcc atctttggcc 1080
agttctccgg caacggtctc ggttacttca ataccgtcat cttcaagaac attggtgtca 1140
ccagcacctc ccaacagctc gcctacaaca tcctcaactc cgtcatctcc gctatcggtg 1200
ccttgaccgc cgtctccatg actgatcgta tgccccgccg cgcggtgctc attatcggta 1260
ccttcatgtg cgccgctgct cttgccacca actcgggtct ttcggctact ctcgacaagc 1320
agactcaaag aggcacgcaa atcaacctga accagggtat gaacgagcag gatgccaagg 1380
acaacgccta cctccacgtc gacagcaact acgccaaggg tgccctggcc gcttacttcc 1440
tcttcaacgt catcttctcc ttcacctaca ctcccctcca gggtgttatt cccaccgagg 1500
ctctcgagac caccatccgt ggcaagggtc ttgccctttc cggcttcatt gtcaacgcca 1560
tgggcttcat caaccagttc gctggcccca tcgctctcca caacattggc tacaagtaca 1620
tctttgtctt tgtcggctgg gatcttatcg agaccgtcgc ttggtacttc tttgggtatg 1680
ttttgggtct tcttctctgt cgacatcgcg taaacagcac acagatcgct aactcgttcc 1740
actacagtgt cgaatcccaa ggccgtaccc tcgagcagct cgaatgggtc tacgaccagc 1800
ccaaccccgt caaggcctcc ctaaaagtcg aaaaggtcgt cgtccaggcc gacggccatg 1860
tgtccgaagc tatcgttgct tag 1883

<210> SEQ ID NO 39
<211> LENGTH: 525
<212> TYPE: PRT
<213> ORGANISM: Artificial sequence
<220> FEATURE:
<223> OTHER INFORMATION: Synthesized: Cdt-2 (Neurospora crassa)

<400> SEQUENCE: 39

```
Met Gly Ile Phe Asn Lys Lys Pro Val Ala Gln Ala Val Asp Leu Asn
1               5                   10                  15

Gln Ile Gln Glu Glu Ala Pro Gln Phe Glu Arg Val Asp Trp Lys Lys
            20                  25                  30

Asp Pro Gly Leu Arg Lys Leu Tyr Phe Tyr Ala Phe Ile Leu Cys Ile
        35                  40                  45

Ala Ser Ala Thr Thr Gly Tyr Asp Gly Met Phe Phe Asn Ser Val Gln
    50                  55                  60

Asn Phe Glu Thr Trp Ile Lys Tyr Phe Gly Asp Pro Arg Gly Ser Glu
65                  70                  75                  80

Leu Gly Leu Leu Gly Ala Leu Tyr Gln Ile Gly Ser Ile Gly Ser Ile
                85                  90                  95

Pro Phe Val Pro Leu Leu Thr Asp Asn Phe Gly Arg Lys Thr Pro Ile
            100                 105                 110

Ile Ile Gly Cys Val Ile Met Ile Val Gly Ala Val Leu Gln Ala Thr
        115                 120                 125

Ala Lys Asn Leu Asp Thr Phe Met Gly Gly Arg Thr Met Leu Gly Phe
    130                 135                 140

Gly Asn Ser Leu Ala Gln Ile Ala Ser Pro Met Leu Leu Thr Glu Leu
145                 150                 155                 160

Ala His Pro Gln His Arg Ala Arg Leu Thr Thr Ile Tyr Asn Cys Leu
                165                 170                 175

Trp Asn Val Gly Ala Leu Val Val Ser Trp Leu Ala Phe Gly Thr Asn
            180                 185                 190

Tyr Ile Asn Asn Asp Trp Ser Trp Arg Ile Pro Ala Leu Leu Gln Ala
        195                 200                 205

Phe Pro Ser Ile Ile Gln Leu Leu Gly Ile Trp Trp Val Pro Glu Ser
    210                 215                 220

Pro Arg Phe Leu Ile Ala Lys Asp Lys His Asp Glu Ala Leu His Ile
225                 230                 235                 240

Leu Ala Lys Tyr His Ala Asn Gly Asp Pro Asn His Pro Thr Val Gln
                245                 250                 255

Phe Glu Phe Arg Glu Ile Lys Glu Thr Ile Arg Leu Glu Met Glu Ser
            260                 265                 270

Thr Lys Asn Ser Ser Tyr Leu Asp Phe Phe Lys Ser Arg Gly Asn Arg
        275                 280                 285

Tyr Arg Leu Ala Ile Leu Leu Ser Leu Gly Phe Phe Ser Gln Trp Ser
    290                 295                 300

Gly Asn Ala Ile Ile Ser Asn Tyr Ser Ser Lys Leu Tyr Glu Thr Ala
305                 310                 315                 320

Gly Val Thr Asp Ser Thr Ala Lys Leu Gly Leu Ser Ala Gly Gln Thr
                325                 330                 335

Gly Leu Ala Leu Ile Val Ser Val Thr Met Ala Leu Leu Val Asp Lys
            340                 345                 350

Leu Gly Arg Arg Leu Ala Phe Leu Ala Ser Thr Gly Gly Met Cys Gly
        355                 360                 365

Thr Phe Val Ile Trp Thr Leu Thr Ala Gly Leu Tyr Gly Glu His Arg
    370                 375                 380

Leu Lys Gly Ala Asp Lys Ala Met Ile Phe Phe Ile Trp Val Phe Gly
385                 390                 395                 400

Ile Phe Tyr Ser Leu Ala Trp Ser Gly Leu Leu Val Gly Tyr Ala Ile
                405                 410                 415
```

-continued

```
Glu Ile Leu Pro Tyr Arg Leu Arg Gly Lys Gly Leu Met Val Met Asn
            420                 425                 430

Met Ser Val Gln Cys Ala Leu Thr Leu Asn Thr Tyr Ala Asn Pro Val
        435                 440                 445

Ala Phe Asp Tyr Phe Gly Pro Asp His Ser Trp Lys Leu Tyr Leu Ile
    450                 455                 460

Tyr Thr Cys Trp Ile Ala Ala Glu Phe Val Phe Val Phe Phe Met Tyr
465                 470                 475                 480

Val Glu Thr Lys Gly Pro Thr Leu Glu Glu Leu Ala Lys Val Ile Asp
                485                 490                 495

Gly Asp Glu Ala Asp Val Ala His Ile Asp Ile His Gln Val Glu Lys
            500                 505                 510

Glu Val Glu Ile His Glu His Glu Gly Lys Ser Val Ala
        515                 520                 525


<210> SEQ ID NO 40
<211> LENGTH: 1769
<212> TYPE: DNA
<213> ORGANISM: Artificial sequence
<220> FEATURE:
<223> OTHER INFORMATION: Synthesized: Cdt-2 (Neurospora crassa)

<400> SEQUENCE: 40

atgggcatct tcaacaagaa gcccgtggct caggccgtcg acctcaatca gatacaggag      60

gaggctcctc agtttgagag ggttgactgg aagaaggacc ccggtcttcg caagctctac     120

ttctacgcct tcattctttg cattgcttcg gccaccaccg gttacgatgg gtaaggggat     180

tcaagacatc caagaagcac aacctgctga cgctcatctc ccccacagca tgttcttcaa     240

ctcggtgcag aacttcgaga cctggattaa gtactttggc gacccgcgag gatccgagct     300

tggtctgctc ggtgctctct accagattgg ttccattggc tccatcccct ttgtgtaagt     360

cttcacgagg attgcaacac atggcagatt cgacgaaact gactcgatac cctcactata     420

cagccccctc cttaccgaca actttggccg caagaccccc atcatcatcg gctgcgttat     480

catgatcgtc ggtgccgttc tccaggccac ggccaagaac ctcgatacat tcatgggcgg     540

ccgtaccatg ctcggctttg gcaactccct cgcccagatc gcctccccca tgcttctcac     600

cgagctcgcc catcctcaac accgcgctcg tctcaccacc atctacaact gcttgtggaa     660

cgttggtgcc ctcgtcgtct cgtggttggc ctttggcacc aactacatca acaacgactg     720

gtcatggcgc attcccgcct tgctccaggc tttcccctcc atcattcagc tcctcggtat     780

ctggtgggtt cccgagtctc cccgtttcct catcgccaag gacaagcacg acgaggccct     840

ccacatcctc gccaagtacc acgccaacgg cgaccccaac caccccaccg tccagtttga     900

gttccgcgag atcaaggaga ccatccgcct cgagatggaa tcgaccaaga acagcagcta     960

cctcgacttc ttcaagagcc gcggcaaccg ctaccgcctc gccatcctcc tctcgctcgg    1020

cttcttctcc caatggtccg gcaacgccat catctccaac tactcctcca agctgtacga    1080

gaccgccggc gtcaccgact ccaccgccaa actcggtctt tccgccggac agaccggtct    1140

cgcgctcatc gtgtccgtca ccatggcgct gctcgtcgac aagctcggtc gtcgtcttgc    1200

tttcctcgct tccacgggcg gcatgtgcgg caccttttgtc atttggacgt tgacagccgg    1260

cctgtacggc gagcaccgcc tcaagggcgc cgacaaggcc atgatcttct ttatctgggt    1320

gttcggcatc ttctactcgc tcgcctggtc cgggttgctg gtcggctacg ccatcgaaat    1380

cctcccttac cgacttcgcg gcaaggggtt gatggtcatg aacatgtcgg tgcagtgcgc    1440
```

```
gctgacgctc aatacttatg cgaaccctgt tgcgtttgat tactttggtc ctgatcactc   1500

gtggaagctt tatcttattt acactgtgag cttttcatct cctttttttt tgttcttctg   1560

gcgcaacaaa tactaacagt agtgaaaagt gctggatcgc cgccgagttc gtcttcgtct   1620

tcttcatgta cgtcgagacc aagggcccca cgctcgagga gcttgccaag gtcattgatg   1680

gcgatgaggc cgatgttgcc cacatcgaca ttcaccaggt cgagaaggag gtggagattc   1740

acgagcatga gggcaagtct gttgcttga                                      1769
```

<210> SEQ ID NO 41
<211> LENGTH: 756
<212> TYPE: PRT
<213> ORGANISM: Artificial sequence
<220> FEATURE:
<223> OTHER INFORMATION: Synthesized: LVIS_0358 (Lactobacillus brevis)

<400> SEQUENCE: 41

```
Met Lys Arg Ile Phe Glu Val Gln Pro Trp Asn Val Ile Thr His Thr
1               5                   10                  15

Phe Asp Pro Lys Asp Lys Arg Leu Gln Glu Ser Met Thr Ser Leu Gly
            20                  25                  30

Asn Gly Tyr Met Gly Met Arg Gly Asp Phe Glu Glu Gly Tyr Ser Gly
        35                  40                  45

Asp Ser Leu Gln Gly Ile Tyr Leu Gly Gly Val Trp Tyr Pro Asp Lys
    50                  55                  60

Thr Arg Val Gly Trp Trp Lys Asn Gly Tyr Pro Lys Tyr Phe Gly Lys
65                  70                  75                  80

Val Val Asn Ala Val Asn Phe Ile Lys Leu Pro Ile Glu Ile Asn Gly
                85                  90                  95

Glu Pro Val Asp Leu Ala Lys Asp Lys Ile Ser Asp Phe Thr Leu Asp
            100                 105                 110

Leu Asp Met His Gln Gly Val Leu Asn Arg Ser Phe Val Val Glu Arg
        115                 120                 125

Gly Ser Val Arg Val Ala Leu Asn Phe Gln Arg Phe Leu Ser Val Ala
    130                 135                 140

Gln Pro Glu Leu Ser Val Gln Lys Val Thr Val Lys Asn Leu Ser Asp
145                 150                 155                 160

Ala Glu Val Asp Val Thr Leu Lys Pro Ser Ile Asp Ala Asp Val Met
                165                 170                 175

Asn Glu Glu Ala Asn Tyr Asp Glu Arg Phe Trp Asp Val Leu Ala Thr
            180                 185                 190

Asp Gln Gln Ala Asp Arg Gly Ser Ile Val Ala Lys Thr Thr Pro Asn
        195                 200                 205

Pro Phe Gly Thr Pro Arg Phe Thr Ser Gly Met Glu Met Arg Leu Val
    210                 215                 220

Thr Asp Leu Lys Asn Val Ala Ile Thr Gln Pro Asn Glu Lys Glu Val
225                 230                 235                 240

Thr Thr Ala Tyr Thr Gly Lys Leu Ala Pro Gln Ala Ser Ala Glu Leu
                245                 250                 255

Glu Lys Arg Val Ile Val Val Thr Ser Arg Asp Tyr Asp Thr Gln Glu
            260                 265                 270

Ser Leu Thr Ala Ala Met His Gln Leu Ser Asp Lys Val Ala Gln Ser
        275                 280                 285

Ser Tyr Glu Asp Leu Leu Asn Ala His Thr Val Ile Trp Ala Gln Arg
    290                 295                 300
```

-continued

```
Trp Glu Lys Ser Asp Val Val Ile Gln Gly Asp Asp Glu Ser Gln Gln
305                 310                 315                 320

Gly Ile Arg Phe Asn Leu Phe Gln Leu Phe Ser Thr Tyr Tyr Gly Asp
                325                 330                 335

Asp Ala Arg Leu Asn Ile Gly Pro Lys Gly Phe Thr Gly Glu Lys Tyr
            340                 345                 350

Gly Gly Ala Thr Tyr Trp Asp Thr Glu Ala Phe Ala Phe Pro Val Tyr
        355                 360                 365

Leu Gly Ile Thr Asp Pro Lys Val Thr Arg Asn Leu Leu Met Tyr Arg
    370                 375                 380

Tyr Lys Gln Leu Asp Gly Ala Tyr Ile Asn Ala Gln Glu Gln Gly Leu
385                 390                 395                 400

Lys Gly Ala Leu Phe Pro Met Val Thr Phe Asp Gly Ile Glu Cys His
                405                 410                 415

Asn Glu Trp Glu Ile Thr Phe Glu Glu Ile His Arg Asn Gly Asp Ile
            420                 425                 430

Ala Phe Ala Ile Tyr Asn Tyr Thr Arg Tyr Thr Gly Asp Asp Ser Tyr
        435                 440                 445

Val Leu His Glu Gly Ala Lys Val Leu Thr Glu Ile Ser Arg Phe Trp
    450                 455                 460

Ala Asp Arg Val His Phe Ser Lys Arg Asn Asn Gln Tyr Met Ile His
465                 470                 475                 480

Gly Val Thr Gly Ala Asp Glu Tyr Glu Asn Asn Val Asp Asn Asn Trp
                485                 490                 495

Asp Thr Asn Met Leu Ala Gln Trp Thr Leu Lys Tyr Thr Leu Glu Ile
            500                 505                 510

Leu Gly Lys Val Asp Gln Asn Thr Ala Lys Gln Leu Asp Val Ser Asp
        515                 520                 525

Glu Glu Lys Thr Lys Trp Gln Asp Ile Val Asp Arg Met Tyr Leu Pro
    530                 535                 540

Tyr Asp Lys Asp Leu Asn Ile Phe Val Gln His Asp Gly Phe Leu Asp
545                 550                 555                 560

Lys Asp Ile Glu Pro Val Ser Ser Ile Pro Ala Asp Gln Arg Pro Ile
                565                 570                 575

Asn Gln Asn Trp Ser Trp Asp Lys Ile Leu Arg Ser Pro Tyr Ile Lys
            580                 585                 590

Gln Gly Asp Val Leu Gln Gly Ile Trp Asp Phe Ile Asp Asp Tyr Thr
        595                 600                 605

Pro Glu Gln Lys Lys Ala Asn Phe Asp Phe Tyr Glu Pro Leu Thr Val
    610                 615                 620

His Glu Ser Ser Leu Ser Pro Ala Ile His Ser Val Leu Ala Ala Asp
625                 630                 635                 640

Leu His Tyr Glu Asp Lys Ala Val Glu Leu Tyr Ser Arg Thr Ala Arg
                645                 650                 655

Leu Asp Leu Asp Asn Tyr Asn Asn Asp Thr Thr Asp Gly Leu His Ile
            660                 665                 670

Thr Ala Met Thr Gly Gly Trp Ile Ala Val Val Gln Gly Phe Ala Gly
        675                 680                 685

Met Arg Val Arg Asp Gly Gln Leu His Tyr Ala Pro Phe Leu Pro Lys
    690                 695                 700

Thr Trp Thr Ser Tyr Thr Phe Arg Gln Val Phe Arg Asp Arg Leu Ile
705                 710                 715                 720

Glu Val Ser Val His Ala Asp Gly Pro His Phe Lys Leu Leu Ser Gly
```

725 730 735

Glu Pro Leu Thr Ile Asp Val Ala Gly Glu Lys Val Glu Leu Thr Gln
740 745 750

Asn Val Thr Ala
755

<210> SEQ ID NO 42
<211> LENGTH: 2271
<212> TYPE: DNA
<213> ORGANISM: Artificial sequence
<220> FEATURE:
<223> OTHER INFORMATION: Synthesized: LVIS_0358 (Lactobacillus brevis)

<400> SEQUENCE: 42
atgaaacgaa tttttgaggt ccaaccatgg aacgtaatta cgcatacttt tgaccccaaa 60
gacaaacgtc tccaagaatc catgaccagt ttaggtaatg gctacatggg gatgcggggt 120
gactttgaag aaggctatag tggcgattcc ctccaaggca tttacttggg tggtgtctgg 180
tatccagaca aaactcgggt tggttggtgg aagaatggct atccgaagta ctttggtaag 240
gtcgtcaatg ccgtcaactt tatcaagtta ccgattgaaa ttaacggtga acccgttgat 300
ttagcaaaag ataagatcag tgactttacc ttagaccttg atatgcatca gggtgttttg 360
aaccggtcat ttgttgttga acgcggttcg gttcgcgtag ccttgaattt ccaacgtttc 420
ttaagtgttg ctcagccaga attgtccgta caaaaagtaa cggtcaagaa cctgagcgat 480
gctgaggttg acgtgaccct aaagccaagt atcgatgccg atgtgatgaa cgaagaagct 540
aattacgatg aacgcttctg ggatgtcttg gccactgacc aacaggcaga tcgggggagt 600
atcgttgcca agaccacgcc taatccattt gggacacccc ggtttacttc cgggatggaa 660
atgcggttgg taacggactt aaagaacgtt gccatcacgc aaccaaatga aaaagaagtg 720
acgacggcgt ataccggtaa gctggcccca caggcaagcg ctgaattaga aaagcgcgtg 780
attgtggtaa cgtcacggga ttacgacaca caagaaagct taacggcagc catgcatcag 840
ttgagcgaca aagtggccca atcttcatat gaagacttgt tgaacgcaca cacggtcatc 900
tgggcccaac ggtgggaaaa atctgacgtt gtgatccaag gtgacgatga gtcacaacaa 960
ggaattcgct ttaacctgtt ccagttgttc tccacgtact acggtgacga tgcacgcttg 1020
aatatcggac ctaaaggctt tacgggcgag aaatatggtg gtgcaactta ctgggatacc 1080
gaagcctttg ctttccctgt ttatcttggg attactgatc ctaaggtcac gcgtaacctc 1140
ttgatgtacc gttacaagca attagacggt gcttacatca acgcacaaga acaagggctc 1200
aaaggggcct tgttcccaat ggtgaccttc gatgggattg aatgccataa tgaatgggaa 1260
atcaccttcg aagaaattca ccgaaatggt gatattgctt ttgccatcta caactacaca 1320
cgttacaccg gtgacgacag ttatgtcttg catgaagggg ccaaggtgct gaccgaaatt 1380
tctcggttct gggccgaccg ggttcacttc agtaagcgta ataaccagta tatgattcat 1440
ggggttacgg gcgctgatga gtatgaaaac aacgttgata acaactggga taccaacatg 1500
ttggctcagt ggacgttgaa gtacacacta gaaatattgg gtaaggttga tcagaatacc 1560
gccaagcaat tggatgtttc cgatgaggaa aagacgaagt ggcaagacat tgtcgatcgg 1620
atgtatctgc cttacgataa ggatctgaac atttttgttc aacacgatgg gttcttggat 1680
aaggatatcg aacccgtcag ctcgattcca gctgaccaac ggccaattaa ccaaaactgg 1740
tcgtgggata agatcttgcg gtcgccttac attaagcaag gggatgtctt gcaaggaatc 1800
tgggacttta ttgatgacta cacgccagaa caaaagaagg ccaactttga cttctacgaa 1860
ccactgacgg tgcacgaatc tagtttgtcc ccagcaatcc actcggtatt agctgctgac 1920
ttgcattatg aggataaggc cgtagaattg tactcacgga cggcacgact ggatttggat 1980
aactacaata atgacacgac agatggccta cacattacgg ccatgactgg tggctggatt 2040
gcggtagttc aaggtttcgc gggcatgcgg gttcgcgatg ggcagttgca ttatgcccca 2100
ttcttgccaa agacgtggac aagctacacc ttccggcaag tcttccgtga tcggctgatt 2160
gaagtcagcg ttcacgcaga tggccctcac ttcaagctac tcagtggcga accactgacg 2220
attgatgtgg ctggtgaaaa ggttgaatta acccaaaacg tgacagctta a 2271

<210> SEQ ID NO 43
<211> LENGTH: 753
<212> TYPE: PRT
<213> ORGANISM: Artificial sequence
<220> FEATURE:
<223> OTHER INFORMATION: Synthesized: mapA (Lactobacillus sanfranciscensis)

<400> SEQUENCE: 43

Met Lys Arg Ile Phe Glu Val Ser Pro Trp Thr Ile Thr Ser His Glu
1 5 10 15

Leu Gln Pro Ala Asp Lys Arg Leu Gln Glu Ser Met Thr Ser Leu Gly
20 25 30

Asn Glu Tyr Met Gly Met Arg Gly Met Phe Glu Glu Thr Tyr Ser Gly
35 40 45

Asp Ser Met Gln Gly Val Tyr Ile Gly Gly Val Trp Phe Pro Asp Lys
50 55 60

Thr Arg Val Gly Trp Trp Lys Ile Gly Tyr Pro Glu Tyr Phe Gly Lys
65 70 75 80

Ala Ile Asn Ala Leu Asn Phe Val Lys Ala Ile Ile Gln Ile Asp Gly
85 90 95

Val Thr Val Asp Leu Ala Thr Val Pro Tyr Thr Asp Phe Glu Val Thr
100 105 110

Leu Asp Met Gln Ala Gly Val Leu His Arg Gln Phe Thr Val Asn Gly
115 120 125

Val Arg Val Gln Val Asp Arg Phe Ile Ser Val Ala Thr Lys Glu Leu
130 135 140

Ala Asp Leu Arg Trp Ser Phe Thr Ala Ile Asp Gly Gln Thr His Asp
145 150 155 160

Val Gln Leu Thr Ala Leu Ile Asp Gly Asp Val Val Asn Glu Asp Ser
165 170 175

Asn Tyr Asp Glu Lys Phe Trp Asp Val Leu Asp Ala Glu Val Thr Asn
180 185 190

Asp Thr Ala Phe Leu Met Thr Arg Thr Val Pro Asn Pro Phe Gly Val
195 200 205

Pro Gln Phe Thr Val Ala Ala Gln Gln Arg Phe Val Ser Asp Leu Pro
210 215 220

Ala Ile Asp Val Val Gln Glu Asp Lys Gln Val Gly Asn Val Phe Ala
225 230 235 240

Gly Gln Val Gly Ala Val Thr Gln Arg Ile Glu Lys Arg Val Ile Val
245 250 255

Thr Thr Ser Arg Asp Tyr Ala Asp Asp Ala Ala Val Lys His Ala Thr
260 265 270

Asp Thr Ile Phe Ala Ser Ile Ala Ser Ala Thr Tyr Asp Asp Leu Tyr
275 280 285

```
Asp Ala His Thr Ala Gly Trp Ala Glu Arg Trp Glu Lys Ala Asp Val
    290                 295                 300

Gln Ile Thr Gly Asp Glu Ala Ala Gln Gln Gly Ile Arg Phe Asn Leu
305                 310                 315                 320

Phe Gln Leu Phe Ala Thr Tyr Tyr Gly Asn Asp Ala Arg Leu Asn Ile
                325                 330                 335

Gly Pro Lys Gly Phe Thr Gly Glu Lys Tyr Gly Gly Ala Thr Tyr Trp
            340                 345                 350

Asp Thr Glu Ala Phe Ala Ile Pro Val Tyr Leu Gly Val Thr Asp Pro
        355                 360                 365

Ala Val Val Lys Ser Leu Leu Lys Tyr Arg Tyr Gln Gln Ile Glu Gly
    370                 375                 380

Ala Tyr His Asn Ala Lys Gln Gln Asp Leu Ala Gly Ala Leu Phe Pro
385                 390                 395                 400

Met Val Thr Phe Asp Gly Ile Glu Ser His Asn Glu Trp Glu Ile Thr
                405                 410                 415

Phe Glu Glu Ile His Arg Asn Ser Ser Ile Ala Tyr Ala Ile Tyr Asn
            420                 425                 430

Tyr Thr His Leu Thr Gly Asp Arg Ser Trp Leu Glu Asn Glu Gly Ser
        435                 440                 445

Glu Val Leu Ile Gly Ile Ala Arg Phe Trp Ala Asp Arg Val His Tyr
    450                 455                 460

Ser Ala Arg Asn Asp Ala Tyr Met Ile His Gly Val Thr Gly Pro Asn
465                 470                 475                 480

Glu Tyr Glu Asn Asn Ile Asn Asn Asn Tyr Tyr Thr Asn Trp Met Ala
                485                 490                 495

Lys Trp Val Leu Ser Tyr Ala Leu Glu Asn Ile Asp Thr Val Ala Pro
            500                 505                 510

Glu Phe Gln Thr Lys Leu Asn Val Thr Ala Glu Glu Arg Lys His Trp
        515                 520                 525

Gln Glu Ile Val Asp Lys Met Tyr Leu Pro Glu Ala Asp Val Thr Asp
    530                 535                 540

Val Asn Gly Val Pro Arg His Val Phe Val Ala His Asp Thr Phe Leu
545                 550                 555                 560

Asp Lys Glu Leu Val Pro Val Arg Asp Leu Asp Pro Lys His Leu Pro
                565                 570                 575

Ile Asn Gln His Trp Ser Trp Asp Arg Val Leu Arg Ser Pro Tyr Ile
            580                 585                 590

Lys Gln Ser Asp Thr Leu His Ala Met Tyr Tyr Phe Pro Asp Ala Phe
        595                 600                 605

Thr Glu Gln Gln Lys Arg Asp Asn Tyr Glu Phe Tyr Glu Pro Phe Thr
    610                 615                 620

Val His Glu Ser Ser Leu Ser Pro Ser Val His Ser Ile Ile Ala Ala
625                 630                 635                 640

Asp Leu Lys Met Ala Asp Lys Ser Val Glu Phe Tyr Glu Arg Thr Ala
                645                 650                 655

Arg Leu Asp Leu Asp Asn Tyr Asn Asn Asp Thr Ser Asp Gly Leu His
            660                 665                 670

Ile Thr Ser Met Thr Gly Ala Trp Leu Ser Ile Val Gln Gly Phe Ala
        675                 680                 685

Gly Met Arg Val Arg Asp Asp Gln Leu His Phe Asp Pro Phe Leu Pro
    690                 695                 700
```

```
Asp Lys Trp Gln Gly Tyr Ser Phe Arg Phe Leu Phe Arg Gly Arg Leu
705                 710                 715                 720

Leu Ser Val Ala Val Asp Gln Asn Gly Ser His Val Glu Leu Leu Ser
                725                 730                 735

Gly Glu Pro Leu Thr Ile Asp Leu Ala Gly Glu Lys Leu Thr Leu Glu
            740                 745                 750

Ala


<210> SEQ ID NO 44
<211> LENGTH: 2262
<212> TYPE: DNA
<213> ORGANISM: Artificial sequence
<220> FEATURE:
<223> OTHER INFORMATION: Synthesized: mapA (Lactobacillus
      sanfranciscensis)

<400> SEQUENCE: 44

atgaagcgaa tttttgaagt tagtccttgg actattacct cgcatgagtt gcaaccagcg     60

gacaagcgtt tgcaagaatc aatgacgtca cttggaaatg agtatatggg gatgcggggc    120

atgtttgaag aaacatattc cggcgactct atgcaaggcg tttacattgg gggcgtttgg    180

ttccctgaca agacgcgtgt tggttggtgg aaaatcggct acccagagta cttcggtaag    240

gcgattaatg cgttgaattt tgtgaaagcg attattcaaa ttgatggggt cacggttgat    300

ttagcaacgg taccttacac tgattttgaa gtcactttgg atatgcaagc aggtgtcctg    360

caccgtcaat ttacggttaa cggtgtgcgg gtacaagtcg atcgcttcat ctcggttgcg    420

acgaaggaac tggctgattt gcggtggtca ttcacagcta ttgatgggca gacccacgat    480

gtgcagttga cggcattgat tgatggcgac gtcgtcaatg aggattcaaa ttatgatgaa    540

aaattctggg acgtgcttga tgcagaagta accaacgaca cggcgttctt aatgacgcga    600

actgtgccca atccatttgg tgtgccccaa tttacagtgg cggcccagca acgatttgtg    660

tcggatttgc cagcaattga tgttgtgcaa gaagacaaac aagttggaaa cgtttttgcg    720

ggtcaagttg gtgcggtaac acagcgcatt gaaaagcgtg tgattgtcac gacttcacgt    780

gattatgcag atgatgctgc tgttaagcat gcaactgaca ctatttttgc tagcattgca    840

tcagcaacct atgacgactt gtatgatgca cacacggctg gatgggcgga acgttgggaa    900

aaggccgacg ttcagattac tggtgacgaa gcggcccaac aaggcattcg cttcaactta    960

ttccaattat ttgccacgta ttatggtaac gatgcgcgtt tgaacatcgg accaaagggc   1020

ttcactggtg agaagtatgg tggtgcgacg tattgggata cggaagcatt tgccattcca   1080

gtttacctag ggttactga tccagctgtc gtgaagtcat tgttgaagta ccgttatcaa   1140

caaatcgaag ggcttacca caatgctaag caacaagact tggctggggc tttgttccca   1200

atggtgacct tcgatggtat cgaatcacac aacgagtggg aaattacgtt tgaagaaatc   1260

caccgtaatt cgtcgatcgc ctatgccatc tacaactaca cgcacttgac gggtgaccgt   1320

tcatggcttg aaaacgaggg tagtgaagtg ttgattggta tcgcacgctt ctgggctgac   1380

cgtgtgcact attcagcacg caacgatgcg tacatgattc acggtgttac cggaccaaac   1440

gagtacgaga acaacatcaa caacaactac tacactaact ggatggctaa gtgggtcttg   1500

tcatacgctt tggaaaacat cgacacggtt gcaccagagt tccaaacgaa gttgaacgtt   1560

acagctgaag aacgcaagca ctggcaagag attgtcgaca agatgtactt gcctgaagcg   1620

gacgttactg acgtcaacgg tgtgccacgt cacgtctttg ttgcgcacga cacattcttg   1680

gacaaggaat tggtaccagt ccgtgatttg gatccaaagc acttgccaat taaccaacac   1740
```

```
tggtcatggg accgtgtctt gcgttcacca tacatcaagc aatcagatac attgcacgcg   1800

atgtactact tcccagatgc ctttacggaa caacaaaagc gtgacaacta tgaattctat   1860

gagccattca cggtgcacga gtcatcattg tcaccatctg ttcactcaat tatcgctgct   1920

gacttgaaga tggccgataa gagtgtcgag ttctacgagc gtacagcacg tcttgacttg   1980

gataactaca acaacgacac gtcagacggg ttgcacatca cgtcaatgac gggtgcctgg   2040

ctatcaatcg tgcaaggatt tgctggcatg cgtgtccgcg atgatcaatt gcactttgac   2100

ccattcttgc ctgataagtg gcaaggctac agtttccgct tcctattccg cggtcgcttg   2160

ttgtcagtcg ctgttgacca aaacggttca cacgtcgaat tgttgtctgg tgagccattg   2220

acgattgatt tggctggtga aaagctaact ttggaggcct aa                      2262
```

<210> SEQ ID NO 45
<211> LENGTH: 504
<212> TYPE: PRT
<213> ORGANISM: Artificial sequence
<220> FEATURE:
<223> OTHER INFORMATION: Synthesized: Spl (Bifidobacterium adolescentis)

<400> SEQUENCE: 45

```
Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
                245                 250                 255

Pro Leu Leu Leu His Ala Leu Ser Thr Gly His Val Glu Pro Val Ala
            260                 265                 270
```

-continued

His Trp Thr Asp Ile Arg Pro Asn Asn Ala Val Thr Val Leu Asp Thr
        275                 280                 285

His Asp Gly Ile Gly Val Ile Asp Ile Gly Ser Asp Gln Leu Asp Arg
    290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335

Ala Ala Ser Asn Leu Asp Leu Tyr Gln Val Asn Ser Thr Tyr Tyr Ser
            340                 345                 350

Ala Leu Gly Cys Asn Asp Gln His Tyr Ile Ala Ala Arg Ala Val Gln
        355                 360                 365

Phe Phe Leu Pro Gly Val Pro Gln Val Tyr Tyr Val Gly Ala Leu Ala
    370                 375                 380

Gly Lys Asn Asp Met Glu Leu Leu Arg Lys Thr Asn Asn Gly Arg Asp
385                 390                 395                 400

Ile Asn Arg His Tyr Tyr Ser Thr Ala Glu Ile Asp Glu Asn Leu Lys
                405                 410                 415

Arg Pro Val Val Lys Ala Leu Asn Ala Leu Ala Lys Phe Arg Asn Glu
            420                 425                 430

Leu Asp Ala Phe Asp Gly Thr Phe Ser Tyr Thr Thr Asp Asp Asp Thr
        435                 440                 445

Ser Ile Ser Phe Thr Trp Arg Gly Glu Thr Ser Gln Ala Thr Leu Thr
    450                 455                 460

Phe Glu Pro Lys Arg Gly Leu Gly Val Asp Asn Thr Thr Pro Val Ala
465                 470                 475                 480

Met Leu Glu Trp Glu Asp Ser Ala Gly Asp His Arg Ser Asp Asp Leu
                485                 490                 495

Ile Ala Asn Pro Pro Val Val Ala
            500

<210> SEQ ID NO 46
<211> LENGTH: 1515
<212> TYPE: DNA
<213> ORGANISM: Artificial sequence
<220> FEATURE:
<223> OTHER INFORMATION: Synthesized: Spl (Bifidobacterium adolescentis)

<400> SEQUENCE: 46
atgaaaaaca aggtgcagct catcacttac gccgaccgcc ttggcgacgg caccatcaag 60
tcgatgaccg acattctgcg cacccgcttc gacggcgtgt acgacggcgt tcacatcctg 120
ccgttcttca ccccgttcga cggcgccgac gcaggcttcg acccgatcga ccacaccaag 180
gtcgacgaac gtctcggcag ctgggacgac gtcgccgaac tctccaagac ccacaacatc 240
atggtcgacg ccatcgtcaa ccacatgagt tgggaatcca agcagttcca ggacgtgctg 300
gccaagggcg aggagtccga atactatccg atgttcctca ccatgagctc cgtgttcccg 360
aacggcgcca ccgaagagga cctggccggc atctaccgtc cgcgtccggg cctgccgttc 420
acccactaca agttcgccgg caagacccgc ctcgtgtggg tcagcttcac cccgcagcag 480
gtggacatcg acaccgattc cgacaagggt tgggaatacc tcatgtcgat tttcgaccag 540
atggccgcct ctcacgtcag ctacatccgc ctcgacgccg tcggctatgg cgccaaggaa 600
gccggcacca gctgcttcat gaccccgaag accttcaagc tgatctcccg tctgcgtgag 660
gaaggcgtca agcgcggtct ggaaatcctc atcgaagtgc actcctacta caagaagcag 720

-continued

```
gtcgaaatcg catccaaggt ggaccgcgtc tacgacttcg ccctgcctcc gctgctgctg    780

cacgcgctga gcaccggcca cgtcgagccc gtcgcccact ggaccgacat acgcccgaac    840

aacgccgtca ccgtgctcga tacgcacgac ggcatcggcg tgatcgacat cggctccgac    900

cagctcgacc gctcgctcaa gggtctcgtg ccggatgagg acgtggacaa cctcgtcaac    960

accatccacg ccaacaccca cggcgaatcc caggcagcca ctggcgccgc cgcatccaat   1020

ctcgacctct accaggtcaa cagcacctac tattcggcgc tcgggtgcaa cgaccagcac   1080

tacatcgccg cccgcgcggt gcagttcttc ctgccgggcg tgccgcaagt ctactacgtc   1140

ggcgcgctcg ccggcaagaa cgacatggag ctgctgcgta agacgaataa cggccgcgac   1200

atcaatcgcc attactactc caccgcggaa atcgacgaga acctcaagcg tccggtcgtc   1260

aaggccctga acgcgctcgc caagttccgc aacgagctcg acgcgttcga cggcacgttc   1320

tcgtacacca ccgatgacga cacgtccatc agcttcacct ggcgcggcga aaccagccag   1380

gccacgctga cgttcgagcc gaagcgcggt ctcggtgtgg acaacactac gccggtcgcc   1440

atgttggaat gggaggattc cgcgggagac caccgttcgg atgatctgat cgccaatccg   1500

cctgtcgtcg cctga                                                    1515
```

```
<210> SEQ ID NO 47
<211> LENGTH: 490
<212> TYPE: PRT
<213> ORGANISM: Artificial sequence
<220> FEATURE:
<223> OTHER INFORMATION: Synthesized: SucP (Leuconostoc mesenteroides)

<400> SEQUENCE: 47

Met Glu Ile Gln Asn Lys Ala Met Leu Ile Thr Tyr Ala Asp Ser Leu
1               5                   10                  15

Gly Lys Asn Leu Lys Asp Val His Gln Val Leu Lys Glu Asp Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ala Asp Tyr Thr Arg Val Asp Ala Ala Phe
    50                  55                  60

Gly Asp Trp Ala Asp Val Glu Ala Leu Gly Glu Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Asp Ser Lys Tyr Lys Asp Phe Phe Ile
            100                 105                 110

Arg Trp Glu Lys Phe Trp Ala Lys Ala Gly Glu Asn Arg Pro Thr Gln
        115                 120                 125

Ala Asp Val Asp Leu Ile Tyr Lys Arg Lys Asp Lys Ala Pro Thr Gln
    130                 135                 140

Glu Ile Thr Phe Asp Asp Gly Thr Thr Glu Asn Leu Trp Asn Thr Phe
145                 150                 155                 160

Gly Glu Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
```

```
    210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
                245                 250                 255

Asp Phe Ala Leu Pro Met Thr Thr Leu Tyr Thr Leu Tyr Ser Gly Lys
            260                 265                 270

Thr Asn Gln Leu Ala Lys Trp Leu Lys Met Ser Pro Met Lys Gln Phe
        275                 280                 285

Thr Thr Leu Asp Thr His Asp Gly Ile Gly Val Val Asp Ala Arg Asp
    290                 295                 300

Ile Leu Thr Asp Asp Glu Ile Asp Tyr Ala Ser Glu Gln Leu Tyr Lys
305                 310                 315                 320

Val Gly Ala Asn Val Lys Lys Thr Tyr Ser Ser Ala Ser Tyr Asn Asn
                325                 330                 335

Leu Asp Ile Tyr Gln Ile Asn Ser Thr Tyr Tyr Ser Ala Leu Gly Asn
            340                 345                 350

Asp Asp Ala Ala Tyr Leu Leu Ser Arg Val Phe Gln Val Phe Ala Pro
        355                 360                 365

Gly Ile Pro Gln Ile Tyr Tyr Val Gly Leu Leu Ala Gly Glu Asn Asp
    370                 375                 380

Ile Ala Leu Leu Glu Ser Thr Lys Glu Gly Arg Asn Ile Asn Arg His
385                 390                 395                 400

Tyr Tyr Thr Arg Glu Glu Val Lys Ser Glu Val Lys Arg Pro Val Val
                405                 410                 415

Ala Asn Leu Leu Lys Leu Leu Ser Trp Arg Asn Glu Ser Pro Ala Phe
            420                 425                 430

Asp Leu Ala Gly Ser Ile Thr Val Asp Thr Pro Thr Asp Thr Thr Ile
        435                 440                 445

Val Val Thr Arg Gln Asp Glu Asn Gly Gln Asn Lys Ala Val Leu Thr
    450                 455                 460

Ala Asp Ala Ala Asn Lys Thr Phe Glu Ile Val Glu Asn Gly Gln Thr
465                 470                 475                 480

Val Met Ser Ser Asp Asn Leu Thr Gln Asn
                485                 490
```

<210> SEQ ID NO 48
<211> LENGTH: 1473
<212> TYPE: DNA
<213> ORGANISM: Artificial sequence
<220> FEATURE:
<223> OTHER INFORMATION: Synthesized: SucP (Leuconostoc mesenteroides)

<400> SEQUENCE: 48

```
atggaaattc aaaacaaagc aatgttgatc acttatgctg attcgttggg caaaaactta     60

aaagatgttc atcaagtctt gaaagaagat attggagatg cgattggtgg ggttcatttg    120

ttgcctttct tcccttcaac aggtgatcgc ggttttgcgc cagccgatta tactcgtgtt    180

gatgccgcat ttggtgattg ggcagatgtc gaagcattgg gtgaagaata ctatttgatg    240

tttgacttca tgattaacca tatttctcgt gaatcagtga tgtatcaaga ttttaagaag    300

aatcatgacg attcaaagta taaagatttc tttattcgtt gggaaaagtt ctgggcaaag    360

gccggcgaaa accgtccaac acaagccgat gttgacttaa tttacaagcg taaagataag    420

gcaccaacgc aagaaatcac ttttgatgat ggcacaacag aaaacttgtg gaatactttt    480
```

-continued

```
ggtgaagaac aaattgacat tgatgttaat tcagccattg ccaaggaatt tattaagaca    540

acccttgaag acatggtaaa acatggtgct aacttgattc gtttggatgc ctttgcgtat    600

gcagttaaaa aagttgacac aaatgacttc ttcgttgagc cagaaatctg ggacactttg    660

aatgaagtac gtgaaatttt gacaccatta aaggctgaaa ttttaccaga aattcatgaa    720

cattactcaa tccctaaaaa gatcaatgat catggttact tcacctatga ctttgcatta    780

ccaatgacaa cgctttacac attgtattca ggtaagacaa atcaattggc aaagtggttg    840

aagatgtcac caatgaagca attcacaaca ttggacacgc atgatggtat tggtgtcgtt    900

gatgcccgtg atattctaac tgatgatgaa attgactacg cttctgaaca actttacaag    960

gttggcgcga atgtcaaaaa gacatattca tctgcttcat acaacaacct tgatatttac   1020

caaattaact caacttatta ttcagcattg ggaaatgatg atgcagcata cttgttgagt   1080

cgtgtcttcc aagtctttgc gcctggaatt ccacaaattt attacgttgg tttgttggca   1140

ggtgaaaacg atatcgcgct tttggagtca actaaagaag gtcgtaatat taaccgtcat   1200

tactatacgc gtgaagaagt taagtcagaa gttaagcgac cagttgttgc taacttattg   1260

aagctattgt catggcgtaa tgaaagccct gcatttgatt tggctggctc aatcacagtt   1320

gacacgccaa ctgatacaac aattgtggtg acacgtcaag atgaaaatgg tcaaaacaaa   1380

gctgtattaa cagccgatgc ggccaacaaa acttttgaaa tcgttgagaa tggtcaaact   1440

gttatgagca gtgataattt gactcagaac taa                                1473
```

<210> SEQ ID NO 49
<211> LENGTH: 570
<212> TYPE: PRT
<213> ORGANISM: Artificial sequence
<220> FEATURE:
<223> OTHER INFORMATION: Synthesized: PGM1 (Saccharomyces cerevisiae)

<400> SEQUENCE: 49

```
Met Ser Leu Leu Ile Asp Ser Val Pro Thr Val Ala Tyr Lys Asp Gln
1               5                   10                  15

Lys Pro Gly Thr Ser Gly Leu Arg Lys Lys Thr Lys Val Phe Met Asp
            20                  25                  30

Glu Pro His Tyr Thr Glu Asn Phe Ile Gln Ala Thr Met Gln Ser Ile
        35                  40                  45

Pro Asn Gly Ser Glu Gly Thr Thr Leu Val Val Gly Gly Asp Gly Arg
    50                  55                  60

Phe Tyr Asn Asp Val Ile Met Asn Lys Ile Ala Ala Val Gly Ala Ala
65                  70                  75                  80

Asn Gly Val Arg Lys Leu Val Ile Gly Gln Gly Gly Leu Leu Ser Thr
                85                  90                  95

Pro Ala Ala Ser His Ile Ile Arg Thr Tyr Glu Glu Lys Cys Thr Gly
            100                 105                 110

Gly Gly Ile Ile Leu Thr Ala Ser His Asn Pro Gly Gly Pro Glu Asn
        115                 120                 125

Asp Leu Gly Ile Lys Tyr Asn Leu Pro Asn Gly Gly Pro Ala Pro Glu
    130                 135                 140

Ser Val Thr Asn Ala Ile Trp Glu Ala Ser Lys Lys Leu Thr His Tyr
145                 150                 155                 160

Lys Ile Ile Lys Asn Phe Pro Lys Leu Asn Leu Asn Lys Leu Gly Lys
                165                 170                 175

Asn Gln Lys Tyr Gly Pro Leu Leu Val Asp Ile Ile Asp Pro Ala Lys
            180                 185                 190
```

```
Ala Tyr Val Gln Phe Leu Lys Glu Ile Phe Asp Phe Asp Leu Ile Lys
        195                 200                 205

Ser Phe Leu Ala Lys Gln Arg Lys Asp Lys Gly Trp Lys Leu Leu Phe
    210                 215                 220

Asp Ser Leu Asn Gly Ile Thr Gly Pro Tyr Gly Lys Ala Ile Phe Val
225                 230                 235                 240

Asp Glu Phe Gly Leu Pro Ala Glu Glu Val Leu Gln Asn Trp His Pro
                245                 250                 255

Leu Pro Asp Phe Gly Gly Leu His Pro Asp Pro Asn Leu Thr Tyr Ala
            260                 265                 270

Arg Thr Leu Val Asp Arg Val Asp Arg Glu Lys Ile Ala Phe Gly Ala
        275                 280                 285

Ala Ser Asp Gly Asp Gly Asp Arg Asn Met Ile Tyr Gly Tyr Gly Pro
    290                 295                 300

Ala Phe Val Ser Pro Gly Asp Ser Val Ala Ile Ile Ala Glu Tyr Ala
305                 310                 315                 320

Pro Glu Ile Pro Tyr Phe Ala Lys Gln Gly Ile Tyr Gly Leu Ala Arg
                325                 330                 335

Ser Phe Pro Thr Ser Ser Ala Ile Asp Arg Val Ala Ala Lys Lys Gly
            340                 345                 350

Leu Arg Cys Tyr Glu Val Pro Thr Gly Trp Lys Phe Phe Cys Ala Leu
        355                 360                 365

Phe Asp Ala Lys Lys Leu Ser Ile Cys Gly Glu Glu Ser Phe Gly Thr
    370                 375                 380

Gly Ser Asn His Ile Arg Glu Lys Asp Gly Leu Trp Ala Ile Ile Ala
385                 390                 395                 400

Trp Leu Asn Ile Leu Ala Ile Tyr His Arg Arg Asn Pro Glu Lys Glu
                405                 410                 415

Ala Ser Ile Lys Thr Ile Gln Asp Glu Phe Trp Asn Glu Tyr Gly Arg
            420                 425                 430

Thr Phe Phe Thr Arg Tyr Asp Tyr Glu His Ile Glu Cys Glu Gln Ala
        435                 440                 445

Glu Lys Val Val Ala Leu Leu Ser Glu Phe Val Ser Arg Pro Asn Val
    450                 455                 460

Cys Gly Ser His Phe Pro Ala Asp Glu Ser Leu Thr Val Ile Asp Cys
465                 470                 475                 480

Gly Asp Phe Ser Tyr Arg Asp Leu Asp Gly Ser Ile Ser Glu Asn Gln
                485                 490                 495

Gly Leu Phe Val Lys Phe Ser Asn Gly Thr Lys Phe Val Leu Arg Leu
            500                 505                 510

Ser Gly Thr Gly Ser Ser Gly Ala Thr Ile Arg Leu Tyr Val Glu Lys
        515                 520                 525

Tyr Thr Asp Lys Lys Glu Asn Tyr Gly Gln Thr Ala Asp Val Phe Leu
    530                 535                 540

Lys Pro Val Ile Asn Ser Ile Val Lys Phe Leu Arg Phe Lys Glu Ile
545                 550                 555                 560

Leu Gly Thr Asp Glu Pro Thr Val Arg Thr
                565                 570
```

<210> SEQ ID NO 50
<211> LENGTH: 1713
<212> TYPE: DNA
<213> ORGANISM: Artificial sequence
<220> FEATURE:

<223> OTHER INFORMATION: Synthesized: PGM1 (Saccharomyces cerevisiae)

<400> SEQUENCE: 50
atgtcacttc taatagattc tgtaccaaca gttgcttata aggaccaaaa accgggtact 60
tcaggtttac gtaagaagac caaggttttc atggatgagc ctcattatac tgagaacttc 120
attcaagcaa caatgcaatc tatccctaat ggctcagagg gaaccacttt agttgttgga 180
ggagatggtc gtttctacaa cgatgttatc atgaacaaga ttgccgcagt aggtgctgca 240
aacggtgtca gaaagttagt cattggtcaa ggcggtttac tttcaacacc agctgcttct 300
catataatta gaacatacga ggaaaagtgt accggtggtg gtatcatatt aactgcctca 360
cacaacccag gcggtccaga gaatgattta ggtatcaagt ataatttacc taatggtggg 420
ccagctccag agagtgtcac taacgctatc tgggaagcgt ctaaaaaatt aactcactat 480
aaaattataa agaacttccc caagttgaat ttgaacaagc ttggtaaaaa ccaaaaatat 540
ggcccattgt tagtggacat aattgatcct gccaaagcat acgttcaatt tctgaaggaa 600
atttttgatt ttgacttaat taaaagcttc ttagcgaaac agcgcaaaga caaagggtgg 660
aagttgttgt ttgactcctt aaatggtatt acaggaccat atggtaaggc tatatttgtt 720
gatgaatttg gtttaccggc agaggaagtt cttcaaaatt ggcacccttt acctgatttc 780
ggcggtttac atcccgatcc gaatctaacc tatgcacgaa ctcttgttga cagggttgac 840
cgcgaaaaaa ttgcctttgg agcagcctcc gatggtgatg gtgataggaa tatgatttac 900
ggttatggcc ctgctttcgt ttcgccaggt gattctgttg ccattattgc cgaatatgca 960
cccgaaattc catacttcgc caaacaaggt atttatggct tggcacgttc atttcctaca 1020
tcctcagcca ttgatcgtgt tgcagcaaaa aagggattaa gatgttacga agttccaacc 1080
ggctggaaat tcttctgtgc cttatttgat gctaaaaagc tatcaatctg tggtgaagaa 1140
tccttcggta caggttccaa tcatatcaga gaaaaggacg gtctatgggc cattattgct 1200
tggttaaata tcttggctat ctaccatagg cgtaaccctg aaaaggaagc ttcgatcaaa 1260
actattcagg acgaattttg gaacgagtat ggccgtactt tcttcacaag atacgattac 1320
gaacatatcg aatgcgagca ggccgaaaaa gttgtagctc ttttgagtga atttgtatca 1380
aggccaaacg tttgtggctc ccacttccca gctgatgagt ctttaaccgt tatcgattgt 1440
ggtgattttt cgtatagaga tctagatggc tccatctctg aaaatcaagg ccttttcgta 1500
aagttttcga atgggactaa atttgttttg aggttatccg gcacaggcag ttctggtgca 1560
acaataagat tatacgtaga aaagtatact gataaaaagg agaactatgg ccaaacagct 1620
gacgtcttct tgaaacccgt catcaactcc attgtaaaat tcttaagatt taaagaaatt 1680
ttaggaacag acgaaccaac agtccgcaca tag 1713

<210> SEQ ID NO 51
<211> LENGTH: 811
<212> TYPE: PRT
<213> ORGANISM: Artificial sequence
<220> FEATURE:
<223> OTHER INFORMATION: Synthesized: Cbp (Clostridium thermocellum)

<400> SEQUENCE: 51

Met Lys Phe Gly Phe Phe Asp Asp Ala Asn Lys Glu Tyr Val Ile Thr
1 5 10 15

Val Pro Arg Thr Pro Tyr Pro Trp Ile Asn Tyr Leu Gly Thr Glu Asn
20 25 30

Phe Phe Ser Leu Ile Ser Asn Thr Ala Gly Gly Tyr Cys Phe Tyr Arg

-continued

```
        35                  40                  45

Asp Ala Arg Leu Arg Arg Ile Thr Arg Tyr Arg Tyr Asn Asn Val Pro
    50                  55                  60

Ile Asp Met Gly Gly Arg Tyr Phe Tyr Ile Tyr Asp Asn Gly Asp Phe
65                  70                  75                  80

Trp Ser Pro Gly Trp Ser Pro Val Lys Arg Glu Leu Glu Ser Tyr Glu
                85                  90                  95

Cys Arg His Gly Leu Gly Tyr Thr Lys Ile Ala Gly Lys Arg Asn Gly
            100                 105                 110

Ile Lys Ala Glu Val Thr Phe Phe Val Pro Leu Asn Tyr Asn Gly Glu
        115                 120                 125

Val Gln Lys Leu Ile Leu Lys Asn Glu Gly Gln Asp Lys Lys Lys Ile
    130                 135                 140

Thr Leu Phe Ser Phe Ile Glu Phe Cys Leu Trp Asn Ala Tyr Asp Asp
145                 150                 155                 160

Met Thr Asn Phe Gln Arg Asn Phe Ser Thr Gly Glu Val Glu Ile Glu
                165                 170                 175

Gly Ser Val Ile Tyr His Lys Thr Glu Tyr Arg Glu Arg Arg Asn His
            180                 185                 190

Tyr Ala Phe Tyr Ser Val Asn Ala Lys Ile Ser Gly Phe Asp Ser Asp
        195                 200                 205

Arg Asp Ser Phe Ile Gly Leu Tyr Asn Gly Phe Asp Ala Pro Gln Ala
    210                 215                 220

Val Val Asn Gly Lys Ser Asn Asn Ser Val Ala Asp Gly Trp Ala Pro
225                 230                 235                 240

Ile Ala Ser His Ser Ile Glu Ile Glu Leu Asn Pro Gly Glu Gln Lys
                245                 250                 255

Glu Tyr Val Phe Ile Ile Gly Tyr Val Glu Asn Lys Asp Glu Glu Lys
            260                 265                 270

Trp Glu Ser Lys Gly Val Ile Asn Lys Lys Lys Ala Tyr Glu Met Ile
        275                 280                 285

Glu Gln Phe Asn Thr Val Glu Lys Val Asp Lys Ala Phe Glu Glu Leu
    290                 295                 300

Lys Ser Tyr Trp Asn Ala Leu Leu Ser Lys Tyr Phe Leu Glu Ser His
305                 310                 315                 320

Asp Glu Lys Leu Asn Arg Met Val Asn Ile Trp Asn Gln Tyr Gln Cys
                325                 330                 335

Met Val Thr Phe Asn Met Ser Arg Ser Ala Ser Tyr Phe Glu Ser Gly
            340                 345                 350

Ile Gly Arg Gly Met Gly Phe Arg Asp Ser Asn Gln Asp Leu Leu Gly
        355                 360                 365

Phe Val His Gln Ile Pro Glu Arg Ala Arg Glu Arg Leu Leu Asp Leu
    370                 375                 380

Ala Ala Thr Gln Leu Glu Asp Gly Ser Ala Tyr His Gln Tyr Gln Pro
385                 390                 395                 400

Leu Thr Lys Lys Gly Asn Asn Glu Ile Gly Ser Asn Phe Asn Asp Asp
                405                 410                 415

Pro Leu Trp Leu Ile Leu Ala Thr Ala Ala Tyr Ile Lys Glu Thr Gly
            420                 425                 430

Asp Tyr Ser Ile Leu Lys Glu Gln Val Pro Phe Asn Asn Asp Pro Ser
        435                 440                 445

Lys Ala Asp Thr Met Phe Glu His Leu Thr Arg Ser Phe Tyr His Val
    450                 455                 460
```

```
Val Asn Asn Leu Gly Pro His Gly Leu Pro Leu Ile Gly Arg Ala Asp
465                 470                 475                 480

Trp Asn Asp Cys Leu Asn Leu Asn Cys Phe Ser Thr Val Pro Asp Glu
                485                 490                 495

Ser Phe Gln Thr Thr Thr Ser Lys Asp Gly Lys Val Ala Glu Ser Val
            500                 505                 510

Met Ile Ala Gly Met Phe Val Phe Ile Gly Lys Asp Tyr Val Lys Leu
        515                 520                 525

Cys Glu Tyr Met Gly Leu Glu Glu Glu Ala Arg Lys Ala Gln Gln His
    530                 535                 540

Ile Asp Ala Met Lys Glu Ala Ile Leu Lys Tyr Gly Tyr Asp Gly Glu
545                 550                 555                 560

Trp Phe Leu Arg Ala Tyr Asp Asp Phe Gly Arg Lys Val Gly Ser Lys
                565                 570                 575

Glu Asn Glu Glu Gly Lys Ile Phe Ile Glu Ser Gln Gly Phe Cys Val
            580                 585                 590

Met Ala Glu Ile Gly Leu Glu Asp Gly Lys Ala Leu Lys Ala Leu Asp
        595                 600                 605

Ser Val Lys Lys Tyr Leu Asp Thr Pro Tyr Gly Leu Val Leu Gln Asn
    610                 615                 620

Pro Ala Phe Thr Arg Tyr Tyr Ile Glu Tyr Gly Glu Ile Ser Thr Tyr
625                 630                 635                 640

Pro Pro Gly Tyr Lys Glu Asn Ala Gly Ile Phe Cys His Asn Asn Ala
                645                 650                 655

Trp Ile Ile Cys Ala Glu Thr Val Val Gly Arg Gly Asp Met Ala Phe
            660                 665                 670

Asp Tyr Tyr Arg Lys Ile Ala Pro Ala Tyr Ile Glu Asp Val Ser Asp
        675                 680                 685

Ile His Lys Leu Glu Pro Tyr Val Tyr Ala Gln Met Val Ala Gly Lys
    690                 695                 700

Asp Ala Lys Arg His Gly Glu Ala Lys Asn Ser Trp Leu Thr Gly Thr
705                 710                 715                 720

Ala Ala Trp Asn Phe Val Ala Ile Ser Gln Trp Ile Leu Gly Val Lys
                725                 730                 735

Pro Asp Tyr Asp Gly Leu Lys Ile Asp Pro Cys Ile Pro Lys Ala Trp
            740                 745                 750

Asp Gly Tyr Lys Val Thr Arg Tyr Phe Arg Gly Ser Thr Tyr Glu Ile
        755                 760                 765

Thr Val Lys Asn Pro Asn His Val Ser Lys Gly Val Ala Lys Ile Thr
    770                 775                 780

Val Asp Gly Asn Glu Ile Ser Gly Asn Ile Leu Pro Val Phe Asn Asp
785                 790                 795                 800

Gly Lys Thr His Lys Val Glu Val Ile Met Gly
                805                 810
```

<210> SEQ ID NO 52
<211> LENGTH: 2436
<212> TYPE: DNA
<213> ORGANISM: Artificial sequence
<220> FEATURE:
<223> OTHER INFORMATION: Synthesized: Cbp (Clostridium thermocellum)

<400> SEQUENCE: 52

```
atgaagttcg gttttttga tgatgcaaac aaagagtacg ttattaccgt gcccaggaca     60
```

-continued

```
ccgtatccgt ggataaacta cctgggtaca gagaatttct tctcactcat ttcgaatacc    120
gcaggcggat attgctttta cagggatgca aggcttagac gtataacaag atacagatac    180
aacaatgttc ctattgacat gggaggacgt tatttctaca tatatgacaa cggtgatttc    240
tggtcgccgg gatggtctcc ggtaaaaagg gagcttgaaa gctatgaatg cagacatgga    300
ctgggatata caaaaattgc cggtaaaaga aacggaataa aagcggaggt cactttcttc    360
gttccgttaa actacaatgg tgaagtccaa aagcttatat tgaagaatga aggacaggac    420
aaaaagaaaa taactctctt ctcttttatt gagttctgct tgtggaatgc ttatgatgat    480
atgaccaact tccagagaaa cttcagcacc ggtgaagttg agattgaagg ctcggttatc    540
tatcacaaga cagagtacag agagcgcaga aaccattacg cattctattc tgtaaatgca    600
aaaatcagcg gatttgacag tgacagagac agcttcatag gactttacaa cggttttgac    660
gctcctcagg ctgtagtgaa cggcaagtca aacaattccg ttgcggacgg atgggcaccg    720
attgcgtccc acagcattga aattgaattg aatcccgggg agcaaaagga atatgtattt    780
attataggtt atgtggagaa caaagatgaa gaaaaatggg agtcaaaagg tgtcatcaac    840
aagaaaaaag cttatgaaat gatagagcag ttcaacactg ttgaaaaggt tgacaaagca    900
tttgaagaac tcaagagcta ttggaatgct cttctttcaa aatactttct tgaaagccac    960
gatgaaaaac tcaaccgtat ggttaatata tggaatcagt accagtgtat ggttacattc   1020
aacatgtcaa gaagcgcttc atactttgaa tccggtatcg gaagaggtat gggtttcaga   1080
gattcaaacc aggacttgct gggatttgta caccagatac ccgaaagagc aagagaaagg   1140
cttcttgacc tggctgcaac tcagcttgaa gatggcagtg cgtaccatca gtatcagcct   1200
cttaccaaaa aaggtaacaa tgaaatcgga agcaacttca acgatgaccc gttgtggctg   1260
attcttgcaa ctgctgcata tattaaggaa accggtgatt attcaatact gaaggagcaa   1320
gttccgttca acaatgatcc gtccaaagcc gacaccatgt ttgaacattt gacccgttcc   1380
ttctaccatg tggtaaacaa ccttggacct cacggattgc cgcttatagg tagggcggac   1440
tggaatgact gccttaactt aaactgcttc tccaccgttc cggatgagtc gttccagacc   1500
acaacaagca aagacggaaa agtggcagag tcagttatga ttgccggaat gtttgtgttc   1560
atcggaaaag actatgtgaa gctttgcgaa tacatgggcc ttgaagagga agccaggaaa   1620
gctcagcagc atattgacgc aatgaaggaa gcaattctca aatacggtta tgacggtgag   1680
tggttcttaa gagcttacga cgactttgga agaaaagtcg gaagcaaaga aaacgaagag   1740
ggtaagattt tcattgagtc tcagggattc tgtgtaatgg ctgaaatcgg gcttgaagac   1800
ggcaaggctt tgaaggctct ggattctgtc aagaaatatc ttgacactcc atatggtctt   1860
gtacttcaaa atcccgcgtt tacaagatac tatattgagt acggagaaat ttcaacatat   1920
ccaccgggat acaaagaaaa tgccggtata ttctgccaca acaatgcatg gataatctgt   1980
gctgaaacgg ttgtcggaag aggagacatg gcgtttgatt actatagaaa aatagcacct   2040
gcttatattg aagatgtaag tgacatccac aagcttgagc cttatgttta tgcacagatg   2100
gttgccggaa aagacgcaaa acgccatgga gaagctaaga actcatggct gaccggtact   2160
gcggcgtgga actttgtggc gatttcacag tggatactgg gtgtaaaacc tgactatgac   2220
ggattgaaga ttgatccatg catacccaag gcatgggacg gatacaaagt taccagatat   2280
ttcagaggct caacttatga aatcactgtg aagaatccga accatgtatc aaaaggtgtg   2340
gctaaaatta ctgttgacgg caatgaaatc agcggaaata ttcttccggt gttcaatgac   2400
ggaaagactc acaaagttga agtaattatg ggataa                             2436
```

<210> SEQ ID NO 53
<211> LENGTH: 569
<212> TYPE: PRT
<213> ORGANISM: Artificial sequence
<220> FEATURE:
<223> OTHER INFORMATION: Synthesized: PGM2 (Saccharomyces cerevisiae)

<400> SEQUENCE: 53

```
Met Ser Phe Gln Ile Glu Thr Val Pro Thr Lys Pro Tyr Glu Asp Gln
1               5                   10                  15

Lys Pro Gly Thr Ser Gly Leu Arg Lys Lys Thr Lys Val Phe Lys Asp
            20                  25                  30

Glu Pro Asn Tyr Thr Glu Asn Phe Ile Gln Ser Ile Met Glu Ala Ile
        35                  40                  45

Pro Glu Gly Ser Lys Gly Ala Thr Leu Val Val Gly Gly Asp Gly Arg
    50                  55                  60

Tyr Tyr Asn Asp Val Ile Leu His Lys Ile Ala Ala Ile Gly Ala Ala
65                  70                  75                  80

Asn Gly Ile Lys Lys Leu Val Ile Gly Gln His Gly Leu Leu Ser Thr
                85                  90                  95

Pro Ala Ala Ser His Ile Met Arg Thr Tyr Glu Glu Lys Cys Thr Gly
            100                 105                 110

Gly Ile Ile Leu Thr Ala Ser His Asn Pro Gly Gly Pro Glu Asn Asp
        115                 120                 125

Met Gly Ile Lys Tyr Asn Leu Ser Asn Gly Gly Pro Ala Pro Glu Ser
    130                 135                 140

Val Thr Asn Ala Ile Trp Glu Ile Ser Lys Lys Leu Thr Ser Tyr Lys
145                 150                 155                 160

Ile Ile Lys Asp Phe Pro Glu Leu Asp Leu Gly Thr Ile Gly Lys Asn
                165                 170                 175

Lys Lys Tyr Gly Pro Leu Leu Val Asp Ile Ile Asp Ile Thr Lys Asp
            180                 185                 190

Tyr Val Asn Phe Leu Lys Glu Ile Phe Asp Phe Asp Leu Ile Lys Lys
        195                 200                 205

Phe Ile Asp Asn Gln Arg Ser Thr Lys Asn Trp Lys Leu Leu Phe Asp
    210                 215                 220

Ser Met Asn Gly Val Thr Gly Pro Tyr Gly Lys Ala Ile Phe Val Asp
225                 230                 235                 240

Glu Phe Gly Leu Pro Ala Asp Glu Val Leu Gln Asn Trp His Pro Ser
                245                 250                 255

Pro Asp Phe Gly Gly Met His Pro Asp Pro Asn Leu Thr Tyr Ala Ser
            260                 265                 270

Ser Leu Val Lys Arg Val Asp Arg Glu Lys Ile Glu Phe Gly Ala Ala
        275                 280                 285

Ser Asp Gly Asp Gly Asp Arg Asn Met Ile Tyr Gly Tyr Gly Pro Ser
    290                 295                 300

Phe Val Ser Pro Gly Asp Ser Val Ala Ile Ile Ala Glu Tyr Ala Ala
305                 310                 315                 320

Glu Ile Pro Tyr Phe Ala Lys Gln Gly Ile Tyr Gly Leu Ala Arg Ser
                325                 330                 335

Phe Pro Thr Ser Gly Ala Ile Asp Arg Val Ala Lys Ala His Gly Leu
            340                 345                 350

Asn Cys Tyr Glu Val Pro Thr Gly Trp Lys Phe Phe Cys Ala Leu Phe
        355                 360                 365
```

```
Asp Ala Lys Lys Leu Ser Ile Cys Gly Glu Glu Ser Phe Gly Thr Gly
    370                 375                 380

Ser Asn His Val Arg Glu Lys Asp Gly Val Trp Ala Ile Met Ala Trp
385                 390                 395                 400

Leu Asn Ile Leu Ala Ile Tyr Asn Lys His His Pro Glu Asn Glu Ala
                405                 410                 415

Ser Ile Lys Thr Ile Gln Asn Glu Phe Trp Ala Lys Tyr Gly Arg Thr
            420                 425                 430

Phe Phe Thr Arg Tyr Asp Phe Glu Lys Val Glu Thr Glu Lys Ala Asn
        435                 440                 445

Lys Ile Val Asp Gln Leu Arg Ala Tyr Val Thr Lys Ser Gly Val Val
    450                 455                 460

Asn Ser Ala Phe Pro Ala Asp Glu Ser Leu Lys Val Thr Asp Cys Gly
465                 470                 475                 480

Asp Phe Ser Tyr Thr Asp Leu Asp Gly Ser Val Ser Asp His Gln Gly
                485                 490                 495

Leu Tyr Val Lys Leu Ser Asn Gly Ala Arg Phe Val Leu Arg Leu Ser
            500                 505                 510

Gly Thr Gly Ser Ser Gly Ala Thr Ile Arg Leu Tyr Ile Glu Lys Tyr
        515                 520                 525

Cys Asp Asp Lys Ser Gln Tyr Gln Lys Thr Ala Glu Glu Tyr Leu Lys
    530                 535                 540

Pro Ile Ile Asn Ser Val Ile Lys Phe Leu Asn Phe Lys Gln Val Leu
545                 550                 555                 560

Gly Thr Glu Glu Pro Thr Val Arg Thr
                565
```

```
<210> SEQ ID NO 54
<211> LENGTH: 1710
<212> TYPE: DNA
<213> ORGANISM: Artificial sequence
<220> FEATURE:
<223> OTHER INFORMATION: Synthesized: PGM2 (Saccharomyces cerevisiae)

<400> SEQUENCE: 54

atgtcatttc aaattgaaac ggttcccacc aaaccatatg aagaccaaaa gcctggtacc      60

tctggtttgc gtaagaagac aaaggtgttt aaagacgaac ctaactacac agaaaatttc     120

attcaatcga tcatggaagc tattccagag ggttctaaag gtgccactct tgttgtcggt     180

ggtgatgggc gttactacaa tgatgtcatt cttcataaga ttgccgctat cggtgctgcc     240

aacggtatta aaaagttagt tattggtcag catggtcttc tgtctacgcc agccgcttct     300

cacatcatga gaacctacga ggaaaaatgt actggtggta ttatcttaac cgcctcacat     360

aatccaggtg gtccagaaaa tgacatgggt attaagtata acttatccaa tgggggtcct     420

gctcctgaat ccgtcacaaa tgctatttgg gagatttcca aaaagcttac cagctataag     480

attatcaaag acttcccaga actagacttg ggtacgatag gcaagaacaa gaaatacggt     540

ccattactcg ttgacattat cgatattaca aaagattatg tcaacttctt gaaggaaatc     600

ttcgatttcg acttaatcaa gaaattcatc gataatcaac gttctactaa gaattggaag     660

ttactgtttg acagtatgaa cggtgtaact ggaccatacg gtaaggctat tttcgttgat     720

gaatttggtt taccggcgga tgaggtttta caaaactggc atccttctcc ggattttggt     780

ggtatgcatc cagatccaaa cttaacttat gccagttcgt tagtgaaaag agtagatcgt     840

gaaaagattg agtttggtgc tgcatccgat ggtgatggtg atagaaatat gatttacggt     900
```

```
tacggcccat ctttcgtttc tccaggtgac tccgtcgcaa ttattgccga atatgcagct    960

gaaattccat atttcgccaa gcaaggtata tatggtctgg cccgttcatt ccctacctca   1020

ggagccatag accgtgttgc caaggcccat ggtctaaact gttatgaggt cccaactggc   1080

tggaaatttt tctgtgcttt gttcgacgct aaaaaattat ctatctgtgg tgaagaatcg   1140

tttggtactg gttccaacca cgtaagggaa aaggacggtg tttgggccat tatggcgtgg   1200

ttgaacatct tggccattta caacaagcat catccggaga acgaagcttc tattaagacg   1260

atacagaatg aattctgggc aaagtacggc cgtactttct tcactcgtta tgattttgaa   1320

aaagttgaaa cagaaaaagc taacaagatt gtcgatcaat tgagagcata tgttaccaaa   1380

tcgggtgttg ttaattccgc cttcccagcc gatgagtctc ttaaggtcac cgattgtggt   1440

gatttttcat acacagattt ggacggttct gtttctgacc atcaaggttt atatgtcaag   1500

ctttccaatg gtgcaagatt cgttctaaga ttgtcaggta caggttcttc aggtgctacc   1560

attagattgt acattgaaaa atactgcgat gataaatcac aataccaaaa gacagctgaa   1620

gaatacttga agccaattat taactcggtc atcaagttct tgaactttaa acaagtttta   1680

ggaactgaag aaccaacggt tcgtacttaa                                    1710


<210> SEQ ID NO 55
<211> LENGTH: 223
<212> TYPE: PRT
<213> ORGANISM: Artificial sequence
<220> FEATURE:
<223> OTHER INFORMATION: Synthesized: pgmA (Lactobacillus
      sanfranciscensis)

<400> SEQUENCE: 55

Met Thr Lys Phe Ser Glu Ile Lys Gly Phe Ala Phe Asp Leu Asp Gly
1               5                   10                  15

Val Ile Thr Asp Thr Ala Lys Phe His Thr Gln Ala Trp His Ala Leu
            20                  25                  30

Ala Asp Gln Val Asn Val Thr Trp Thr Pro Glu Leu Gln Glu Ser Leu
        35                  40                  45

Lys Gly Ile Asp Arg Met Gly Ser Leu Glu Met Ile Leu Lys Ala Gly
    50                  55                  60

Asn Lys Gln Asp Asp Tyr Thr His Asp Glu Lys Val Ala Leu Ala Ser
65                  70                  75                  80

Trp Lys Asn Asn His Tyr Val Glu Leu Ile Ser Gly Leu Thr Pro Asp
                85                  90                  95

Asp Ile Leu Pro Gly Met Ala Asp Phe Ile Lys Glu Leu Asn Asp Lys
            100                 105                 110

Gly Tyr Arg Ala Ser Val Ala Ser Ala Ser Lys Asn Ala Pro Phe Ile
        115                 120                 125

Leu Asp Lys Leu Gly Leu Thr Asp Ser Phe Val Gly Ile Val Asp Pro
    130                 135                 140

Ala Thr Leu His Ala Gly Lys Pro Asp Pro Glu Ile Phe Val Arg Ala
145                 150                 155                 160

Ala Glu Ile Leu Asn Leu Leu Pro Glu Gln Val Ile Gly Leu Glu Asp
                165                 170                 175

Ser Ala Ala Gly Ile Ala Ser Ile Asn Gly Ala Gly Glu Val Ser Leu
            180                 185                 190

Gly Ile Gly Asp Thr Thr Val Leu Ala Ala Ala Asn Leu Asn Phe Ala
        195                 200                 205
```

```
Ser Thr Ala Glu Val Thr Leu Ala Asn Ile Ala Ala Lys Leu Asp
    210                 215                 220


<210> SEQ ID NO 56
<211> LENGTH: 672
<212> TYPE: DNA
<213> ORGANISM: Artificial sequence
<220> FEATURE:
<223> OTHER INFORMATION: Synthesized: pgmA (Lactobacillus
      sanfranciscensis)

<400> SEQUENCE: 56

atgacgaagt tttcagaaat taagggattt gcctttgact tggatggcgt catcacggac      60

accgctaagt ttcacacgca agcttggcat gcgcttgctg accaagtaaa cgtgacttgg     120

acgccagaat tgcaagagtc attgaaaggg attgaccgca tgggcagtct tgagatgatt     180

ttgaaggctg gcaacaagca agatgactac acacacgatg aaaaggtggc gttggcatct     240

tggaagaata accactacgt tgaattgatt tctggtttga cgccggatga tattttgccg     300

gggatggcag atttcatcaa ggaattgaac gataagggct accgggcgag cgtggcatcg     360

gcgtcaaaga acgcaccgtt tatcttggac aagcttggct taacggatag ctttgtcgga     420

attgttgacc cagcaacgct acatgccggt aagcctgatc cagaaatttt tgtccgcgca     480

gctgaaatct tgaacttgct accggaacaa gtcattggct tagaagattc ggcagccgga     540

attgcgtcaa tcaacggggc cggtgaagtc tcgttgggga ttggggatac gactgtactg     600

gcggcggcga accttaattt tgctagcaca gctgaggtca ccttagctaa cattgcggca     660

aaacttgatt aa                                                         672


<210> SEQ ID NO 57
<211> LENGTH: 221
<212> TYPE: PRT
<213> ORGANISM: Artificial sequence
<220> FEATURE:
<223> OTHER INFORMATION: Synthesized: pgmB (Lactococcus lactis lactis)

<400> SEQUENCE: 57

Met Phe Lys Ala Val Leu Phe Asp Leu Asp Gly Val Ile Thr Asp Thr
1               5                   10                  15

Ala Glu Tyr His Phe Arg Ala Trp Lys Ala Leu Ala Glu Glu Ile Gly
            20                  25                  30

Ile Asn Gly Val Asp Arg Gln Phe Asn Glu Gln Leu Lys Gly Val Ser
        35                  40                  45

Arg Glu Asp Ser Leu Gln Lys Ile Leu Asp Leu Ala Asp Lys Lys Val
    50                  55                  60

Ser Ala Glu Glu Phe Lys Glu Leu Ala Lys Arg Lys Asn Asp Asn Tyr
65                  70                  75                  80

Val Lys Met Ile Gln Asp Val Ser Pro Ala Asp Val Tyr Pro Gly Ile
                85                  90                  95

Leu Gln Leu Leu Lys Asp Leu Arg Ser Asn Lys Ile Lys Ile Ala Leu
            100                 105                 110

Ala Ser Ala Ser Lys Asn Gly Pro Phe Leu Leu Glu Lys Met Asn Leu
        115                 120                 125

Thr Gly Tyr Phe Asp Ala Ile Ala Asp Pro Ala Glu Val Ala Ala Ser
    130                 135                 140

Lys Pro Ala Pro Asp Ile Phe Ile Ala Ala Ala His Ala Val Gly Val
145                 150                 155                 160

Ala Pro Ser Glu Ser Ile Gly Leu Glu Asp Ser Gln Ala Gly Ile Gln
```

```
                165                 170                 175

Ala Ile Lys Asp Ser Gly Ala Leu Pro Ile Gly Val Gly Arg Pro Glu
            180                 185                 190

Asp Leu Gly Asp Asp Ile Val Ile Val Pro Asp Thr Ser Tyr Tyr Thr
        195                 200                 205

Leu Glu Phe Leu Lys Glu Val Trp Leu Gln Lys Gln Lys
    210                 215                 220


<210> SEQ ID NO 58
<211> LENGTH: 666
<212> TYPE: DNA
<213> ORGANISM: Artificial sequence
<220> FEATURE:
<223> OTHER INFORMATION: Synthesized: pgmB (Lactococcus lactis lactis)

<400> SEQUENCE: 58

atgtttaaag cagtattgtt tgatttagat ggtgtaatta cagataccgc agagtatcat     60

tttagagctt ggaaagcttt ggctgaagaa attggcatta atggtgttga ccgccaattt    120

aatgagcaat taaaaggggt ctcacgagaa gactcgcttc agaaaattct agatttagct    180

gataaaaaag tatcagctga ggaatttaaa gaacttgcta agagaaaaaa tgataactat    240

gtgaaaatga ttcaggatgt gtcgccagcc gatgtctatc ctggaatttt acaattactc    300

aaagatttac gttcaaataa aatcaaaatt gctttagcgt cggcttctaa gaatggtcca    360

tttttattag agagaatgaa tttaactgga tattttgatg caattgctga tccggctgaa    420

gttgcagcat caaaaccagc accagatatt tttattgcag cagcacatgc agtgggtgtt    480

gccccctctg aatcaattgg gttagaggat tctcaagctg gaattcaagc catcaaagat    540

tcaggggctt taccaattgg tgtagggcgc ccagaagatt tgggagatga tatcgtcatt    600

gtgcctgata cttcacacta tacattagaa tttttgaaag aagtttggct tcaaaagcaa    660

aaataa                                                                666


<210> SEQ ID NO 59
<211> LENGTH: 1740
<212> TYPE: DNA
<213> ORGANISM: Artificial sequence
<220> FEATURE:
<223> OTHER INFORMATION: Synthesized: cdt-1 (Neurospora crassa)

<400> SEQUENCE: 59

atgtcgtctc acggctccca tgacggggcc agcaccgaga agcatcttgc tactcatgac     60

attgcgccca cccacgacgc catcaagata gtgcccaagg gccatggcca gacagccaca    120

aagcccggtg cccaagagaa ggaggtccgc aacgccgccc tatttgcggc catcaaggag    180

tccaatatca agccctggag caaggagtcc atccacctct atttcgccat cttcgtcgcc    240

ttttgttgtg catgcgccaa cggttacgat ggttcactca tgaccggaat catcgctatg    300

gacaagttcc agaaccaatt ccacactggt gacactggtc ctaaagtctc tgtcatcttt    360

tctctctata ccgttggtgc catggttgga gctcccttcg ctgctatcct ctctgatcgt    420

tttggccgta agaagggcat gttcatcggt ggtatcttta tcattgtcgg ctccattatt    480

gttgctagct cctccaagct cgctcagttt gtcgttggcc gcttcgttct tggcctcggt    540

atcgccatca tgaccgttgc tgccccggcc tactccatcg aaatcgcccc tcctcactgg    600

cgcggccgct gcactggctt ctacaactgc ggttggttcg gaggttcgat tcctgccgcc    660

tgcatcacct atggctgcta cttcattaag agcaactggt catggcgtat ccccttgatc    720
```

-continued

```
cttcaggctt tcacgtgcct tatcgtcatg tcctccgtct tcttcctccc agaatcccct    780

cgcttcctat ttgccaacgg ccgcgacgct gaggctgttg cctttcttgt caagtatcac    840

ggcaacggcg atcccaattc caagctggtg ttgctcgaga ctgaggagat gagggacggt    900

atcaggaccg acggtgtcga caaggtctgg tgggattacc gcccgctctt catgacccac    960

agcggccgct ggcgcatggc ccaggtgctc atgatctcca tctttggcca gttctccggc   1020

aacggtctcg gttacttcaa taccgtcatc ttcaagaaca ttggtgtcac cagcacctcc   1080

caacagctcg cctacaacat cctcaactcc gtcatctccg ctatcggtgc cttgaccgcc   1140

gtctccatga ctgatcgtat gccccgccgc gcggtgctca ttatcggtac cttcatgtgc   1200

gccgctgctc ttgccaccaa ctcgggtctt tcggctactc tcgacaagca gactcaaaga   1260

ggcacgcaaa tcaacctgaa ccagggtatg aacgagcagg atgccaagga caacgcctac   1320

ctccacgtcg acagcaacta cgccaagggt gccctggccg cttacttcct cttcaacgtc   1380

atcttctcct tcacctacac tcccctccag ggtgttattc ccaccgaggc tctcgagacc   1440

accatccgtg gcaagggtct tgccctttcc ggcttcattg tcaacgccat gggcttcatc   1500

aaccagttcg ctggccccat cgctctccac aacattggct acaagtacat ctttgtcttt   1560

gtcggctggg atcttatcga gaccgtcgct tggtacttct ttggtgtcga atcccaaggc   1620

cgtaccctcg agcagctcga atgggtctac gaccagccca accccgtcaa ggcctcccta   1680

aaagtcgaaa aggtcgtcgt ccaggccgac ggccatgtgt ccgaagctat cgttgcttag   1740
```

```
<210> SEQ ID NO 60
<211> LENGTH: 1578
<212> TYPE: DNA
<213> ORGANISM: Artificial sequence
<220> FEATURE:
<223> OTHER INFORMATION: Synthesized: cdt-2 (Neurospora crassa)

<400> SEQUENCE: 60

atgggcatct tcaacaagaa gcccgtggct caggccgtcg acctcaatca gatacaggag     60

gaggctcctc agtttgagag ggttgactgg aagaaggacc ccggtcttcg caagctctac    120

ttctacgcct tcattctttg cattgcttcg gccaccaccg gttacgatgg catgttcttc    180

aactcggtgc agaacttcga gacctggatt aagtactttg gcgacccgcg aggatccgag    240

cttggtctgc tcggtgctct ctaccagatt ggttccattg gctccatccc ctttgtcccc    300

ctccttaccg acaactttgg ccgcaagacc cccatcatca tcggctgcgt tatcatgatc    360

gtcggtgccg ttctccaggc cacggccaag aacctcgata cattcatggg cggccgtacc    420

atgctcggct ttggcaactc cctcgcccag atcgcctccc ccatgcttct caccgagctc    480

gcccatcctc aacaccgcgc tcgtctcacc accatctaca actgcttgtg gaacgttggt    540

gccctcgtcg tctcgtggtt ggcctttggc accaactaca tcaacaacga ctggtcatgg    600

cgcattcccg ccttgctcca ggctttcccc tccatcattc agctcctcgg tatctggtgg    660

gttcccgagt ctccccgttt cctcatcgcc aaggacaagc acgacgaggc cctccacatc    720

ctcgccaagt accacgccaa cggcgacccc aaccacccca ccgtccagtt tgagttccgc    780

gagatcaagg agaccatccg cctcgagatg gaatcgacca agaacagcag ctacctcgac    840

ttcttcaaga gccgcggcaa ccgctaccgc ctcgccatcc tcctctcgct cggcttcttc    900

tcccaatggt ccggcaacgc catcatctcc aactactcct ccaagctgta cgagaccgcc    960

ggcgtcaccg actccaccgc caaactcggt ctttccgccg gacagaccgg tctcgcgctc   1020

atcgtgtccg tcaccatggc gctgctcgtc gacaagctcg gtcgtcgtct tgctttcctc   1080
```

```
gcttccacgg gcggcatgtg cggcaccttt gtcatttgga cgttgacagc cggcctgtac   1140

ggcgagcacc gcctcaaggg cgccgacaag gccatgatct tctttatctg ggtgttcggc   1200

atcttctact cgctcgcctg gtccgggttg ctggtcggct acgccatcga aatcctccct   1260

taccgacttc gcggcaaggg gttgatggtc atgaacatgt cggtgcagtg cgcgctgacg   1320

ctcaatactt atgcgaaccc tgttgcgttt gattactttg gtcctgatca ctcgtggaag   1380

ctttatctta tttacacttg ctggatcgcc gccgagttcg tcttcgtctt cttcatgtac   1440

gtcgagacca agggccccac gctcgaggag cttgccaagg tcattgatgg cgatgaggcc   1500

gatgttgccc acatcgacat tcaccaggtc gagaaggagg tggagattca cgagcatgag   1560

ggcaagtctg ttgcttga                                                 1578
```

```
<210> SEQ ID NO 61
<211> LENGTH: 805
<212> TYPE: PRT
<213> ORGANISM: Artificial sequence
<220> FEATURE:
<223> OTHER INFORMATION: Synthesized: SUS1_SOLTU (Solanum tuberosum)

<400> SEQUENCE: 61

Met Ala Glu Arg Val Leu Thr Arg Val His Ser Leu Arg Glu Arg Val
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Glu Leu Leu
        35                  40                  45

Ala Glu Phe Asp Ala Ile Arg Gln Asp Asp Lys Asn Lys Leu Asn Glu
    50                  55                  60

His Ala Phe Glu Glu Leu Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Ile Arg Val Asn Val Asn Ala Leu Val Val Glu Glu Leu Ser Val
            100                 105                 110

Pro Glu Tyr Leu Gln Phe Lys Glu Glu Leu Val Asp Gly Ala Ser Asn
        115                 120                 125

Gly Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Ala His His Tyr Lys Gly Lys Thr Met
            180                 185                 190

Met Leu Asn Asp Arg Ile Gln Asn Ser Asn Thr Leu Gln Asn Val Leu
        195                 200                 205

Arg Lys Ala Glu Glu Tyr Leu Ile Met Leu Pro Pro Glu Thr Pro Tyr
    210                 215                 220

Phe Glu Phe Glu His Lys Phe Gln Glu Ile Gly Leu Glu Lys Gly Trp
225                 230                 235                 240

Gly Asp Thr Ala Glu Arg Val Leu Glu Met Val Cys Met Leu Leu Asp
                245                 250                 255

Leu Leu Glu Ala Pro Asp Ser Cys Thr Leu Glu Lys Phe Leu Gly Arg
            260                 265                 270
```

```
Ile Pro Met Val Phe Asn Val Val Ile Leu Ser Pro His Gly Tyr Phe
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Ile Pro Arg Ile Leu Ile Val Thr
                325                 330                 335

Arg Leu Leu Pro Asp Ala Val Gly Thr Thr Cys Gly Gln Arg Ile Glu
            340                 345                 350

Lys Val Tyr Gly Ala Glu His Ser His Ile Leu Arg Val Pro Phe Arg
        355                 360                 365

Thr Glu Lys Gly Ile Val Arg Lys Trp Ile Ser Arg Phe Glu Val Trp
    370                 375                 380

Pro Tyr Met Glu Thr Phe Ile Glu Asp Val Ala Lys Glu Ile Ser Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Trp Lys Lys Phe Asp Glu Lys Tyr His Phe Ser Ser Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
            500                 505                 510

Asn Val Phe Asp Pro Lys Phe Asn Ile Val Ser Pro Gly Ala Asp Ile
        515                 520                 525

Asn Leu Tyr Phe Ser Tyr Ser Glu Thr Glu Lys Arg Leu Thr Ala Phe
    530                 535                 540

His Pro Glu Ile Asp Glu Leu Leu Tyr Ser Asp Val Glu Asn Asp Glu
545                 550                 555                 560

His Leu Cys Val Leu Lys Asp Arg Thr Lys Pro Ile Leu Phe Thr Met
                565                 570                 575

Ala Arg Leu Asp Arg Val Lys Asn Leu Thr Gly Leu Val Glu Trp Tyr
            580                 585                 590

Ala Lys Asn Pro Arg Leu Arg Gly Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Glu Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Lys Gly Ala Phe Val Gln Pro Ala Phe Tyr
            660                 665                 670

Glu Ala Phe Gly Leu Thr Val Val Glu Ala Met Thr Cys Gly Leu Pro
        675                 680                 685
```

-continued

```
Thr Phe Ala Thr Asn His Gly Gly Pro Ala Glu Ile Ile Val His Gly
    690                 695                 700

Lys Ser Gly Phe His Ile Asp Pro Tyr His Gly Glu Gln Ala Ala Asp
705                 710                 715                 720

Leu Leu Ala Asp Phe Phe Glu Lys Cys Lys Lys Asp Pro Ser His Trp
                725                 730                 735

Glu Thr Ile Ser Met Gly Gly Leu Lys Arg Ile Glu Glu Lys Tyr Thr
            740                 745                 750

Trp Gln Ile Tyr Ser Glu Ser Leu Leu Thr Leu Ala Ala Val Tyr Gly
        755                 760                 765

Phe Trp Lys His Val Ser Lys Leu Asp Arg Leu Glu Ile Arg Arg Tyr
    770                 775                 780

Leu Glu Met Phe Tyr Ala Leu Lys Tyr Arg Lys Met Ala Glu Ala Val
785                 790                 795                 800

Pro Leu Ala Ala Glu
                805
```

<210> SEQ ID NO 62
<211> LENGTH: 2418
<212> TYPE: DNA
<213> ORGANISM: Artificial sequence
<220> FEATURE:
<223> OTHER INFORMATION: Synthesized: SUS1_SOLTU (Solanum tuberosum)

<400> SEQUENCE: 62

```
atggctgaac gtgttttgac tcgtgttcat agtcttcgtg agcgtgttga tgcaacttta     60

gctgctcacc gcaatgagat actgctgttt ctttcaagga tcgaaagcca cggaaaaggg    120

atcttgaaac ctcacgagct tttggctgaa tttgatgcaa ttcgccaaga tgacaaaaac    180

aaactgaacg aacatgcatt cgaagaactc ctgaaatcca ctcaggaagc gattgttctg    240

ccccccttggg ttgcacttgc tattcgtttg aggcctggtg tctgggaata catccgtgtg    300

aacgtcaacg cactagttgt tgaggagctg tctgtccctg agtatttgca attcaaggaa    360

gaacttgtcg acggagcctc gaatggaaat ttcgttctcg agttggattt cgagcctttt    420

actgcatcct ttcctaaacc aaccctcacc aaatctattg gaaatggagt tgaattcctc    480

aataggcacc tctctgccaa aatgttccat gacaaggaaa gcatgacccc gcttctcgaa    540

tttcttcgcg ctcaccatta taagggcaag acaatgatgc tgaatgatag gatacagaat    600

tcgaatactc ttcaaaatgt cctaaggaag gcagaggaat acctcattat gcttcccccg    660

gaaactccat atttcgaatt cgaacacaag ttccaagaaa tcggattgga gaaaggatgg    720

ggggacacgg cggagcgtgt gctagagatg gtatgcatgc ttcttgatct ccttgaggct    780

cctgactcat gtactcttga gaagttcttg ggagagaattc ctatggtttt caatgtggtt    840

atcctttccc ctcatggata ttttgctcaa gaaaatgtct tgggttatcc tgacaccggt    900

ggccaggttg tctacatttt agatcaagtt cccgccttgg agcgtgaaat gcttaagcgc    960

ataaaggagc aaggacttga tatcatcccc cgtattctta ttgttactcg tctgctcccc   1020

gatgcagttg gaaccacttg tggtcagagg attgagaagg tgtatggagc agaacactca   1080

catattctta gggtcccttt taggactgag aagggcattg ttcgcaaatg gatctctcgc   1140

tttgaagtgt ggccatacat ggagacattc attgaggatg ttgcaaaaga aatttctgca   1200

gaactgcagg ccaagccaga tttgataatc ggaaactaca gtgagggcaa tcttgctgct   1260

tctttgctag ctcacaagtt aggcgtaacg cagtgcacca ttgcccacgc gttggagaaa   1320

acgaagtatc ctgattccga catttactgg aaaaagtttg atgaaaaata ccatttctcg   1380
```

```
tcccagttta ccgctgatct cattgcaatg aatcacactg atttcatcat caccagcacc   1440

ttccaggaga tagcaggaag caaggacact gtgggacaat atgagagcca tatggcattc   1500

acaatgcctg gattgtacag agttgttcac ggcattaatg tgttcgaccc caaattcaac   1560

attgtctcac ctggagctga tattaacctc tacttctcgt actccgaaac ggagaagaga   1620

cttacagcat ttcaccctga aattgatgag ctgctgtata gtgatgttga gaatgacgaa   1680

catctgtgcg tgctcaagga caggactaaa ccaattttat tcacaatggc gaggttggat   1740

cgtgtgaaga atttaactgg acttgttgag tggtacgcca aaaatccacg gctaagggga   1800

ttggttaacc tggttgtagt tggcggagat cgaaggaagg aatccaaaga tttggaagag   1860

caggcagaga tgaagaagat gtatgagcta attgagactc ataatttgaa tggccaattc   1920

agatggattt cttcccagat gaaccgagtg aggaatggtg agctctaccg atacattgct   1980

gacactaagg gagctttcgt tcagcctgca ttctacgagg cttttggtct gactgttgtc   2040

gaagcaatga cttgtggttt gcctacattt gcaactaatc acggtggtcc agctgagatc   2100

atcgttcatg gaaagtccgg cttccacatt gatccatatc acggtgagca agctgctgat   2160

ctgctagctg atttctttga gaaatgcaag aaagatcctt cacattggga aaccatttcg   2220

atgggtggcc tgaagcgcat cgaagagaag tacacttggc aaatctactc cgaaagccta   2280

ttgacactgg ctgctgttta tgggttctgg aaacatgttt ctaagcttga tcgtctagaa   2340

atccgtcgct atcttgaaat gttttatgct ctcaagtacc gtaagatggc tgaagctgtt   2400

ccattggctg ctgagtga                                                 2418
```

<210> SEQ ID NO 63
<211> LENGTH: 476
<212> TYPE: PRT
<213> ORGANISM: Artificial sequence
<220> FEATURE:
<223> OTHER INFORMATION: Synthesized: THITE_2171046 (Thielavia terrestris)

<400> SEQUENCE: 63

```
Met Ser Leu Pro Lys Asp Phe Lys Trp Gly Phe Ala Thr Ala Ala Tyr
1               5                   10                  15

Gln Ile Glu Gly Ser Ala Thr Glu Asp Gly Arg Gly Pro Ser Ile Trp
            20                  25                  30

Asp Thr Phe Cys Ala Ile Pro Gly Lys Ile Ala Asp Gly Ser Ser Gly
        35                  40                  45

Ala Val Ala Cys Asp Ser Tyr Arg Arg Thr Lys Glu Asp Ile Glu Leu
    50                  55                  60

Leu Lys Ser Leu Gly Ala Thr Ala Tyr Arg Phe Ser Ile Ser Trp Ser
65                  70                  75                  80

Arg Ile Ile Pro Leu Gly Gly Arg Asn Asp Pro Ile Asn Gln Lys Gly
                85                  90                  95

Ile Asp His Tyr Val Lys Phe Val Asp Asp Leu Leu Glu Ala Gly Ile
            100                 105                 110

Glu Pro Phe Ile Thr Leu Phe His Trp Asp Leu Pro Asp Ala Leu Asp
        115                 120                 125

Lys Arg Tyr Gly Gly Leu Leu Asn Lys Glu Glu Phe Ser Ala Asp Phe
    130                 135                 140

Glu Asn Tyr Ala Arg Ile Met Phe Lys Ala Ile Pro Lys Cys Lys His
145                 150                 155                 160

Trp Ile Thr Phe Asn Glu Pro Trp Cys Ser Ser Ile Leu Gly Tyr Asn
```

-continued

```
                165                 170                 175

Ser Gly Tyr Phe Ala Pro Gly Arg Thr Ser Asp Arg Ser Lys Ser Pro
            180                 185                 190

Val Gly Asp Ser Ala Arg Glu Pro Trp Ile Val Gly His Asn Ile Leu
        195                 200                 205

Ile Ala His Gly Lys Ala Val Lys Ala Tyr Arg Asp Asp Phe Lys Pro
    210                 215                 220

Thr Gln Gly Gly Glu Ile Gly Ile Thr Leu Asn Gly Asp Ala Thr Leu
225                 230                 235                 240

Pro Trp Asp Pro Glu Asp Pro Ala Asp Val Glu Ala Cys Asp Arg Lys
                245                 250                 255

Ile Glu Phe Ala Ile Ser Trp Phe Ala Asp Pro Ile Tyr Phe Gly His
            260                 265                 270

Tyr Pro Glu Ser Met Arg Lys Gln Leu Gly Asp Arg Leu Pro Thr Phe
        275                 280                 285

Thr Pro Glu Glu Val Ala Leu Val Lys Gly Ser Asn Asp Phe Tyr Gly
    290                 295                 300

Met Asn His Tyr Thr Ala Asn Tyr Ile Lys His Lys Lys Gly Val Pro
305                 310                 315                 320

Pro Glu Asp Asp Phe Leu Gly Asn Leu Glu Thr Leu Phe Tyr Asn Lys
                325                 330                 335

His Gly Asp Cys Ile Gly Pro Glu Thr Gln Ser Phe Trp Leu Arg Pro
            340                 345                 350

His Ala Gln Gly Phe Arg Asp Leu Leu Asn Trp Leu Ser Lys Arg Tyr
        355                 360                 365

Gly Tyr Pro Lys Ile Tyr Val Thr Glu Asn Gly Thr Ser Val Lys Gly
    370                 375                 380

Glu Asn Asp Met Pro Leu Glu Gln Ile Val Glu Asp Asp Phe Arg Val
385                 390                 395                 400

Lys Tyr Phe His Asp Tyr Val His Ala Met Ala Arg Ala Ser Ala Glu
                405                 410                 415

Asp Gly Val Asn Val Arg Ala Tyr Leu Ala Trp Ser Leu Met Asp Asn
            420                 425                 430

Phe Glu Trp Ala Glu Gly Tyr Glu Thr Arg Phe Gly Val Thr Tyr Val
        435                 440                 445

Asp Tyr Ala Asn Asp Gln Lys Arg Tyr Pro Lys Lys Ser Ala Arg Ser
    450                 455                 460

Leu Lys Pro Leu Phe Asp Ser Leu Ile Lys Lys Asp
465                 470                 475
```

<210> SEQ ID NO 64
<211> LENGTH: 1431
<212> TYPE: DNA
<213> ORGANISM: Artificial sequence
<220> FEATURE:
<223> OTHER INFORMATION: Synthesized: THITE_2171046 (Thielavia terrestris)

<400> SEQUENCE: 64

```
atgtctctcc ccaaggactt caagtggggg ttcgccactg ccgcgtacca gattgagggc     60

tcggccaccg aggatggccg tggcccgtcc atctgggaca ccttttgcgc catccccggc    120

aagattgccg acggcagctc cggcgcggtg gcctgcgact cgtacaggcg caccaaggag    180

gacatcgagc tgctcaagtc gctgggggcc acggcctacc gcttctccat ctcgtggtcg    240

cgcatcatcc cgctcggcgg tcgcaacgac cccatcaacc agaagggcat cgaccactac    300
```

```
gtcaagttcg tcgacgacct cctggaggcc ggcatcgagc ccttcatcac gctcttccac    360

tgggacctgc cggacgcgct ggacaagcgc tacggcggcc tgttgaacaa ggaggagttc    420

tcggccgact tcgagaacta cgcgcgcatc atgttcaagg cgatccccaa gtgcaagcac    480

tggatcacgt tcaacgagcc gtggtgctcg tccatcctgg gctacaacag cggctatttc    540

gcgcccggcc gcacgtcgga ccgcagcaag tcgccggtgg gcgacagcgc gcgcgagccg    600

tggattgtcg gccacaacat cctgatcgcg cacggcaagg cggtcaaggc gtaccgcgac    660

gacttcaagc cgacgcaggg cggcgagatc ggcatcacgc tcaacggcga cgccacgctg    720

ccgtgggacc cggaggaccc ggctgacgtg gaggcgtgcg accgcaagat cgagttcgcc    780

atctcgtggt tcgccgatcc catctacttc ggccattacc cggagtcgat gcgcaagcag    840

ctcggcgacc ggctgccgac cttcacgccg gaagaggtgg cgctcgtcaa gggctccaac    900

gacttctacg gcatgaacca ctacacggcc aactacatca agcacaagaa gggcgtgccg    960

cccgaggacg acttcctggg caacctcgag acgctcttct acaacaagca cggcgactgc   1020

atcgggcccg agacgcagtc cttctggctg cggccgcacg cgcagggctt ccgcgacctg   1080

ctcaactggc tcagcaagcg gtacggctac cccaagatct acgtgacgga gaacggcacg   1140

tcggtcaagg gcgagaacga catgccgctc gagcagatcg tcgaggacga cttccgcgtc   1200

aagtacttcc acgactacgt gcacgccatg gcccgcgcct cggccgagga cggcgtcaac   1260

gtgcgcgcct acctcgcctg gtcgctcatg gacaacttcg agtgggccga gggctacgag   1320

acccgcttcg gcgtcaccta cgtcgactac gccaacgacc agaagcgcta ccccaagaag   1380

agcgccagga gcctcaagcc cctgtttgac agcctgatca agaaggacta g            1431
```

<210> SEQ ID NO 65
<211> LENGTH: 811
<212> TYPE: PRT
<213> ORGANISM: Artificial sequence
<220> FEATURE:
<223> OTHER INFORMATION: Synthesized: cep94A (Saccharophagus degradans)

<400> SEQUENCE: 65

```
Met Lys Phe Gly His Phe Asp Asp Lys Ala Arg Glu Tyr Val Ile Thr
1               5                   10                  15

Asp Pro Lys Thr Pro Tyr Pro Trp Ile Asn Tyr Leu Gly Asn Glu Asp
            20                  25                  30

Phe Phe Ser Leu Val Ser Asn Thr Gly Gly Gly Tyr Ser Phe Tyr Lys
        35                  40                  45

Asp Ala Lys Phe Arg Arg Leu Thr Arg Tyr Arg Tyr Asn Asn Val Pro
    50                  55                  60

Val Asp Asn Gly Gly Lys Tyr Phe Tyr Ile Asn Asp Ser Gly Asp Val
65                  70                  75                  80

Trp Ser Pro Gly Trp Lys Pro Val Lys Ala Glu Leu Asp Ala Tyr Ser
                85                  90                  95

Cys Ala His Gly Leu Ser Tyr Thr Arg Ile Thr Gly Glu Arg Asn Gly
            100                 105                 110

Ile Gln Ala Glu Val Leu Ser Phe Ile Pro Leu Gly Thr Trp Ala Glu
        115                 120                 125

Ile Gln Lys Val Ser Leu Lys Asn Thr Ser Gly Ala Thr Lys Lys Phe
    130                 135                 140

Lys Leu Phe Ser Phe Ala Glu Trp Cys Leu Trp Asn Ala Glu Asp Asp
145                 150                 155                 160
```

-continued

```
Met Thr Asn Phe Gln Arg Asn Phe Ser Thr Gly Glu Val Glu Val Glu
                165                 170                 175

Asp Ser Val Ile Tyr His Lys Thr Glu Phe Lys Glu Arg Arg Asn His
            180                 185                 190

Tyr Ala Phe Tyr Ser Val Asn Ala Pro Ile Gln Gly Phe Asp Thr Asp
        195                 200                 205

Arg Asp Lys Trp Lys Gly Leu Tyr Asn Asp Phe Asp Lys Pro Asp Ala
    210                 215                 220

Val Phe Glu Gly Glu Pro Arg Asn Ser Glu Ala His Gly Trp Ser Pro
225                 230                 235                 240

Ile Ala Ser His Tyr Leu Glu Val Glu Leu Ala Pro Gly Glu Ser Lys
                245                 250                 255

Asp Leu Ile Phe Val Leu Gly Tyr Ile Glu Val Ala Pro Glu Asn Lys
            260                 265                 270

Trp Glu Ser Lys Gly Val Ile Asn Lys Ser Pro Ala Lys Glu Leu Ile
        275                 280                 285

Ala Arg Phe Asp Ser Val Glu Lys Val Asp Ala Glu Leu Thr Lys Leu
    290                 295                 300

Ala Asp Tyr Trp Ala Asn Leu Leu Ser Thr Tyr Ser Val Glu Ser Gly
305                 310                 315                 320

Asp Glu Lys Leu Asp Arg Met Val Asn Ile Trp Asn Gln Tyr Gln Cys
                325                 330                 335

Met Val Thr Phe Asn Met Ser Arg Ser Ala Ser Phe Phe Glu Ser Gly
            340                 345                 350

Ile Gly Arg Gly Met Gly Phe Arg Asp Ser Asn Gln Asp Leu Ile Gly
        355                 360                 365

Phe Val His Gln Val Pro Glu Arg Ala Arg Glu Arg Ile Ile Asp Ile
    370                 375                 380

Ala Ser Thr Gln Phe Glu Asp Gly Ser Ala Tyr His Gln Tyr Gln Pro
385                 390                 395                 400

Leu Thr Lys Arg Gly Asn Asn Ala Ile Gly Gly Asn Phe Asn Asp Asp
                405                 410                 415

Pro Leu Trp Leu Ile Leu Ser Thr Thr Asp Tyr Ile Lys Glu Thr Gly
            420                 425                 430

Asp Phe Ser Ile Leu Glu Glu Gln Val Pro Tyr Asp Asn Asp Ala Ser
        435                 440                 445

Lys Ala Thr Ser His Phe Glu His Leu Lys Arg Ser Phe Tyr His Thr
    450                 455                 460

Val Asn Asn Leu Gly Pro His Gly Leu Pro Leu Ile Gly Arg Ala Asp
465                 470                 475                 480

Trp Asn Asp Cys Leu Asn Leu Asn Cys Phe Ser Glu Asp Pro Asn Glu
                485                 490                 495

Ser Phe Gln Thr Thr Gly Asn Lys Thr Gly Arg Thr Ala Glu Ser Leu
            500                 505                 510

Met Ile Ala Gly Leu Phe Val Leu Tyr Gly Asn Glu Phe Val Lys Leu
        515                 520                 525

Cys Arg Glu Ile Gly Gln Asp Gly Glu Ala Ala Glu Ala Gln Ala His
    530                 535                 540

Ile Asp Gln Met Val Glu Ala Val Lys Lys His Gly Trp Asp Gly Glu
545                 550                 555                 560

Trp Phe Leu Arg Ala Tyr Asp Tyr Tyr Gly Lys Lys Val Gly Ser Lys
                565                 570                 575

Glu Asn Glu Glu Gly Lys Ile Phe Ile Glu Ser Gln Gly Phe Cys Gly
```

```
            580                 585                 590

Met Ala Gly Ile Gly Leu Glu Asp Gly Leu Val Glu Lys Ser Met Asp
        595                 600                 605

Ser Val Lys Glu Trp Leu Asp Cys Asp Tyr Gly Ile Val Leu Gln Gln
    610                 615                 620

Pro Ala Phe Thr Lys Tyr Tyr Ile Glu Tyr Gly Glu Ile Ser Thr Tyr
625                 630                 635                 640

Pro Ala Gly Tyr Lys Glu Asn Ala Gly Ile Phe Cys His Asn Asn Pro
                645                 650                 655

Trp Ile Met Ile Thr Glu Thr Leu Leu Gly Arg Gly Asp Lys Ala Phe
            660                 665                 670

Glu Tyr Tyr Arg Lys Ile Ala Pro Ala Tyr Leu Glu Glu Ile Ser Asp
        675                 680                 685

Leu His Lys Val Glu Pro Tyr Ala Tyr Cys Gln Met Ile Ala Gly Lys
    690                 695                 700

Asp Ala Tyr Leu Pro Gly Glu Gly Lys Asn Ser Trp Leu Thr Gly Thr
705                 710                 715                 720

Ala Ser Trp Asn Phe Ala Ala Ile Thr Gln Tyr Ile Leu Gly Val Lys
                725                 730                 735

Pro Asp Tyr Ser Gly Leu Ala Ile Asn Pro Cys Ile Pro Ser Ser Trp
            740                 745                 750

Asp Gly Phe Lys Val Thr Arg Lys Tyr Arg Gly Ala Thr Tyr Asn Ile
        755                 760                 765

Ile Val Thr Asn Pro Thr His Val Ser Lys Gly Val Lys Ser Leu Thr
    770                 775                 780

Leu Asn Gly Asn Ala Ile Asp Gly Tyr Ile Val Pro Pro Gln Gln Ala
785                 790                 795                 800

Gly Thr Val Cys Asn Val Glu Val Thr Leu Gly
                805                 810
```

<210> SEQ ID NO 66
<211> LENGTH: 2436
<212> TYPE: DNA
<213> ORGANISM: Artificial sequence
<220> FEATURE:
<223> OTHER INFORMATION: Synthesized: cep94A (Saccharophagus degradans)

<400> SEQUENCE: 66

```
atgaaatttg ggcactttga cgacaaagca cgcgagtatg taattaccga cccgaaaact     60

ccctacccgt ggataaacta cttaggcaac gaagacttct tcagcctagt atctaacact    120

gggggtggct acagttttta caaagatgca aagttccgtc gtttaacacg ctatagatac    180

aacaacgtac ccgtagacaa cggcggtaaa tatttttaca tcaatgatag tggcgatgta    240

tggagccccg gttggaagcc ggtaaaagca gagctagacg catacagctg cgctcacggc    300

cttagctaca cccgcattac cggcgaaaga aacggcattc aagcggaagt acttagcttt    360

atccctctcg gcacttgggc cgaaattcaa aaagttagcc ttaagaatac ctctggcgct    420

accaaaaaat ttaaactgtt ttctttcgcc gaatggtgcc tatggaacgc agaagatgac    480

atgaccaact tccaacgcaa cttctccacc ggtgaagtag aggtggaaga ctctgttatt    540

tatcacaaga cagaatttaa agagcgccgc aatcattacg cattctactc tgtaaacgca    600

ccaattcagg gcttcgacac cgacagagac aaatggaaag gcttgtacaa cgattttgat    660

aaacccgatg ccgtttttga aggcgagcct cgcaactccg aagcgcacgg ctggtcgcca    720

attgcatctc actatctaga agtggagctc gcaccaggcg aaagcaaaga cttaattttt    780
```

```
gtgcttggct atatagaagt tgccccagaa aacaaatggg aatcaaaggg cgttatcaac    840

aagtctccag ccaaagaact tattgcgcgt ttcgatagcg tagaaaaagt agatgccgag    900

ttaaccaagc tagccgatta ttgggcaaat ttgctttcta cttacagcgt agaaagtggc    960

gacgaaaagc tagaccgcat ggtaaatatt tggaaccaat accagtgtat ggtgacattt   1020

aatatgagtc gctctgcgtc tttcttcgaa tctggcattg gccgtggtat gggcttccgc   1080

gattccaatc aggatttgat aggctttgta caccaagtac ccgagcgcgc ccgcgaacgc   1140

ataattgata ttgcttctac tcagtttgaa gacggttcgg cctaccacca gtatcagcct   1200

ttaaccaaac gcggcaacaa cgcaattggc ggcaacttta acgatgaccc tctttggcta   1260

atcctttcta ccaccgatta cataaaagag actggcgatt tctctatttt agaagagcaa   1320

gtgccttacg ataatgatgc gagcaaagcc acaagtcatt ttgaacattt aaagcgctcg   1380

ttttatcaca cggttaataa tttaggccca catggcttgc cacttattgg tcgcgccgac   1440

tggaacgact gcctaaacct aaactgcttt agtgaagacc ctaacgaatc attccaaacc   1500

acgggcaaca aaaccggcag aacggctgag tcgttaatga ttgcaggttt atttgtttta   1560

tacggcaacg agtttgtaaa actgtgccgt gaaataggcc aagacggaga agcggcagaa   1620

gcccaagccc atattgacca aatggtagaa gctgtgaaaa agcacggctg ggatggcgag   1680

tggtttttgc gtgcttacga ctactacggt aaaaaagtag gcagtaaaga aaacgaagaa   1740

ggcaaaatat ttatcgaatc gcaaggtttc tgcggcatgg caggaatcgg cctagaagac   1800

ggccttgtcg aaaaatcgat ggattctgtt aaagaatggt tagattgcga ttacggtatt   1860

gtgttgcagc aaccggcgtt taccaagtac tacatagagt atggtgaaat ctccacctac   1920

cctgctggct acaaagagaa cgcaggtatc ttctgccaca acaacccgtg gattatgatc   1980

accgaaactt tgcttggccg cggtgacaaa gcctttgaat actaccgcaa aattgcacct   2040

gcatacctag aggaaattag cgatcttcac aaagtagagc cttacgccta ctgccagatg   2100

attgcaggta aagatgccta cttacctggc gagggtaaaa actcatggct aacagggacc   2160

gcttcgtgga acttcgctgc aattactcag tacattttag gcgtaaaacc agactatagc   2220

ggtttagcaa ttaacccttg cataccgtct agctgggatg gctttaaagt tacccgtaag   2280

tatcgcggcg caacctataa catcatcgta accaacccaa cccatgtaag caaaggcgta   2340

aaatcgctca ccctaaatgg caacgctatt gatggctaca tagtgccacc gcaacaagct   2400

ggcaccgtat gtaacgtaga agttacattg ggctaa                             2436
```

<210> SEQ ID NO 67
<211> LENGTH: 1578
<212> TYPE: DNA
<213> ORGANISM: Artificial sequence
<220> FEATURE:
<223> OTHER INFORMATION: Synthesized: cdt-2 mutations Q207H, N311H, I505T (Neurospora crassa)

<400> SEQUENCE: 67

```
atgggcatct tcaacaagaa gcccgtggct caggccgtcg acctcaatca gatacaggag     60

gaggctcctc agtttgagag ggttgactgg aagaaggacc ccggtcttcg caagctctac    120

ttctacgcct tcattctttg cattgcttcg gccaccaccg gttacgatgg catgttcttc    180

aactcggtgc agaacttcga gacctggatt aagtactttg gcgacccgcg aggatccgag    240

cttggtctgc tcggtgctct ctaccagatt ggttccattg gctccatccc ctttgtcccc    300

ctccttaccg acaactttgg ccgcaagacc cccatcatca tcggctgcgt tatcatgatc    360
```

```
gtcggtgccg ttctccaggc cacggccaag aacctcgata cattcatggg cggccgtacc    420

atgctcggct ttggcaactc cctcgcccag atcgcctccc ccatgcttct caccgagctc    480

gcccatcctc aacaccgcgc tcgtctcacc accatctaca actgcttgtg gaacgttggt    540

gccctcgtcg tctcgtggtt ggcctttggc accaactaca tcaacaacga ctggtcatgg    600

cgcattcccg ccttgctcca cgctttcccc tccatcattc agctcctcgg tatctggtgg    660

gttcccgagt ctccccgttt cctcatcgcc aaggacaagc acgacgaggc cctccacatc    720

ctcgccaagt accacgccaa cggcgacccc aaccacccca ccgtccagtt tgagttccgc    780

gagatcaagg agaccatccg cctcgagatg gaatcgacca agaacagcag ctacctcgac    840

ttcttcaaga gccgcggcaa ccgctaccgc ctcgccatcc tcctctcgct cggcttcttc    900

tcccaatggt ccggcaacgc catcatctcc cactactcct ccaagctgta cgagaccgcc    960

ggcgtcaccg actccaccgc caaactcggt ctttccgccg gacagaccgg tctcgcgctc   1020

atcgtgtccg tcaccatggc gctgctcgtc gacaagctcg gtcgtcgtct tgctttcctc   1080

gcttccacgg gcggcatgtg cggcaccttt gtcatttgga cgttgacagc cggcctgtac   1140

ggcgagcacc gcctcaaggg cgccgacaag gccatgatct tctttatctg ggtgttcggc   1200

atcttctact cgctcgcctg gtccgggttg ctggtcggct acgccatcga aatcctccct   1260

taccgacttc gcggcaaggg gttgatggtc atgaacatgt cggtgcagtg cgcgctgacg   1320

ctcaatactt atgcgaaccc tgttgcgttt gattactttg gtcctgatca ctcgtggaag   1380

ctttatctta tttacacttg ctggatcgcc gccgagttcg tcttcgtctt cttcatgtac   1440

gtcgagacca agggccccac gctcgaggag cttgccaagg tcattgatgg cgatgaggcc   1500

gatgttgccc acaccgacat tcaccaggtc gagaaggagg tggagattca cgagcatgag   1560

ggcaagtctg ttgcttga                                                 1578
```

<210> SEQ ID NO 68
<211> LENGTH: 1621
<212> TYPE: DNA
<213> ORGANISM: Artificial sequence
<220> FEATURE:
<223> OTHER INFORMATION: Synthesized: BKO1008-BKO1009, amplified from plasmid pUG6

<400> SEQUENCE: 68

```
ttaattgaga atacggttga cctggcatgt tgttcgaatc ataacttcgt ataatgtatg     60

ctatacgaag ttattaggtc tagagatctg tttagcttgc ctcgtccccg ccgggtcacc    120

cggccagcga catggaggcc cagaataccc tccttgacag tcttgacgtg cgcagctcag    180

gggcatgatg tgactgtcgc ccgtacattt agcccataca tccccatgta taatcatttg    240

catccataca ttttgatggc cgcacggcgc gaagcaaaaa ttacggctcc tcgctgcaga    300

cctgcgagca gggaaacgct cccctcacag acgcgttgaa ttgtccccac gccgcgcccc    360

tgtagagaaa tataaaaggt taggatttgc cactgaggtt cttctttcat atacttcctt    420

ttaaaatctt gctaggatac agttctcaca tcacatccga acataaacaa ccatgggtaa    480

ggaaaagact cacgtttcga ggccgcgatt aaattccaac atggatgctg atttatatgg    540

gtataaatgg gctcgcgata atgtcgggca atcaggtgcg acaatctatc gattgtatgg    600

gaagcccgat gcgccagagt tgtttctgaa acatggcaaa ggtagcgttg ccaatgatgt    660

tacagatgag atggtcagac taaactggct gacggaattt atgcctcttc cgaccatcaa    720

gcattttatc cgtactcctg atgatgcatg gttactcacc actgcgatcc ccggcaaaac    780
```

```
agcattccag gtattagaag aatatcctga ttcaggtgaa aatattgttg atgcgctggc    840

agtgttcctg cgccggttgc attcgattcc tgtttgtaat tgtcctttta acagcgatcg    900

cgtatttcgt ctcgctcagg cgcaatcacg aatgaataac ggtttggttg atgcgagtga    960

ttttgatgac gagcgtaatg gctggcctgt tgaacaagtc tggaaagaaa tgcataagct   1020

tttgccattc tcaccggatt cagtcgtcac tcatggtgat ttctcacttg ataaccttat   1080

ttttgacgag gggaaattaa taggttgtat tgatgttgga cgagtcggaa tcgcagaccg   1140

ataccaggat cttgccatcc tatggaactg cctcggtgag ttttctcctt cattacagaa   1200

acggcttttt caaaaatatg gtattgataa tcctgatatg aataaattgc agtttcattt   1260

gatgctcgat gagtttttct aatcagtact gacaataaaa agattcttgt tttcaagaac   1320

ttgtcatttg tatagttttt ttatattgta gttgttctat tttaatcaaa tgttagcgtg   1380

atttatattt tttttcgcct cgacatcatc tgcccagatg cgaagttaag tgcgcagaaa   1440

gtaatatcat gcgtcaatcg tatgtgaatg ctggtcgcta tactgctgtc gattcgatac   1500

taacgccgcc atccagtgtc gaaaacgagc tctcgagaac ccttaatata acttcgtata   1560

atgtatgcta tacgaagtta tgcactgttg ataatttgtt tcaccattat gggtaaatgt   1620

g                                                                   1621
```

<210> SEQ ID NO 69
<211> LENGTH: 1258
<212> TYPE: DNA
<213> ORGANISM: Artificial sequence
<220> FEATURE:
<223> OTHER INFORMATION: Synthesized: BKO1016-BKO1017, amplified from chromosomal DNA of S. cerevisiae S288c

<400> SEQUENCE: 69

```
gatatgtatt attcttcaaa acattctctt gttcttgtgc aattcccgtt ttaagagctt     60

ggtgagcgct aggagtcact gccaggtatc gtttgaacac ggcattagtc agggaagtca    120

taacacagtc ctttcccgca attttctttt tctattactc ttggcctcct ctagtacact    180

ctatattttt ttatgcctcg gtaatgattt tcattttttt ttttccccta gcggatgact    240

cttttttttt cttagcgatt ggcattatca cataatgaat tatacattat ataaagtaat    300

gtgatttctt cgaagaatat actaaaaaat gagcaggcaa gataaacgaa ggcaaagatg    360

acagagcaga aagccctagt aaagcgtatt acaaatgaaa ccaagattca gattgcgatc    420

tctttaaagg gtggtcccct agcgatagag cactcgatct tcccagaaaa agaggcagaa    480

gcagtagcag aacaggccac acaatcgcaa gtgattaacg tccacacagg tatagggttt    540

ctggaccata tgatacatgc tctggccaag cattccggct ggtcgctaat cgttgagtgc    600

attggtgact tacacataga cgaccatcac accactgaag actgcgggat tgctctcggt    660

caagctttta aagaggccct actggcgcgt ggagtaaaaa ggtttggatc aggatttgcg    720

cctttggatg aggcactttc cagagcggtg gtagatcttt cgaacaggcc gtacgcagtt    780

gtcgaacttg gtttgcaaag ggagaaagta ggagatctct cttgcgagat gatcccgcat    840

tttcttgaaa gctttgcaga ggctagcaga attaccctcc acgttgattg tctgcgaggc    900

aagaatgatc atcaccgtag tgagagtgcg ttcaaggctc ttgcggttgc cataagagaa    960

gccacctcgc ccaatggtac caacgatgtt ccctccacca aaggtgttct tatgtagtga   1020

caccgattat ttaaagctgc agcatacgat atatatacat gtgtatatat gtatacctat   1080

gaatgtcagt aagtatgtat acgaacagta tgatactgaa gatgacaagg taatgcatca   1140
```

ttctatacgt gtcattctga acgaggcgcg ctttcctttt ttctttttgc tttttctttt 1200
tttttctctt gaactcgact ttatgatttc aaagaatacc tccaaaccat tgaaaatg 1258

<210> SEQ ID NO 70
<211> LENGTH: 6021
<212> TYPE: DNA
<213> ORGANISM: Artificial sequence
<220> FEATURE:
<223> OTHER INFORMATION: Synthesized: pRS415

<400> SEQUENCE: 70
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatcga ctacgtcgta aggccgtttc tgacagagta aaattcttga gggaactttc 240
accattatgg gaaatggttc aagaaggtat tgacttaaac tccatcaaat ggtcaggtca 300
ttgagtgttt tttatttgtt gtattttttt ttttttagag aaaatcctcc aatatcaaat 360
taggaatcgt agtttcatga ttttctgtta cacctaactt tttgtgtggt gccctcctcc 420
ttgtcaatat taatgttaaa gtgcaattct ttttccttat cacgttgagc cattagtatc 480
aatttgctta cctgtattcc tttactatcc tcctttttct ccttcttgat aaatgtatgt 540
agattgcgta tatagtttcg tctaccctat gaacatattc cattttgtaa tttcgtgtcg 600
tttctattat gaatttcatt tataaagttt atgtacaaat atcataaaaa aagagaatct 660
ttttaagcaa ggattttctt aacttcttcg gcgacagcat caccgacttc ggtggtactg 720
ttggaaccac ctaaatcacc agttctgata cctgcatcca aaaccttttt aactgcatct 780
tcaatggcct taccttcttc aggcaagttc aatgacaatt tcaacatcat tgcagcagac 840
aagatagtgg cgatagggtc aaccttattc tttggcaaat ctggagcaga accgtggcat 900
ggttcgtaca aaccaaatgc ggtgttcttg tctggcaaag aggccaagga cgcagatggc 960
aacaaaccca aggaacctgg gataacggag gcttcatcgg agatgatatc accaaacatg 1020
ttgctggtga ttataatacc atttaggtgg gttgggttct taactaggat catggcggca 1080
gaatcaatca attgatgttg aaccttcaat gtagggaatt cgttcttgat ggtttcctcc 1140
acagtttttc tccataatct tgaagaggcc aaaacattag ctttatccaa ggaccaaata 1200
ggcaatggtg gctcatgttg tagggccatg aaagcggcca ttcttgtgat tctttgcact 1260
tctggaacgg tgtattgttc actatcccaa gcgacaccat caccatcgtc ttcctttctc 1320
ttaccaaagt aaatacctcc cactaattct ctgacaacaa cgaagtcagt acctttagca 1380
aattgtggct tgattggaga taagtctaaa agagagtcgg atgcaaagtt acatggtctt 1440
aagttggcgt acaattgaag ttctttacgg atttttagta aaccttgttc aggtctaaca 1500
ctaccggtac cccatttagg accacccaca gcacctaaca aaacggcatc aaccttcttg 1560
gaggcttcca gcgcctcatc tggaagtggg acacctgtag catcgatagc agcaccacca 1620
attaaatgat tttcgaaatc gaacttgaca ttggaacgaa catcagaaat agctttaaga 1680
accttaatgg cttcggctgt gatttcttga ccaacgtggt cacctggcaa aacgacgatc 1740
ttcttagggg cagacatagg ggcagacatt agaatggtat atccttgaaa tatatatata 1800
tattgctgaa atgtaaaagg taagaaaagt tagaaagtaa gacgattgct aaccacctat 1860
tggaaaaaac aataggtcct taaataatat tgtcaacttc aagtattgtg atgcaagcat 1920

-continued

```
ttagtcatga acgcttctct attctatatg aaaagccggt tccggcctct cacctttcct   1980
ttttctccca atttttcagt tgaaaaaggt atatgcgtca ggcgacctct gaaattaaca   2040
aaaaatttcc agtcatcgaa tttgattctg tgcgatagcg cccctgtgtg ttctcgttat   2100
gttgaggaaa aaaataatgg ttgctaagag attcgaactc ttgcatctta cgatacctga   2160
gtattcccac agttaactgc ggtcaagata tttcttgaat caggcgcctt agaccgctcg   2220
gccaaacaac caattacttg ttgagaaata gagtataatt atcctataaa tataacgttt   2280
ttgaacacac atgaacaagg aagtacagga caattgattt tgaagagaat gtggattttg   2340
atgtaattgt tgggattcca tttttaataa ggcaataata ttaggtatgt ggatatacta   2400
gaagttctcc tcgaccgtcg atatgcggtg tgaaataccg cacagatgcg taaggagaaa   2460
ataccgcatc aggaaattgt aaacgttaat attttgttaa aattcgcgtt aaatttttgt   2520
taaatcagct cattttttaa ccaataggcc gaaatcggca aaatccctta taaatcaaaa   2580
gaatagaccg agatagggtt gagtgttgtt ccagtttgga acaagagtcc actattaaag   2640
aacgtggact ccaacgtcaa agggcgaaaa accgtctatc agggcgatgg cccactacgt   2700
gaaccatcac cctaatcaag ttttttgggg tcgaggtgcc gtaaagcact aaatcggaac   2760
cctaaaggga gcccccgatt tagagcttga cggggaaagc cggcgaacgt ggcgagaaag   2820
gaagggaaga aagcgaaagg agcgggcgct agggcgctgg caagtgtagc ggtcacgctg   2880
cgcgtaacca ccacacccgc cgcgcttaat gcgccgctac agggcgcgtc gcgccattcg   2940
ccattcaggc tgcgcaactg ttgggaaggg cgatcggtgc gggcctcttc gctattacgc   3000
cagctggcga aagggggatg tgctgcaagg cgattaagtt gggtaacgcc agggttttcc   3060
cagtcacgac gttgtaaaac gacggccagt gagcgcgcgt aatacgactc actatagggc   3120
gaattgggta ccgggccccc cctcgaggtc gacggtatcg ataagcttga tatcgaattc   3180
ctgcagcccg ggggatccac tagttctaga gcggccgcca ccgcggtgga gctccagctt   3240
ttgttccctt tagtgagggt taattgcgcg cttggcgtaa tcatggtcat agctgtttcc   3300
tgtgtgaaat tgttatccgc tcacaattcc acacaacata ggagccggaa gcataaagtg   3360
taaagcctgg ggtgcctaat gagtgaggta actcacatta attgcgttgc gctcactgcc   3420
cgctttccag tcgggaaacc tgtcgtgcca gctgcattaa tgaatcggcc aacgcgcggg   3480
gagaggcggt ttgcgtattg ggcgctcttc cgcttcctcg ctcactgact cgctgcgctc   3540
ggtcgttcgg ctgcggcgag cggtatcagc tcactcaaag gcggtaatac ggttatccac   3600
agaatcaggg gataacgcag gaaagaacat gtgagcaaaa ggccagcaaa aggccaggaa   3660
ccgtaaaaag gccgcgttgc tggcgttttt ccataggctc cgcccccctg acgagcatca   3720
caaaaatcga cgctcaagtc agaggtggcg aaacccgaca ggactataaa gataccaggc   3780
gtttccccct ggaagctccc tcgtgcgctc tcctgttccg accctgccgc ttaccggata   3840
cctgtccgcc tttctccctt cgggaagcgt ggcgctttct catagctcac gctgtaggta   3900
tctcagttcg gtgtaggtcg ttcgctccaa gctgggctgt gtgcacgaac cccccgttca   3960
gcccgaccgc tgcgccttat ccggtaacta tcgtcttgag tccaacccgg taagacacga   4020
cttatcgcca ctggcagcag ccactggtaa caggattagc agagcgaggt atgtaggcgg   4080
tgctacagag ttcttgaagt ggtggcctaa ctacggctac actagaagga cagtatttgg   4140
tatctgcgct ctgctgaagc cagttacctt cggaaaaaga gttggtagct cttgatccgg   4200
caaacaaacc accgctggta gcggtggttt ttttgtttgc aagcagcaga ttacgcgcag   4260
aaaaaaagga tctcaagaag atcctttgat cttttctacg ggtctgacg ctcagtggaa   4320
```

cgaaaactca cgttaaggga ttttggtcat gagattatca aaaaggatct tcacctagat 4380
ccttttaaat taaaaatgaa gttttaaatc aatctaaagt atatatgagt aaacttggtc 4440
tgacagttac caatgcttaa tcagtgaggc acctatctca gcgatctgtc tatttcgttc 4500
atccatagtt gcctgactcc ccgtcgtgta gataactacg atacgggagg gcttaccatc 4560
tggccccagt gctgcaatga taccgcgaga cccacgctca ccggctccag atttatcagc 4620
aataaaccag ccagccggaa gggccgagcg cagaagtggt cctgcaactt tatccgcctc 4680
catccagtct attaattgtt gccgggaagc tagagtaagt agttcgccag ttaatagttt 4740
gcgcaacgtt gttgccattg ctacaggcat cgtggtgtca cgctcgtcgt ttggtatggc 4800
ttcattcagc tccggttccc aacgatcaag gcgagttaca tgatccccca tgttgtgcaa 4860
aaaagcggtt agctccttcg gtcctccgat cgttgtcaga agtaagttgg ccgcagtgtt 4920
atcactcatg gttatggcag cactgcataa ttctcttact gtcatgccat ccgtaagatg 4980
cttttctgtg actggtgagt actcaaccaa gtcattctga gaatagtgta tgcggcgacc 5040
gagttgctct tgcccggcgt caatacggga taataccgcg ccacatagca gaactttaaa 5100
agtgctcatc attggaaaac gttcttcggg gcgaaaactc tcaaggatct taccgctgtt 5160
gagatccagt tcgatgtaac ccactcgtgc acccaactga tcttcagcat cttttacttt 5220
caccagcgtt tctgggtgag caaaaacagg aaggcaaaat gccgcaaaaa agggaataag 5280
ggcgacacgg aaatgttgaa tactcatact cttccttttt caatattatt gaagcattta 5340
tcagggttat tgtctcatga gcggatacat atttgaatgt atttagaaaa ataaacaaat 5400
aggggttccg cgcacatttc cccgaaaagt gccacctggg tccttttcat cacgtgctat 5460
aaaaataatt ataatttaaa tttttttaata taaatatata aattaaaaat agaaagtaaa 5520
aaaagaaatt aaagaaaaaa tagtttttgt tttccgaaga tgtaaaagac tctaggggga 5580
tcgccaacaa atactacctt ttatcttgct cttcctgctc tcaggtatta atgccgaatt 5640
gtttcatctt gtctgtgtag aagaccacac acgaaaatcc tgtgatttta cattttactt 5700
atcgttaatc gaatgtatat ctatttaatc tgcttttctt gtctaataaa tatatatgta 5760
aagtacgctt tttgttgaaa ttttttaaac ctttgtttat ttttttttct tcattccgta 5820
actcttctac cttctttatt tactttctaa aatccaaata caaaacataa aaataaataa 5880
acacagagta aattcccaaa ttattccatc attaaaagat acgaggcgcg tgtaagttac 5940
aggcaagcga tccgtcctaa gaaaccatta ttatcatgac attaacctat aaaaataggc 6000
gtatcacgag gccctttcgt c 6021

<210> SEQ ID NO 71
<211> LENGTH: 501
<212> TYPE: DNA
<213> ORGANISM: Artificial sequence
<220> FEATURE:
<223> OTHER INFORMATION: Synthesized: pTDH3 (promoter)

<400> SEQUENCE: 71
aacagtttat tcctggcatc cactaaatat aatggagccc gctttttaag ctggcatcca 60
gaaaaaaaaa gaatcccagc accaaaatat tgttttcttc accaaccatc agttcatagg 120
tccattctct tagcgcaact acagagaaca ggggcacaaa caggcaaaaa acgggcacaa 180
cctcaatgga gtgatgcaac ctgcctggag taaatgatga cacaaggcaa ttgacccacg 240
catgtatcta tctcattttc ttacaccttc tattaccttc tgctctctct gatttggaaa 300
aagctgaaaa aaaaggttga aaccagttcc ctgaaattat tcccctactt gactaataag 360
tatataaaga cggtaggtat tgattgtaat tctgtaaatc tatttcttaa acttcttaaa 420
ttctactttt atagttagtc tttttttag ttttaaaaca ccaagaactt agtttcgaat 480
aaacacacat aaacaaacaa a 501

<210> SEQ ID NO 72
<211> LENGTH: 427
<212> TYPE: DNA
<213> ORGANISM: Artificial sequence
<220> FEATURE:
<223> OTHER INFORMATION: Synthesized: pTEF1 (promoter)

<400> SEQUENCE: 72
gatcccccac acaccatagc ttcaaaatgt ttctactcct tttttactct tccagatttt 60
ctcggactcc gcgcatcgcc gtaccacttc aaaacaccca agcacagcat actaaatttc 120
ccctctttct tcctctaggg tgtcgttaat tacccgtact aaaggtttgg aaaagaaaaa 180
agacaccgcc tcgtttcttt ttcttcgtcg aaaaaggcaa taaaaatttt tatcacgttt 240
ctttttcttg aaaatttttt tttttgattt ttttctcttt cgatgacctc ccattgatat 300
ttaagttaat aaacggtgtt caatttctca agtttcagtt tcatttttct tgttctatta 360
caactttttt tacttcttgc tcattagaaa gaaagcatag caatctaatc taagttttaa 420
ttacaaa 427

<210> SEQ ID NO 73
<211> LENGTH: 201
<212> TYPE: DNA
<213> ORGANISM: Artificial sequence
<220> FEATURE:
<223> OTHER INFORMATION: Synthesized: terminator sequence tTDH3

<400> SEQUENCE: 73
gtgaatttac tttaaatctt gcatttaaat aaattttctt tttatagctt tatgacttag 60
tttcaattta tatactattt taatgacatt ttcgattcat tgattgaaag ctttgtgttt 120
tttcttgatg cgctattgca ttgttcttgt ctttttcgcc acatgtaata tctgtagtag 180
atacctgata cattgtggat g 201

<210> SEQ ID NO 74
<211> LENGTH: 157
<212> TYPE: DNA
<213> ORGANISM: Artificial sequence
<220> FEATURE:
<223> OTHER INFORMATION: Synthesized: terminator sequence tADH1

<400> SEQUENCE: 74
ataagttata aaaaaaataa gtgtatacaa attttaaagt gactcttagg ttttaaaacg 60
aaaattcttg ttcttgagta actctttcct gtaggtcagg ttgctttctc aggtatagca 120
tgaggtcgct cttattgacc acacctctac cggcatg 157

<210> SEQ ID NO 75
<211> LENGTH: 199
<212> TYPE: DNA
<213> ORGANISM: Artificial sequence
<220> FEATURE:
<223> OTHER INFORMATION: Synthesized: terminator sequence tTEF1

<400> SEQUENCE: 75
ggagattgat aagacttttc tagttgcata tcttttatat ttaaatctta tctattagtt 60

-continued

```
aattttttgt aatttatcct tatatatagt ctggttattc taaaatatca tttcagtatc    120

taaaaattcc cctctttttt cagttatatc ttaacaggcg acagtccaaa tgttgattta    180

tcccagtccg attcatcag                                                 199


<210> SEQ ID NO 76
<211> LENGTH: 60
<212> TYPE: DNA
<213> ORGANISM: Artificial sequence
<220> FEATURE:
<223> OTHER INFORMATION: Synthesized: primer BK01008

<400> SEQUENCE: 76

gaacaagtaa tagtggtgac tgcaggttac gttggcatat ataacttcgt ataatgtatg     60


<210> SEQ ID NO 77
<211> LENGTH: 60
<212> TYPE: DNA
<213> ORGANISM: Artificial sequence
<220> FEATURE:
<223> OTHER INFORMATION: Synthesized: primer BK01009

<400> SEQUENCE: 77

ttaattgaga atacggttga cctggcatgt tgttcgaatc ataacttcgt ataatgtatg     60


<210> SEQ ID NO 78
<211> LENGTH: 60
<212> TYPE: DNA
<213> ORGANISM: Artificial sequence
<220> FEATURE:
<223> OTHER INFORMATION: Synthesized: primer BK01016

<400> SEQUENCE: 78

gatatgtatt attcttcaaa acattctctt gttcttgtgc aattcccgtt ttaagagctt     60


<210> SEQ ID NO 79
<211> LENGTH: 60
<212> TYPE: DNA
<213> ORGANISM: Artificial sequence
<220> FEATURE:
<223> OTHER INFORMATION: Synthesized: primer BK01017

<400> SEQUENCE: 79

cattttcaat ggtttggagg tattctttga aatcataaag tcgagttcaa gagaaaaaaa     60
```

MODIFIED MICROORGANISMS COMPRISING AN OPTIMIZED SYSTEM FOR OLIGOSACCHARIDE UTILIZATION AND METHODS OF USING SAME

FIELD

The present disclosure generally relates to modified microorganisms (e.g., non-naturally occurring microorganisms) that comprise one or more polynucleotides coding for proteins and enzymes in a pathway that optimizes the microorganism's utilization of oligosaccharides.

BACKGROUND

For many years, the chemical industry has been using coal, gas, and oil to produce the vast majority of its industrial products. However, with diminishing supplies of these resources and the looming dangers of excessive carbon dioxide emissions, there is a dire need to develop sustainable and renewable chemicals that can produce the same products in a safe and cost effective way.

To address the need to develop sustainable and renewal chemical resources, companies have begun using genetically modified microorganisms to convert carbon sources to chemicals, such as terpenes, that can be used to produce industrial products. Typically, this conversion is carried out by fermentation of the carbon source under anaerobic conditions. Use of this process provides a sustainable, renewable source of chemicals for use in industrial applications.

Oligosaccharides are frequently used as a carbon source or feedstock to fuel the fermentation or other metabolic process used to produce the desired chemicals. However, the efficiency of the chemical producing process is limited by the genetically modified microorganisms' ability to efficiently utilize the carbon source provided.

All known natural and currently employed heterologous oligosaccharide utilization systems lose energy during transport of the oligosaccharide into the microorganism or during cleavage of the oligosaccharide. This loss of energy reduces the efficiency of the microorganisms' production of chemicals, which in turn increases the cost and time of production.

Given the demand for sustainable, renewable sources of chemicals and the resulting increased use of genetically modified microorganisms to produce industrially useful chemicals, more efficient microorganisms are needed. In particular, methods for optimizing microorganisms' utilization of oligosaccharides to reduce the time and expense of producing chemicals is desired, particularly in anaerobic environments.

SUMMARY

The present disclosure generally relates to microorganisms (e.g., non-naturally occurring microorganisms) having an optimized system (e.g., a genetically modified pathway for increasing microorganisms' adenosine triphosphate (ATP) production from utilization (e.g. metabolism) of oligosaccharides when compared to microorganisms lacking this genetically modified pathway) for oligosaccharide utilization that comprise one or more polynucleotides coding for an energy independent oligosaccharide transporter for transporting an oligosaccharide into the microorganism; one or more polynucleotides coding for a phosphorylase for catalyzing the conversion of the oligosaccharide into at least one phosphorylated saccharide; and one or more polynucleotides coding for a phosphoglucomutase for catalyzing the conversion of the phosphorylated saccharide into an isomer of the phosphorylated saccharide, wherein the isomer of the phosphorylated saccharide is utilized in one or more enzymatic pathways in the microorganism. Optionally, the methods may further comprise knocking-out (i.e., deleting) one or more naturally competing transporter systems (e.g., one or more nucleotides coding for one or more proteins involved in the transporter system) for transporting the oligosaccharide into the microorganism. Alternatively, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

The present disclosure also provides a method of optimizing utilization of an oligosaccharide in a microorganism that comprises providing an oligosaccharide source; expressing one or more polynucleotides in the microorganism that encode an energy independent oligosaccharide transporter for transporting the oligosaccharide into the microorganism; expressing one or more polynucleotides in the microorganism that encode a phosphorylase for catalyzing a conversion of the oligosaccharide into at least one phosphorylated saccharide; expressing one or more polynucleotides in the microorganism that encode a phosphoglucomutase for catalyzing a conversion of the phosphorylated saccharide into an isomer of the phosphorylated saccharide, wherein the isomer of the phosphorylated saccharide is utilized in one or more enzymatic pathways in the microorganism; and contacting the oligosaccharide source with the microorganism. Optionally, the methods may further comprise knocking-out (i.e., deleting) one or more naturally competing transporter systems (e.g., one or more nucleotides coding for one or more proteins involved in the transporter system) for transporting the oligosaccharide into the microorganism. Alternatively, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out. In some embodiments of each or any of the above or below mentioned embodiments, the oligosaccharide source is sugar cane juice. In some embodiments of each or any of the above or below mentioned embodiments the oligosaccharide source is sucrose. In some embodiments of each or any of the above or below mentioned embodiments the oligosaccharide source is maltose. In some embodiments of each or any of the above or below mentioned embodiments the oligosaccharide source is cellobiose. In some embodiments of each or any of the above or below mentioned embodiments, the oligosaccharide source is selected from the group consisting of: lactose, lactulose, isomaltose, melibiose, and trehalose.

In some embodiments of each or any of the above or below mentioned embodiments, the microorganism is a bacteria selected from the genera consisting essentially of: *Propionibacterium, Propionispira, Clostridium, Bacillus, Escherichia, Pelobacter*, or *Lactobacillus.*

In some embodiments of each or any of the above or below mentioned embodiments, the microorganism is a eukaryote selected from the group consisting essentially of a yeast, filamentous fungi, protozoa, or algae.

In some embodiments of each or any of the above or below mentioned embodiments, the microorganism is from a genus selected from the group consisting of: *Saccharomyces, Yarrowia, Hansenula, Pichia, Ashbya*, and *Candida.*

In some embodiments of each or any of the above or below mentioned embodiments, the energy independent oligosaccharide transporter is from a class selected from the group consisting of: sugars will eventually be exported transporter (SWEET) proteins, sucrose binding proteins (SBP), sucrose uptake facilitators (SUF), cellodextrin facilitators and aquaporins.

In some embodiments of each or any of the above or below mentioned embodiments, the polynucleotides encoding the phosphorylase are genes selected from the group consisting of: sucrose phosphorylase genes, such as spl of *Bifidobacterium adolescent* and sucP (742sp) of *Leuconostoc mesenteroides*; and maltose phosphorylase genes, such as LVIS_0358 of *Lactobacillus brevis* and mapA of *Lactobacillus sanfranciscensis*; cellobiose phosphorylase genes, such as cbp from *Clostridium thermocellum.*

In some embodiments of each or any of the above or below mentioned embodiments, the phosphoglucomutase is selected from the group consisting of: α-phosphoglucomutase and β-phosphoglucomutase. In some embodiments of each or any of the above or below mentioned embodiments, the phosphoglucomutase is selected from the group consisting of: pgm1 and pgm2 from *Saccharomyces cerevisiae*, pgmA from *Lactobacillus sanfrancisco*, and pgmB from *Lactococcus lactis.*

In some embodiments of each or any of the above or below mentioned embodiments, the isomer is converted to pyruvate via glycolysis.

In some embodiments of each or any of the above or below mentioned embodiments, the isomer is utilized in an anaerobic metabolic pathway.

In some embodiments of each or any of the above or below mentioned embodiments, the utilization of the isomer yields an increased amount of adenosine triphosphate (ATP).

In some embodiments of each or any of the above or below mentioned embodiments, the isomer of the phosphorylated saccharide is utilized in a pathway for the production of an organic molecule.

In some embodiments of each or any of the above or below mentioned embodiments, the utilization being optimized is the fermentation of di-saccharides. In some embodiments of each or any of the above or below mentioned embodiments, the ATP production resulting from di-saccharide fermentation is increased by at least 25% at 100% efficiency of the optimized oligo-saccharide uptake system. In some embodiments of each or any of the above or below mentioned embodiments, the increased yield of ATP results in an increased yield of organic molecules produced as a result of the microorganism's metabolism.

In some embodiments of each or any of the above or below mentioned embodiments, the oligosaccharide source is contacted with the microorganism prior to expressing one or more polynucleotides in the microorganism that encode an energy independent oligosaccharide transporter for transporting the oligosaccharide into the microorganism; expressing one or more polynucleotides in the microorganism that encode a phosphorylase for catalyzing a conversion of the oligosaccharide into at least one phosphorylated saccharide; and expressing one or more polynucleotides in the microorganism that encode a phosphoglucomutase for catalyzing a conversion of the phosphorylated saccharide into an isomer of the phosphorylated saccharide, wherein the isomer of the phosphorylated saccharide is utilized in one or more enzymatic pathways in the microorganism.

In some embodiments of each or any of the above or below mentioned embodiments, the isomer of the phosphorylated saccharide is utilized in a pathway for the production of an organic molecule.

The present disclosure also provides a microorganism having an optimized system for oligosaccharide utilization comprising one or more polynucleotides coding for an energy independent oligosaccharide transporter for transporting an oligosaccharide into the microorganism; one or more polynucleotides coding for a phosphorylase for catalyzing the conversion of the oligosaccharide into at least one phosphorylated saccharide; and one or more polynucleotides coding for a phosphoglucomutase for catalyzing the conversion of the phosphorylated saccharide into an isomer of the phosphorylated saccharide, wherein the isomer of the phosphorylated saccharide is utilized in one or more enzymatic pathways in the microorganism. Optionally, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

The present disclosure also provides a method of optimizing utilization of sucrose in a microorganism comprising: providing sucrose; expressing one or more polynucleotides in the microorganism that encode an energy independent oligosaccharide transporter for transporting the sucrose into the microorganism; expressing one or more polynucleotides in the microorganism that encode a phosphorylase for catalyzing a conversion of the sucrose into glucose-1-phosphate and fructose; expressing one or more polynucleotides in the microorganism that encode a phosphoglucomutase for catalyzing a conversion of the glucose-1-phosphate into glucose-6-phosphate, wherein the glucose-6-phosphate is utilized in one or more enzymatic pathways in the microorganism; and contacting the sucrose with the microorganism. Optionally, the methods may further comprise knocking-out (i.e., deleting) one or more naturally competing transporter systems (e.g., one or more nucleotides coding for one or more proteins involved in the transporter system) for transporting the oligosaccharide into the microorganism. Alternatively, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

The present disclosure also provides a microorganism having an optimized system for sucrose utilization comprising one or more polynucleotides coding for an energy independent oligosaccharide transporter for transporting sucrose into the microorganism; one or more polynucleotides coding for a phosphorylase for catalyzing the conversion of the sucrose into glucose-1-phosphate and fructose; and one or more polynucleotides coding for a phosphoglucomutase for catalyzing the conversion of the glucose-1-phosphate into glucose-6-phosphate, wherein the glucose-6-phosphate is utilized in one or more enzymatic pathways in the microorganism. Optionally, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

The present disclosure also provides a method of optimizing utilization of maltose in a microorganism comprising: providing maltose; expressing one or more polynucleotides in the microorganism that encode an energy independent oligosaccharide transporter for transporting the maltose into the microorganism; expressing one or more polynucleotides in the microorganism that encode a phosphorylase for catalyzing a conversion of the maltose into glucose-1-phosphate and glucose; expressing one or more polynucleotides in the microorganism that encode a phosphoglucomutase for catalyzing a conversion of the glucose-1-phosphate into glucose-6-phosphate, wherein the glucose-6-phosphate is utilized in one or more enzymatic pathways in the microorganism; and contacting the maltose with the microorganism. Optionally, the methods may further comprise knocking-out (i.e., deleting) one or more naturally competing transporter systems (e.g., one or more nucleotides coding for one or more proteins involved in the transporter system) for transporting the oligosaccharide into the microorganism. Alternatively, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

The present disclosure also provides a microorganism having an optimized system for maltose utilization comprising one or more polynucleotides coding for an energy independent oligosaccharide transporter for transporting maltose into the microorganism; one or more polynucleotides coding for a phosphorylase for catalyzing the conversion of the maltose into glucose-1-phosphate and glucose; and one or more polynucleotides coding for a phosphoglucomutase for catalyzing the conversion of the glucose-1-phosphate into glucose-6-phosphate, wherein the glucose-6-phosphate is utilized in one or more enzymatic pathways in the microorganism. Optionally, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

The present disclosure also provides a method optimizing utilization of cellobiose in a microorganism comprising: providing cellobiose; expressing one or more polynucleotides in the microorganism that encode an energy independent oligosaccharide transporter for transporting the cellobiose into the microorganism; expressing one or more polynucleotides in the microorganism that encode a phosphorylase for catalyzing a conversion of the cellobiose into glucose-1-phosphate and glucose; expressing one or more polynucleotides in the microorganism that encode a phosphoglucomutase for catalyzing a conversion of the glucose-1-phosphate into glucose-6-phosphate, wherein the glucose-6-phosphate is utilized in one or more enzymatic pathways in the microorganism; and contacting the cellobiose with the microorganism. Optionally, the methods may further comprise knocking-out (i.e., deleting) one or more naturally competing transporter systems (e.g., one or more nucleotides coding for one or more proteins involved in the transporter system) for transporting the oligosaccharide into the microorganism. Alternatively, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

The present disclosure also provides a microorganism having an optimized system for cellobiose utilization comprising one or more polynucleotides coding for an energy independent oligosaccharide transporter for transporting cellobiose into the microorganism; one or more polynucleotides coding for a phosphorylase for catalyzing the conversion of the cellobiose into glucose-1-phosphate and glucose; and one or more polynucleotides coding for a phosphoglucomutase for catalyzing the conversion of the glucose-1-phosphate into glucose-6-phosphate, wherein the glucose-6-phosphate is utilized in one or more enzymatic pathways in the microorganism. Optionally, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

The present disclosure also provides a method of optimizing utilization of an oligosaccharide in a microorganism to produce an organic molecule comprising: providing an oligosaccharide source; expressing one or more polynucleotides in the microorganism that encode an energy independent oligosaccharide transporter for transporting the oligosaccharide into the microorganism; expressing one or more polynucleotides in the microorganism that encode a phosphorylase for catalyzing a conversion of the oligosaccharide into at least one phosphorylated saccharide; expressing one or more polynucleotides in the microorganism that encode a phosphoglucomutase for catalyzing a conversion of the phosphorylated saccharide into a an isomer of the phosphorylated saccharide; expressing one or more polynucleotides in the microorganism for catalyzing a conversion of the isomer into an organic molecule; and contacting the oligosaccharide source with the microorganism. Optionally, the methods may further comprise knocking-out (i.e., deleting) one or more naturally competing transporter systems (e.g., one or more nucleotides coding for one or more proteins involved in the transporter system) for transporting the oligosaccharide into the microorganism. Alternatively, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

In some embodiments of each or any of the above or below mentioned embodiments, the organic molecule is selected from the group consisting of: acid, alcohol, alkane, alkene, amide, amine, amino acid, aromatic, carbohydrate, diacid, dialcohol, diene, ester (incl. waxes), ether, fat (incl. oils), fatty acid, fatty alcohol, ketone, lactam, peptide, protein, steroid, terpene, vitamin.

In some embodiments of each or any of the above or below mentioned embodiments, the organic molecule is selected from the group consisting of: acetic acid, acrylic acid, 3-hydroxypropionic acid, lactic acid, methacrylic acid; ethanol, isopropanol, 1-propanol, 2-propanol, n-butanol, isobutanol; hexene, propene; hexamethylenediamine; adipic acid, glucaric acid, itaconic acid, malonic acid, succinic acid; 1,2-ethandiol (ethylene glycol), butanediol, 1,4-butanediol, 1,2-propanediol (monopropylen glycol), 1,3-propanediol; butadiene; methyl methacrylate; caprolactam; isoprene, farnesene.

The present disclosure also provides a method of increasing the yield of an organic molecule produced by a microorganism under anaerobic conditions comprising: providing an oligosaccharide source for use by the microorganism; expressing one or more polynucleotides in the microorganism that encode an energy independent oligosaccharide transporter for transporting the oligosaccharide into the microorganism; expressing one or more polynucleotides in the microorganism that encode a phosphorylase for catalyzing a conversion of the oligosaccharide into at least one phosphorylated saccharide; expressing one or more polynucleotides in the microorganism that encode a phosphoglucomutase for catalyzing a conversion of the phosphorylated saccharide into an isomer of the phosphorylated saccharide; expressing one or more polynucleotides in the microorganism for catalyzing a conversion of the isomer into an organic molecule; and contacting the oligosaccharide source with the microorganism.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments that are presently preferred. It should be understood, however, that the disclosure is not limited to the precise arrangements, examples and instrumentalities shown.

DETAILED DESCRIPTION

Figure 1:
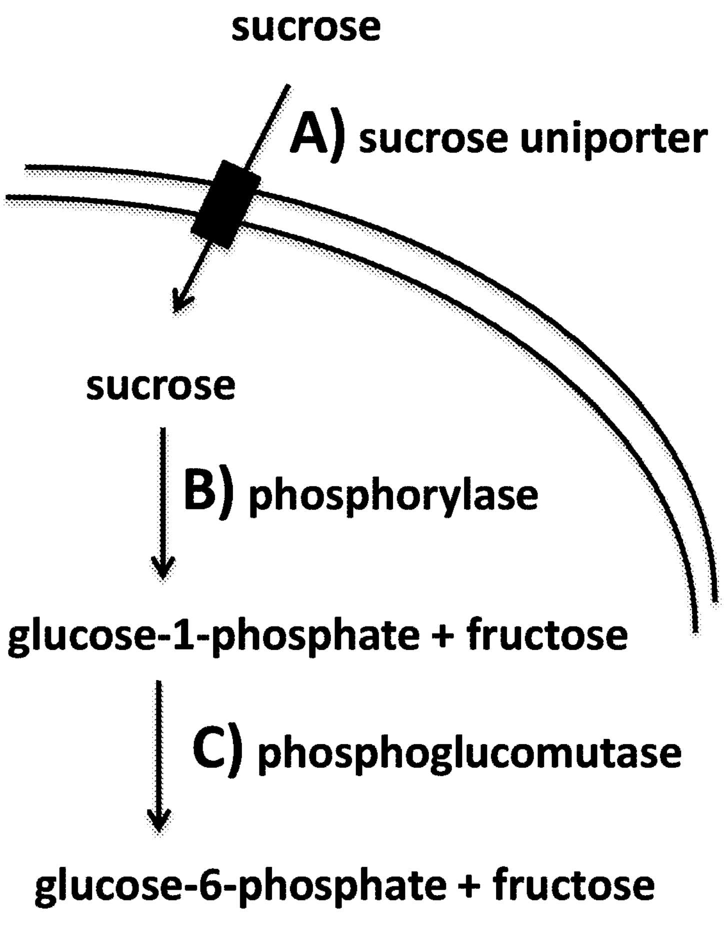
FIG. 1 depicts an exemplary oligosaccharide utilization system wherein the oligosaccharide being utilized is sucrose.

The present disclosure generally relates to microorganisms (e.g., non-naturally occurring microorganisms) that comprise a genetically modified pathway for optimizing the microorganisms' utilization of oligosaccharides (e.g., an oligosaccharide utilization system) (see, FIG. 1). Such microorganisms can comprise one or more polynucleotides coding for one or more energy independent oligosaccharide transporters for transporting an oligosaccharide into the microorganism. Optionally, the microorganism can be further modified to comprise one or more polynucleotides coding for enzymes (e.g., phosphorylase) that catalyze the conversion (e.g., phosphorolysis) of the oligosaccharide into at least one phosphorylated saccharide, and one or more polynucleotides coding for enzymes (e.g., phosphoglucomutase) that catalyze the conversion of the phosphorylated saccharide into an isomer of the phosphorylated saccharide, wherein the isomer of the phosphorylated saccharide is utilized (e.g., metabolized) in one or more enzymatic pathways in the microorganism for the production of an organic molecule such as a acetic acid, acrylic acid, 3-hydroxypropionic acid, lactic acid, etc. The microorganism can be genetically modified to include polynucleotides coding for one or more energy independent oligosaccharide transporters, either in the presence of or in the absence of naturally occurring energy independent oligosaccharide transporters. Similarly, the microorganism can also be genetically modified to include polynucleotides coding for phosphorylases and/or phosphoglucomutases in addition to an oligosaccharide transporter, either in the presence or absence of naturally occurring phosphorylases and phosphoglucomutases.

Optionally, the methods may further comprise knocking-out (i.e., deleting) one or more naturally competing transporter systems (e.g., one or more nucleotides coding for one or more proteins involved in the transporter system) for transporting the oligosaccharide into the microorganism. Alternatively, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

In an embodiment, the microorganism comprises one or more polynucleotides coding for one or more energy independent oligosaccharide transporters for transporting an oligosaccharide into the microorganism, one or more polynucleotides coding for enzymes that catalyze the conversion of the oligosaccharide into at least one phosphorylated saccharide, and one or more polynucleotides coding for enzymes that catalyze the conversion of the phosphorylated saccharide into an isomer of the phosphorylated saccharide, wherein the isomer of the phosphorylated saccharide is utilized in one or more enzymatic pathways in the microorganism for the production of an organic molecule such as acetic acid, acrylic acid, 3-hydroxypropionic acid, lactic acid, etc.

In a preferred embodiment, the microorganism comprises one or more polynucleotides coding for a plant energy independent oligosaccharide transporter for transporting an oligosaccharide into the microorganism, and one or more polynucleotides coding for a bacterial phosphorylase for catalyzing the conversion of the oligosaccharide into at least one phosphorylated saccharide, wherein the phosphorylated saccharide is utilized in one or more naturally occurring or genetically modified enzymatic pathways in the microorganism for production of an organic molecule.

In some embodiments, the microorganism is genetically modified to comprise one or more polynucleotides coding for one or more energy independent oligosaccharide transporters, one or more polynucleotides coding for enzymes that catalyze the conversion of the oligosaccharide into at least one phosphorylated saccharide, and one or more polynucleotides coding for enzymes that catalyze the conversion of the phosphorylated saccharide into an isomer of the phosphorylated saccharide, wherein the isomer of the phosphorylated saccharide is utilized in one or more enzymatic pathways in the microorganism for the production of an organic molecule such as acetic acid, acrylic acid, 3-hydroxypropionic acid, lactic acid, etc. In other embodiments, one or more polynucleotides coding for one or more energy independent oligosaccharide transporters, enzymes that catalyze the conversion of the oligosaccharide into at least one phosphorylated saccharide, and enzymes that catalyze the conversion of the phosphorylated saccharide into an isomer can be naturally occurring in the microorganism. In some embodiments, the microorganism can contain or be genetically modified to include and also naturally contain any combination of the above-mentioned polynucleotides. Optionally, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

In another embodiment, the microorganism comprises one or more polynucleotides coding for one or more energy independent oligosaccharide transporters for transporting sucrose into the microorganism, one or more polynucleotides coding for a phosphorylase that catalyzes the conversion of the sucrose into glucose-1-phosphate and fructose, one or more polynucleotides coding for a phosphoglucomutase that catalyzes the conversion of the glucose-1-phosphate into glucose-6-phosphate, wherein the glucose-6-phosphate is utilized in one or more enzymatic pathways in the microorganism for the production of an organic molecule such as acetic acid, acrylic acid, 3-hydroxypropionic acid, lactic acid, etc. Optionally, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

In another embodiment, the microorganism comprises one or more polynucleotides coding for one or more energy independent oligosaccharide transporters for transporting maltose into the microorganism, one or more polynucleotides coding for a phosphorylase that catalyzes the conversion of the maltose into glucose-1-phosphate and glucose, one or more polynucleotides coding for a phosphoglucomutase that catalyzes the conversion of the glucose-1-phosphate into glucose-6-phosphate, wherein the glucose-6-phosphate is utilized in one or more enzymatic pathways in the microorganism for the production of an organic molecule such as acetic acid, acrylic acid, 3-hydroxypropionic acid, lactic acid, etc. Optionally, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

In another embodiment, the microorganism comprises one or more polynucleotides coding for one or more energy independent oligosaccharide transporters for transporting cellobiose into the microorganism, one or more polynucleotides coding for a phosphorylase that catalyzes the conversion of the cellobiose into glucose-1-phosphate and glucose, one or more polynucleotides coding for a phosphoglucomutase that catalyzes the conversion of the glucose-1-phosphate into glucose-6-phosphate, wherein the glucose-6-phosphate is utilized in one or more enzymatic pathways in the microorganism for the production of an organic molecule such as acetic acid, acrylic acid, 3-hydroxypropionic acid, lactic acid etc. Optionally, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

This disclosure provides, in part, the discovery of a novel system for optimized oligosaccharide utilization that does not require the use of energy during oligosaccharide uptake. Such a system has not previously been used to optimize oligosaccharide utilization.

The use of energy independent, gradient driven oligosaccharide transporters, also referred to as uniporters, in the oligosaccharide utilization system conserves energy during oligosaccharide uptake by the microorganism by not requiring the use of adenosine triphosphate (ATP). Most known oligosaccharide transporters, such as ATP-binding cassette (ABC) type transporters, phosphotransferase (PTS) based importers (PEP based importers), or proton symporters, require the use of ATP for oligosaccharide uptake.

No currently known energy independent oligosaccharide transporters of microbial origin have been identified, with the exception of the eukaryotic (yeast) cellodextrin facilitators, and none have been used to optimize oligosaccharide utilization in microorganisms. However, in plants oligosaccharide transporters have been identified that are non-PTS, do not require the use of ATP or guanosine triphosphate (GTP), are pH independent, and are not inhibited by protonophores (e.g. proton gradient uncoupling chemicals, such as dinitrophenol (DNP)). Classes of these known oligosaccharide uniporters include sugars will eventually be exported transporter (SWEET) proteins, sucrose binding proteins (SBP), sucrose uptake facilitators (SUF). Additionally, aquaporins are suspected as being potential oligosaccharide uniporters.

Although the above-mentioned proteins have been identified as uniporters or potential uniporters, none have been used in an oligosaccharide utilization system with the intent of optimizing energy conversation during oligosaccharide utilization.

Optionally, a phosphorylase can be used as part of the disclosed oligosaccharide utilization system. The phosphorylase catalyzes a conversion of the oligosaccharide (e.g., phosphorolysis) that cleaves the oligosaccharide, and during said cleavage transfers an orthophosphate ion to one of the resulting mono-saccharides. The energy in the oligosaccharide's glycolytic bond is used to create the mono-saccharide-phosphate, which conserves energy (e.g., ATP). For example, the use of a phosphorylase on a di-saccharide yields one phosphorylated mono-saccharide and one non-phosphorylated mono-saccharide, saving one ATP per di-saccharide. The phosphorylated saccharide is then utilized in one or more enzymatic pathways in the microorganism, such as glycolysis or the pentose-phosphate pathway.

The majority of known microorganisms use hydrolases to break down oligosaccharides, not phosphorylases. However, some *Lactobacilli* reportedly use a phosphorylase to utilize the energy potential in the oligosaccharide's glycolytic bond. Yet, the known *Lactobacillus* sucrose transporters all require the use of ATP, including an ATP driven ABC type importer (MsmEFGK) and a PTS energy dependent transporter (Pts1BCA). Thus, the use of a phosphorylase in the disclosed oligosaccharide utilization system was not previously known.

Optionally, a phosphoglucomutase can be used as part of the disclosed oligosaccharide utilization system. The phosphoglucomutase catalyzes a conversion of the mono-saccharide-phosphate (e.g. inverts) produced by the phosphorylase described above into a different isomer that is utilized in one or more enzymatic pathways in the microorganism (e.g., glycolysis). The type of oligosaccharide used impacts the isoform of the mono-saccharide-phosphate produced during phosphorolysis, which could require different phosphoglucomutases.

For example, phosphorylation of sucrose or maltose yields D-glucose and α-D-glucose-1-phosphate or β-D-glucose-1-phosphate, respectively. In this case either an α-phosphoglucomutase or a β-phosphoglucomutase is required. In another example, phosphorylation of cellobiose yields α-D-glucose-1-phosphate and D-glucose. In this case an α-phosphoglucomutase is required.

As mentioned above, the compound produced by the phosphoglucomutase is utilized in one or more enzymatic pathways in the microorganism, such as glycolysis. Additionally, the compound can be used in any other genetically modified pathway to produce industrially useful chemicals, such as a terpene. Thus, the use of the oligosaccharide utilization system allows for the more efficient production of any chemical the microorganism has been genetically modified to produce.

In an embodiment, the disclosed oligosaccharide utilization system is used under anaerobic conditions. In another embodiment, the compound produced by either the phosphorylase or the phosphoglucomutase is utilized in an anaerobic enzymatic pathway to produce an organic molecule.

As used herein, optimizing utilization of an oligosaccharide refers to establishing energy independent oligo-saccharide transport in a genetically modified microorganism, coupled with energy conserving phosphorolysis and isomerization of the transported sugar, optionally coupled with deletion of intrinsic competing/energy dependent oligo-saccharide transport and/or energy wasting oligo-saccharide hydrolysis. Such optimization of oligosaccharide utilization in a microorganism may result in at least a 25%, 50%, 75%, 100%, or greater increase in adenosine triphosphate (ATP) production from fermentation of the oligosaccharide as compared to a microorganism in which utilization of the oligosaccharide has not been optimized.

As used herein, a system for optimized oligosaccharide utilization refers to a non-naturally occurring system comprising an energy independent oligo-saccharide transporter, an oligo-saccharide phosphorylase, and a phosphoglucomutase. Such optimized oligosaccharide utilization in a microorganism may result in at least a 25%, 50%, 75%, 100%, or greater increase in adenosine triphosphate (ATP) production from fermentation of the oligosaccharide as compared to a microorganism in which utilization of the oligosaccharide has not been optimized.

As used herein, the term "acceptor" includes but is not limited to NAD+ or NADP+ or quinone, or oxidized cytochrome c. Additionally, as used herein the term "reduced acceptor" includes but is not limited to NADH or NADPH or quinol or reduced cytochrome c.

As used herein, the term "biological activity" or "functional activity," when referring to a protein, polypeptide or peptide, may mean that the protein, polypeptide or peptide exhibits a functionality or property that is useful as relating to some biological process, pathway or reaction. Biological or functional activity can refer to, for example, an ability to interact or associate with (e.g., bind to) another polypeptide or molecule, or it can refer to an ability to catalyze or regulate the interaction of other proteins or molecules (e.g., enzymatic reactions).

As used herein, the term "culturing" may refer to growing a population of cells, e.g., microbial cells, under suitable conditions for growth, in a liquid or on solid medium.

As used herein, the term "derived from" may encompass the terms originated from, obtained from, obtainable from, isolated from, and created from, and generally indicates that one specified material finds its origin in another specified material or has features that can be described with reference to the another specified material.

As used herein, "exogenous polynucleotide" refers to any deoxyribonucleic acid that originates outside of the microorganism.

As used herein, the term "expression vector" may refer to a DNA construct containing a polynucleotide or nucleic acid sequence encoding a polypeptide or protein, such as a DNA coding sequence (e.g., gene sequence) that is operably linked to one or more suitable control sequence(s) capable of affecting expression of the coding sequence in a host. Such control sequences include a promoter to affect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome (e.g., independent vector or plasmid), or may, in some instances, integrate into the genome itself (e.g., integrated vector). The plasmid is the most commonly used form of expression vector. However, the disclosure is intended to include such other forms of expression vectors that serve equivalent functions and which are, or become, known in the art.

As used herein, the term "expression" may refer to the process by which a polypeptide is produced based on a nucleic acid sequence encoding the polypeptides (e.g., a gene). The process includes both transcription and translation.

As used herein, the term "gene" may refer to a DNA segment that is involved in producing a polypeptide or protein (e.g., fusion protein) and includes regions preceding and following the coding regions as well as intervening sequences (introns) between individual coding segments (exons).

As used herein, the term "heterologous," with reference to a nucleic acid, polynucleotide, protein or peptide, may refer to a nucleic acid, polynucleotide, protein or peptide that does not naturally occur in a specified cell, e.g., a host cell. It is intended that the term encompass proteins that are encoded by naturally occurring genes, mutated genes, and/or synthetic genes. In contrast, the term homologous, with reference to a nucleic acid, polynucleotide, protein or peptide, refers to a nucleic acid, polynucleotide, protein or peptide that occurs naturally in the cell.

As used herein, the term a "host cell" may refer to a cell or cell line, including a cell such as a microorganism which a recombinant expression vector may be transfected for expression of a polypeptide or protein (e.g., fusion protein). Host cells include progeny of a single host cell, and the progeny may not necessarily be completely identical (in morphology or in total genomic DNA complement) to the original parent cell due to natural, accidental, or deliberate mutation. A host cell may include cells transfected or transformed in vivo with an expression vector.

As used herein, the term "introduced," in the context of inserting a nucleic acid sequence or a polynucleotide sequence into a cell, may include transfection, transformation, or transduction and refers to the incorporation of a nucleic acid sequence or polynucleotide sequence into a eukaryotic or prokaryotic cell wherein the nucleic acid sequence or polynucleotide sequence may be incorporated into the genome of the cell (e.g., chromosome, plasmid, plastid, or mitochondrial DNA), converted into an autonomous replicon, or transiently expressed.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. A non-naturally occurring microbial organism of the disclosure can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely. Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

As used herein, the term "operably linked" may refer to a juxtaposition or arrangement of specified elements that allows them to perform in concert to bring about an effect. For example, a promoter may be operably linked to a coding sequence if it controls the transcription of the coding sequence.

As used herein, the term "a promoter" may refer to a regulatory sequence that is involved in binding RNA polymerase to initiate transcription of a gene. A promoter may be an inducible promoter or a constitutive promoter. An inducible promoter is a promoter that is active under environmental or developmental regulatory conditions.

As used herein, the term "a polynucleotide" or "nucleic acid sequence" may refer to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Such polynucleotides or nucleic acid sequences may encode amino acids (e.g., polypeptides or proteins such as fusion proteins). Because the genetic code is degenerate, more than one codon may be used to encode a particular amino acid, and the present disclosure encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms polynucleotide, nucleic acid, and oligonucleotide are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S (thioate), P(S)S (dithioate), $(O)NR_2$ (amidate), P(O)R, P(O)OR', $COCH_2$ (formacetal), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, the term a "protein" or "polypeptide" may refer to a composition comprised of amino acids and recognized as a protein by those of skill in the art. The conventional one-letter or three-letter code for amino acid residues is used herein. The terms protein and polypeptide are used interchangeably herein to refer to polymers of amino acids of any length, including those comprising linked (e.g., fused) peptides/polypeptides (e.g., fusion proteins). The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, related proteins, polypeptides or peptides may encompass variant proteins, polypeptides or peptides. Variant proteins, polypeptides or peptides differ from a parent protein, polypeptide or peptide and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

As used herein, the term "recovered," "isolated," "purified," and "separated" may refer to a material (e.g., a protein, peptide, nucleic acid, polynucleotide or cell) that is removed from at least one component with which it is naturally associated. For example, these terms may refer to a material which is substantially or essentially free from components which normally accompany it as found in its native state, such as, for example, an intact biological system.

As used herein, the term "recombinant" may refer to nucleic acid sequences or polynucleotides, polypeptides or proteins, and cells based thereon, that have been manipulated by man such that they are not the same as nucleic acids, polypeptides, and cells as found in nature. Recombinant may also refer to genetic material (e.g., nucleic acid sequences or polynucleotides, the polypeptides or proteins they encode, and vectors and cells comprising such nucleic acid sequences or polynucleotides) that has been modified to alter its sequence or expression characteristics, such as by mutating the coding sequence to produce an altered polypeptide, fusing the coding sequence to that of another coding sequence or gene, placing a gene under the control of a different promoter, expressing a gene in a heterologous organism, expressing a gene at decreased or elevated levels, expressing a gene conditionally or constitutively in manners different from its natural expression profile, and the like.

As used herein, the term "selective marker" or "selectable marker" may refer to a gene capable of expression in a host cell that allows for ease of selection of those hosts containing an introduced nucleic acid sequence, polynucleotide or vector. Examples of selectable markers include but are not limited to antimicrobial substances (e.g., hygromycin, bleomycin, or chloramphenicol) and/or genes that confer a metabolic advantage, such as a nutritional advantage, on the host cell.

As used herein, the term "substantially similar" and "substantially identical" in the context of at least two nucleic acids, polynucleotides, proteins or polypeptides may mean that a nucleic acid, polynucleotide, protein or polypeptide comprises a sequence that has at least about 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) nucleic acid, polynucleotide, protein or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

As used herein, the term "terpene" refers to a product having the formula $(C_5H_8)_n$. where n is 1 (i.e., isoprene), 2, 3, 4, 5, 6, 7, 8, 9, 10, or more. Terpenes may be classified by the number of isoprene units in the molecule; a prefix in the name indicates the number of terpene units needed to assemble the molecule.

Hemiterpenes consist of a single isoprene unit. Isoprene itself is considered the only hemiterpene, but oxygen-containing derivatives such as prenol and isovalericacid arehemiterpenoids.

Monoterpenes consist of two isoprene units and have the molecular formula $C_{10}H_{16}$. Examples of monoterpenes are: geraniol, limonene and terpeneol.

Sesquiterpenes consist of three isoprene units and have the molecular formula $C_{15}H_{24}$. Examples of sesquiterpenes are: humulene, farnesenes, farnesol.

Diterpenes are composed of four isoprene units and have the molecular formula $C_{20}H_{32}$. They derive from geranylgeranyl pyrophosphate. Examples of diterpenes are cafestol, kahweol, cembrene and taxadiene (precursor of taxol). Diterpenes also form the basis for biologically important compounds such as retinol, retinal, and phytol. They are known to be antimicrobial and antiinflammatory.

Sesterterpenes, terpenes having 25 carbons and five isoprene units, are rare relative to the other sizes. (The sester-prefix means half to three, i.e. two and a half.) An example of a sesterterpene is geranylfarnesol.

Triterpenes consist of six isoprene units and have the molecular formula $C_{30}H_{48}$. The linear triterpenesqualene, the major constituent of shark liver oil, is derived from the reductive coupling of two molecules of farnesyl pyrophosphate. Squalene is then processed biosynthetically to generate either lanosterol or cycloartenol, the structural precursors to all the steroids.

Sesquarterpenes are composed of seven isoprene units and have the molecular formula $C_{35}H_{56}$. Sesquarterpenes are typically microbial in their origin. Examples of sesquarterpenes are ferrugicadiol and tetraprenylcurcumene.

Tetraterpenes contain eight isoprene units and have the molecular formula $C_{40}H_{64}$. Biologically important tetraterpenes include the acyclic lycopene, the monocyclic gamma-carotene, and the bicyclic alpha- and beta-carotenes.

Polyterpenes consist of long chains of many isoprene units. Natural rubber consists of polyisoprene in which the double bonds are cis. Some plants produce a polyisoprene with trans double bonds, known as gutta-percha.

Norisoprenoids, such as the $C_{13}$-norisoprenoids 3-oxo-α-ionol present in Muscat of Alexandria leaves and 7,8-dihydroionone derivatives, such as megastigmane-3,9-diol and 3-oxo-7,8-dihydro-α-ionol found in Shiraz leaves (both grapes in the species *Vitis vinifera*) or wine (responsible for some of the spice notes in Chardonnay), can be produced by fungal peroxydase or glycosidases.

As used herein, the term "transfection" or "transformation" may refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into host cells. Examples of transfection techniques include, but are not limited to, calcium phosphate precipitation, DEAE-dextran-mediated transfection, lipofection, electroporation, and microinjection.

As used herein, the term "transformed," "stably transformed," and "transgenic" may refer to a cell that has a non-native (e.g., heterologous) nucleic acid sequence or polynucleotide sequence integrated into its genome or as an episomal plasmid that is maintained through multiple generations.

As used herein, the term “vector” may refer to a polynucleotide sequence designed to introduce nucleic acids into one or more cell types. Vectors include cloning vectors, expression vectors, shuttle vectors, plasmids, phage particles, single and double stranded cassettes and the like.

As used herein, the term “wild-type,” “native,” or “naturally-occurring” proteins may refer to those proteins found in nature. The terms wild-type sequence refers to an amino acid or nucleic acid sequence that is found in nature or naturally occurring. In some embodiments, a wild-type sequence is the starting point of a protein engineering project, for example, production of variant proteins.

Unless defined otherwise herein, all technical and scientific terms used herein have the same meaning as commonly understood by one of ordinary skill in the art to which this disclosure belongs. Singleton, et al., Dictionary of Microbiology and Molecular Biology, second ed., John Wiley and Sons, New York (1994), and Hale & Markham, The Harper Collins Dictionary of Biology, Harper Perennial, NY (1991) provide one of skill with a general dictionary of many of the terms used in this disclosure.

Numeric ranges provided herein are inclusive of the numbers defining the range.

Unless otherwise indicated, nucleic acids sequences are written left to right in 5' to 3' orientation; amino acid sequences are written left to right in amino to carboxy orientation, respectively.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word “about.” Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Modification of Microorganism

A microorganism can be modified (e.g., genetically engineered) by any method known in the art to comprise and/or express one or more polynucleotides coding for proteins in a system to optimize oligosaccharide utilization. Such proteins may include any of those proteins as are set forth in Tables 1-4. For example, the microorganism may be modified to comprise one or more polynucleotides coding for an energy independent oligosaccharide transporter for transporting oligosaccharides into the microorganism. Optionally, the microorganism may be further modified to comprise one or more polynucleotides coding for a phosphorylase and/or a phosphoglucomutase.

In an embodiment, a microorganism can be modified to comprise one or more polynucleotides coding for an energy independent oligosaccharide transporter for transporter oligosaccharides into the microorganism, one or more polynucleotides coding for a phosphorylase for catalyzing the conversion of the oligosaccharide into at least one phosphorylated saccharide, and one or more polynucleotides coding for a phosphoglucomutase for catalyzing the conversion of the phosphorylated saccharide into an isomer of the phosphorylated saccharide that is utilized in one or more enzymatic pathways in the microorganism. Optionally, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

Exemplary protein candidates for the disclosed optimized oligosaccharide utilization system and enzyme reaction products are presented in Table 1 below. Exemplary coding genes for some of the proteins are also presented in Table 1. The enzyme reference identifier listed in Table 1 correlates with the enzyme numbering used in FIG. 1, which schematically represents the transport of sucrose into a microorganism and the subsequent enzymatic conversion of sucrose into glucose-6-phosphate, which is then utilized in one or more enzymatic pathways in the microorganism.

TABLE 1

Examples of protein candidates for optimized oligosaccharide utilization.

| Ref. | Protein Family/Enzyme Name | E.C. number | Mediated Conversion | Examples | Citations |
|---|---|---|---|---|---|
| A | aquaporin | — | Potential sucrose uniport | *Arabidopsis thaliana* STP1 | Chaudhuri et al. 2008 |
| A | sucrose uptake facilitator (SUF) | — | sucrose uniport | *Pisum sativum* PsSUF1, PsSUF4 | Zhou et al. 2007 |

TABLE 1-continued

Examples of protein candidates for optimized oligosaccharide utilization.

| Ref. | Protein Family/Enzyme Name | E.C. number | Mediated Conversion | Examples | Citations |
|---|---|---|---|---|---|
| A | sucrose binding protein (SBP) | — | sucrose/maltose uniport | Soybean *Glycine max* (L) Merrill SBP1, SBP2 | Overvoorde et al. 1996, Pirovani et al. 2002 |
| A | sugars will eventually be exported transporter (SWEET) | — | sucrose uniport | *A. thaliana* AtSWEET10-15; *Oryza sativa* OzSWEET11 + 14; *Bradyrhizobium japonicum* SemiSWEET1 | Chen et al. 2010, Chen et al. 2012, Xuan et al. 2013 |
| B | sucrose phosphorylase | E.C. 2.4.1.7 | sucrose →α-D-glucose-1-phosphate + D-fructose | *Bifidobacterium adolescentis* Spl; *Leuconostoc mesenteroides* SucP | Goedl et al. 2007 |
| C | phosphoglucomutase | E.C. 5.4.2.2 | α-D-glucose-1-phosphate → α-D-glucose-6-phosphate | *S. cerevisiae* PGM1, PGM2 | Boles et al. 1994 |

In some embodiments, the disclosure contemplates the modification (e.g., engineering) of the uniporters provided herein. Such modification may be performed to enhance or alter one or more of the uniporter's properties, such as lowering the substance-transporter binding constant (Km), improving the expression of the protein, increasing the transport speed, or altering the substrate specificity of the protein.

The one or more proteins can be expressed in a microorganism selected from an archea, bacteria, or eukaryote. In some embodiments, the bacteria is a *Propionibacterium, Propionispira, Clostridium, Bacillus, Escherichia, Pelobacter*, or *Lactobacillus* including, for example, *Escherichia coli, Pelobacter propionicus, Clostridium propionicum, Clostridium acetobutylicum, Lactobacillus, Propionibacterium acidipropionici* or *Propionibacterium freudenreichii*. In some embodiments, the eukaryote is a yeast, filamentous fungi, protozoa, or algae. In some embodiments, the yeast is *Saccharomyces cerevisiae* or *Pichia pastoris*.

In some embodiments, sequence alignment and comparative modeling of proteins may be used to alter one or more of the proteins disclosed herein. Homology modeling or comparative modeling refers to building an atomic-resolution model of the desired protein from its primary amino acid sequence and an experimental three-dimensional structure of a similar protein. This model may allow for the protein substrate binding site to be defined, and the identification of specific amino acid positions that may be replaced to other natural amino acid in order to redesign its substrate specificity.

Variants or sequences having substantial identity or homology with the polynucleotides encoding proteins as disclosed herein may be utilized in the practice of the disclosure. Such sequences can be referred to as variants or modified sequences. That is, a polynucleotide sequence may be modified yet still retain the ability to encode a polypeptide exhibiting the desired activity. Such variants or modified sequences are thus equivalents. Generally, the variant or modified sequence may comprise at least about 30%-60%, preferably about 60%-80%, more preferably about 80%-90%, and even more preferably about 90%-95% sequence identity with the native sequence.

The microorganism may be modified by genetic engineering techniques (i.e., recombinant technology), classical microbiological techniques, or a combination of such techniques and can also include naturally occurring genetic variants to produce a genetically modified microorganism. Some of such techniques are generally disclosed, for example, in Sambrook et al., 1989, Molecular Cloning: A Laboratory Manual, Cold Spring Harbor Labs Press.

A genetically modified microorganism may include a microorganism in which a polynucleotide has been inserted, deleted or modified (i.e., mutated; e.g., by insertion, deletion, substitution, and/or inversion of nucleotides), in such a manner that such modifications provide the desired effect of expression (e.g., over-expression) of one or more proteins as provided herein within the microorganism. Genetic modifications which result in an increase in gene expression or function can be referred to as amplification, overproduction, overexpression, activation, enhancement, addition, or up-regulation of a gene. Addition of cloned genes to increase gene expression can include maintaining the cloned gene(s) on replicating plasmids or integrating the cloned gene(s) into the genome of the production organism. Furthermore, increasing the expression of desired cloned genes can include operatively linking the cloned gene(s) to native or heterologous transcriptional control elements.

Where desired, the expression of one or more of the proteins provided herein is under the control of a regulatory sequence that controls directly or indirectly the protein expression in a time-dependent fashion during the fermentation.

In some embodiments, a microorganism is transformed or transfected with a genetic vehicle, such as an expression vector comprising an exogenous polynucleotide sequence coding for the proteins provided herein.

Polynucleotide constructs prepared for introduction into a prokaryotic or eukaryotic host may typically, but not always, comprise a replication system (i.e. vector) recognized by the host, including the intended polynucleotide fragment encoding the desired polypeptide, and may preferably, but not necessarily, also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides may also be included where appropriate, preferably from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995).

The manipulation of polynucleotides that encode the proteins disclosed herein is typically carried out in recombinant vectors. Numerous vectors are publicly available, including bacterial plasmids, bacteriophage, artificial chromosomes, episomal vectors and gene expression vectors, which can all be employed. A vector may be selected to accommodate a polynucleotide encoding a protein of a desired size. Following recombinant modification of a selected vector, a suitable host cell is transfected or transformed with the vector. Host cells may be prokaryotic, such as any of a number of bacterial strains, or may be eukaryotic, such as yeast or other fungal cells, insect or amphibian cells, or mammalian cells including, for example, rodent, simian or human cells. Each vector contains various functional components, which generally include a cloning site, an origin of replication and at least one selectable marker gene. A vector may additionally possess one or more of the following elements: an enhancer, promoter, and transcription termination and/or other signal sequences. Such sequence elements may be optimized for the selected host species (e.g. humanized). Such sequence elements may be positioned in the vicinity of the cloning site, such that they are operatively linked to the gene encoding a preselected protein.

Vectors, including cloning and expression vectors, may contain nucleic acid sequences that enable the vector to replicate in one or more selected host cells. For example, the sequence may be one that enables the vector to replicate independently of the host chromosomal DNA and may include origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

A cloning or expression vector may contain a selection gene (also referred to as a selectable marker). This gene encodes a protein necessary for the survival or growth of transformed host cells in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in *E. coli* (e.g., strain TB1 or TG1, DH5α, DH10β, JM110). An *E. coli*-selectable marker, for example, the β-lactamase gene that confers resistance to the antibiotic ampicillin, may be of use. These selectable markers can be obtained from *E. coli* plasmids, such as pBR322 or a pUC plasmid such as pUC18 or pUC19, or pUC119.

Expression vectors may contain a promoter that is recognized by the host organism. The promoter may be operably linked to a coding sequence of interest. Such a promoter may be inducible or constitutive. Polynucleotides are operably linked when the polynucleotides are in a relationship permitting them to function in their intended manner.

Promoters suitable for use with prokaryotic hosts may include, for example, the α-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Moreover, host constitutive or inducible promoters may be used. Promoters for use in bacterial systems will also generally contain a Shine-Dalgarno sequence operably linked to the coding sequence.

Viral promoters obtained from the genomes of viruses include promoters from polyoma virus, fowlpox virus, adenovirus (e.g., Adenovirus 2 or 5), herpes simplex virus (thymidine kinase promoter), bovine papilloma virus, avian sarcoma virus, cytomegalovirus, retrovirus (e.g., MoMLV, or RSV LTR), Hepatitis-B virus, Myeloproliferative sarcoma virus promoter (MPSV), VISNA, and Simian Virus 40 (SV40). Heterologous mammalian promoters include, e.g., the actin promoter, immunoglobulin promoter, heat-shock protein promoters.

The early and late promoters of the SV40 virus are conveniently obtained as a restriction fragment that also contains the SV40 viral origin of replication (see, e.g., Fiers et al., Nature, 273:113 (1978); Mulligan and Berg, Science, 209:1422-1427 (1980); and Pavlakis et al., Proc. Natl. Acad. Sci. USA, 78:7398-7402 (1981)). The immediate early promoter of the human cytomegalovirus (CMV) is conveniently obtained as a Hind III E restriction fragment (see, e.g., Greenaway et al., Gene, 18:355-360 (1982)). A broad host range promoter, such as the SV40 early promoter or the Rous sarcoma virus LTR, is suitable for use in the present expression vectors.

Generally, a strong promoter may be employed to provide for high level transcription and expression of the desired product. Among the eukaryotic promoters that have been identified as strong promoters for high-level expression are the SV40 early promoter, adenovirus major late promoter, mouse metallothionein-I promoter, Rous sarcoma virus long terminal repeat, and human cytomegalovirus immediate early promoter (CMV or CMV IE). In an embodiment, the promoter is a SV40 or a CMV early promoter.

The promoters employed may be constitutive or regulatable, e.g., inducible. Exemplary inducible promoters include jun, fos and metallothionein and heat shock promoters. One or both promoters of the transcription units can be an inducible promoter. In an embodiment, the GFP is expressed from a constitutive promoter while an inducible promoter drives transcription of the gene coding for one or more proteins as disclosed herein and/or the amplifiable selectable marker.

The transcriptional regulatory region in higher eukaryotes may comprise an enhancer sequence. Many enhancer sequences from mammalian genes are known e.g., from globin, elastase, albumin, α-fetoprotein and insulin genes. A suitable enhancer is an enhancer from a eukaryotic cell virus. Examples include the SV40 enhancer on the late side of the replication origin (bp 100-270), the enhancer of the cytomegalovirus immediate early promoter (Boshart et al. Cell 41:521 (1985)), the polyoma enhancer on the late side of the replication origin, and adenovirus enhancers (see also, e.g., Yaniv, Nature, 297:17-18 (1982) on enhancing elements for activation of eukaryotic promoters). The enhancer sequences may be introduced into the vector at a position 5' or 3' to the gene of interest, but is preferably located at a site 5' to the promoter.

Yeast and mammalian expression vectors may contain prokaryotic sequences that facilitate the propagation of the vector in bacteria. Therefore, the vector may have other components such as an origin of replication (e.g., a nucleic acid sequence that enables the vector to replicate in one or more selected host cells), antibiotic resistance genes for selection in bacteria, and/or an amber stop codon which can permit translation to read through the codon. Additional eukaryotic selectable gene(s) may be incorporated. Generally, in cloning vectors the origin of replication is one that enables the vector to replicate independently of the host chromosomal DNA, and includes origins of replication or autonomously replicating sequences. Such sequences are well known, e.g., the ColE1 origin of replication in bacteria. Various viral origins (e.g., SV40, polyoma, adenovirus, VSV or BPV) are useful for cloning vectors in mammalian cells. Generally, a eukaryotic replicon is not needed for expression in mammalian cells unless extrachromosomal (episomal) replication is intended (e.g., the SV40 origin may typically be used only because it contains the early promoter).

To facilitate insertion and expression of different genes coding for the proteins as disclosed herein from the constructs and expression vectors, the constructs may be designed with at least one cloning site for insertion of any gene coding for any protein disclosed herein. The cloning site may be a multiple cloning site, e.g., containing multiple restriction sites.

The plasmids may be propagated in bacterial host cells to prepare DNA stocks for subcloning steps or for introduction into eukaryotic host cells. Transfection of eukaryotic host cells can be any performed by any method well known in the art. Transfection methods include lipofection, electroporation, calcium phosphate co-precipitation, rubidium chloride or polycation mediated transfection, protoplast fusion and microinjection. Preferably, the transfection is a stable transfection. The transfection method that provides optimal transfection frequency and expression of the construct in the particular host cell line and type is favored. Suitable methods can be determined by routine procedures. For stable transfectants, the constructs are integrated so as to be stably maintained within the host chromosome.

Vectors may be introduced to selected host cells by any of a number of suitable methods known to those skilled in the art. For example, vector constructs may be introduced to appropriate cells by any of a number of transformation methods for plasmid vectors. For example, standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods may be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to mammalian cells, the method used may depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, CLONTECH, Glen Research, InVitrogen, JBL Scientific, MBIFermentas, PanVera, Promega, Quantum Biotechnologies, Sigma-Aldrich, and Wako Chemicals USA.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation Immortalized host cell cultures amenable to transfection and in vitro cell culture and of the kind typically employed in genetic engineering are preferred. Examples of useful mammalian host cell lines are monkey kidney CV1 line transformed by SV40 (COS-7, ATCCCRL 1651); human embryonic kidney line (293 or 293 derivatives adapted for growth in suspension culture, Graham et al., J. Gen Virol., 36:59 (1977); baby hamster kidney cells (BHK, ATCC CCL 10); DHFR—Chinese hamster ovary cells (ATCC CRL-9096); dp12.CHO cells, a derivative of CHO/DHFR-(EP 307,247 published 15 Mar. 1989); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCCCRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); PEER human acute lymphoblastic cell line (Ravid et al. Int. J. Cancer 25:705-710 (1980)); MRC 5 cells; FS4 cells; human hepatoma cell line (Hep G2), human HT1080 cells, KB cells, JW-2 cells, Detroit 6 cells, NIH-3T3 cells, hybridoma and myeloma cells. Embryonic cells used for generating transgenic animals are also suitable (e.g., zygotes and embryonic stem cells).

Suitable host cells for cloning or expressing polynucleotides (e.g., DNA) in vectors may include, for example, prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), *E. coli* JM110 (ATCC 47,013) and *E. coli* W3110 (ATCC 27,325) are suitable.

In addition to prokaryotes, eukaryotic microbes such as filamentous fungi or yeast may be suitable cloning or expression hosts for vectors comprising polynucleotides coding for one or more enzymes. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; Yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

When the protein is glycosylated, suitable host cells for expression may be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk moth) have been identified. A variety of viral strains for transfection are publicly available, e.g., the L-1 variant of *Autographaca lifornica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, petunia, tomato, tobacco, lemna, and other plant cells can also be utilized as host cells.

Examples of useful mammalian host cells are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCCCRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCCCRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for production of one or more proteins as disclosed herein or with polynucleotides coding for one or more proteins as disclosed herein and cultured in conventional nutrient media modified as appropriate for inducing promoters, selecting transformants, or amplifying the genes encoding the desired sequences.

Host cells containing desired nucleic acid sequences coding for the disclosed enzymes may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44, (1979); Barnes et al., Anal. Biochem. 102: 255 (1980); U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Polynucleotides and Encoded Proteins

Any known polynucleotide (e.g., gene) that codes for a protein or variant thereof that can be used in a system for optimizing oligosaccharide utilization including, for example, a protein as set forth in Table 1 or FIG. 1, is contemplated for use by the present disclosure. Additional exemplary protein candidates for the disclosed optimized oligosaccharide utilization system and enzyme reaction products are presented in Tables 2-4 below. Such polynucleotides can be modified (e.g., genetically engineered) to modulate (e.g., increase or decrease) the substrate specificity of an encoded protein, or the polynucleotides may be modified to change the substrate specificity of the encoded protein (e.g., a polynucleotide that codes for a protein with specificity for a substrate may be modified such that the protein has specificity for an alternative substrate). For an energy independent saccharide transporter protein, such polynucleotides can be also be modified to lower the substance-transporter binding constant (Km), improve the expression of the protein, or increase the transport speed. Preferred microorganisms may comprise polynucleotides coding for one or more of the proteins as set forth in Tables 1-4 and FIG. 1.

TABLE 2

Exemplary uniporter proteins and candidate proteins to be evolved into uniporter proteins for optimized oligosaccharide utilization.

| SEQ ID NO: | Gene | GenBank or Uniport ID | Organism |
|---|---|---|---|
| 1 | PsSUF1 | A3DSX2 | *Pisum sativum* |
| 2 | PsSUF1 | DQ221698.2 | *Pisum sativum* |
| 3 | PsSUF4 | A3DSX1 | *Pisum sativum* |
| 4 | PsSUF4 | DQ221697.2 | *Pisum sativum* |
| 5 | PvSUF1 | A3DSX4 | *Phaseolus vulgaris* |
| 6 | PvSUF1 | DQ221700.1 | *Phaseolus vulgaris* |
| 7 | LjSUT4 | Q84RQ3 | *Lotus japonicus* |
| 8 | LjSUT4 | AJ538041.1 | *Lotus japonicus* |
| 9 | SIP1-1 | Q9M8W5 | *Arabidopsis thaliana* |
| 10 | SIP1-1 | AK226432.1 | *Arabidopsis thaliana* |
| 11 | SIP1-2 | Q9FK43 | *Arabidopsis thaliana* |
| 12 | SIP1-2 | BT005263.1 | *Arabidopsis thaliana* |
| 13 | SBP1 | Q04672 | *Glycine max* |
| 14 | SBP1 | L06038.1 | *Glycine max* |
| 15 | SBP2 | Q84V19 | *Glycine max* |
| 16 | SBP2 | AY234869.1 | *Glycine max* |
| 17 | AtSWEET10 | Q9LUE3 | *Arabidopsis thaliana* |
| 18 | AtSWEET10 | AY064674.1 | *Arabidopsis thaliana* |
| 19 | AtSWEET11 | Q9SMM5 | *Arabidopsis thaliana* |
| 20 | AtSWEET11 | AF361825.1 | *Arabidopsis thaliana* |
| 21 | AtSWEET12 | O82587 | *Arabidopsis thaliana* |
| 22 | AtSWEET12 | AY059108.1 | *Arabidopsis thaliana* |
| 23 | AtSWEET13 | Q9FGQ2 | *Arabidopsis thaliana* |
| 24 | AtSWEET13 | AY087516 | *Arabidopsis thaliana* |
| 25 | AtSWEET14 | Q9SW25 | *Arabidopsis thaliana* |
| 26 | AtSWEET14 | CP002687.1 | *Arabidopsis thaliana* |
| 27 | AtSWEET15 | Q9FY94 | *Arabidopsis thaliana* |
| 28 | AtSWEET15 | AY045949.1 | *Arabidopsis thaliana* |
| 29 | OzSWEET11 | Q6YZF3 | *Oryza sativa japonica* |
| 30 | OzSWEET11 | AK106127.1 | *Oryza sativa japonica* |
| 31 | OzSWEET14 | Q2R3P9 | *Oryza sativa japonica* |
| 32 | OzSWEET14 | AK101913.1 | *Oryza sativa japonica* |
| 33 | glpF | P0AER0 | *Escherichia coli* |
| 34 | glpF | X15054.1 | *Escherichia coli* |
| 35 | Suc | B0RRG6 | *Xanthomonas campestris* pv. *campestris* |
| 36 | Suc | Accession No.: NC_010688, 1961593 | *Xanthomonas campestris* pv. *campestris* |
| 37 | Cdt-1 | Q7SCU1 | *Neurospora crassa* |
| 38 | Cdt-1 | NCBI Ref. Seq. NW 001849825.1 | *Neurospora crassa* |
| 39 | Cdt-2 | Q75D12 | *Neurospora crassa* |
| 40 | Cdt-2 | NCBI Ref. Seq. NW 001849743.1 | *Neurospora crassa* |

TABLE 3

Exemplary phosphorylase proteins for optimized oligosaccharide utilization.

| SEQ ID NO | Gene | GenBank or Uniport ID | Organism |
|---|---|---|---|
| 41 | LVIS_0358 | Q03TE9 | *Lactobacillus brevis* |
| 42 | LVIS_0358 | NC_008497, 382638 | *Lactobacillus brevis* |
| 43 | mapA | O87772 | *Lactobacillus sanfranciscensis* |
| 44 | mapA | AJ224340.2 | *Lactobacillus sanfranciscensis* |
| 45 | Spl | A0ZZH6 | *Bifidobacterium adolescentis* |
| 46 | Spl | NC_008618, 104792 | *Bifidobacterium adolescentis* |
| 47 | SucP | Q59495 | *Leuconostoc mesenteroides* |
| 48 | SucP | D90314.1 | *Leuconostoc mesenteroides* |

TABLE 3-continued

Exemplary phosphorylase proteins for optimized oligosaccharide utilization.

| SEQ ID NO | Gene | GenBank or Uniport ID | Organism |
|---|---|---|---|
| 49 | Cbp | Q8VP44 | *Clostridium thermocellum* |
| 50 | Cbp | AY072794.1 | *Clostridium thermocellum* |

TABLE 4

Exemplary phosphoglucomutase proteins for optimized oligosaccharide utilization.

| SEQ ID NO: | Gene | GenBank or Uniprot ID | Organism |
|---|---|---|---|
| 51 | PGM1 | P33401 | *Saccharomyces cerevisiae* |
| 52 | PGM1 | X72016.1 | *Saccharomyces cerevisiae* |
| 53 | PGM2 | P37012 | *Saccharomyces cerevisiae* |
| 54 | PGM2 | X74823.1 | *Saccharomyces cerevisiae* |
| 55 | pgmA | O87773 | *Lactobacillus sanfranciscensis* |
| 56 | pgmA | AJ224340.2 | *Lactobacillus sanfranciscensis* |
| 57 | pgmB | P71447 | *Lactococcus lactis lactis* |
| 58 | pgmB | Z70730.1 | *Lactococcus lactis lactis* |

Methods of Optimizing Oligosaccharide Utilization

A microorganism's utilization of one or more oligosaccharides can be optimized by contacting any of the disclosed genetically modified microorganisms with an oligosaccharide source (e.g., a fermentable carbon source). Such methods can comprise contacting an oligosaccharide source with a microorganism comprising one or more polynucleotides coding for energy independent oligosaccharide transporter proteins (e.g. uniporters), such as those set forth in Table 1 and Table 2. Preferred nucleotide sequences for energy independent oligosaccharide transporter proteins and candidate proteins for evolution into energy independent oligosaccharide transporter proteins are provided by SEQ ID Nos.: 2, 4, 6, 8, 10, 12, 14, 16, 18, 20, 22, 24, 26, 28, 30, 32, 34, 36, 38 and 40. Preferred protein sequences for energy independent oligosaccharide transporter proteins or candidate proteins for evolution into energy independent oligosaccharide transporter proteins are provided by SEQ ID Nos.: 1, 3, 5, 7, 9, 11, 13, 15, 17, 19, 21, 23, 25, 27, 29, 31, 33, 35, 37 and 39. Such methods can also comprise contacting an oligosaccharide source with a microorganism comprising one or more polynucleotides coding for a uniporter, one or more polynucleotides coding for a phosphorylase, and one or more polynucleotides coding for a phosphoglucomutase. Preferred nucleotide sequences for phosphorylases are provided by SEQ ID Nos.: 42, 44, 46, 48 and 50. Preferred protein sequences for phosphorylases are provided by SEQ ID Nos.: 41, 43, 45, 47 and 49. Preferred nucleotide sequences for phosphoglucomutases are provided by SEQ ID Nos.: 52, 54, 56 and 58. Preferred protein sequences for phosphoglucomutases are provided by SEQ ID Nos.: 51, 53, 55 and 57.

Optionally, the methods may further comprise knocking-out (i.e., deleting) one or more naturally competing transporter systems (e.g., one or more nucleotides coding for one or more proteins involved in the transporter system) for transporting the oligosaccharide into the microorganism. Alternatively, the microorganism may naturally lack or may be obtained that lacks one or more competing transporter systems (e.g., one or more nucleotides coding for one or more proteins involved in the transporter system) for transporting the oligosaccharide into the microorganism. For example, for sucrose utilization in *S. cerevisiae* one or more of suc2, mal11, mal12, mal31, or mal32 may be knocked-out. Additionally, for example, for maltose utilization in *S. cerevisiae* one or more of suc2, mal11, mal12, mal31, mal32, mph2, or mph3 may be knocked-out. Further, for example, for maltose utilization in *E. coli* at least one genes of the group malE, malF, malK, malG, or lamb may be knocked-out. In other embodiments, for example, for cellobiose utilization in *S. cerevisiae*, for sucrose utilization in *E. coli*, or for cellobiose utilization in *E. coli*, :the microorganism does not have any naturally competing transporter systems knocked-out.

The compound or molecule resulting from the optimized oligosaccharide utilization method is then utilized in one or more enzymatic pathways in the microorganism that have been engineered to produce industrially important compounds.

The metabolic pathways that lead to the production of industrially important compounds involve oxidation-reduction (redox) reactions. For example, during fermentation, glucose is oxidized in a series of enzymatic reactions into smaller molecules with the concomitant release of energy. The electrons released are transferred from one reaction to another through universal electron carriers, such Nicotinamide Adenine Dinucleotide (NAD) and Nicotinamide Adenine Dinucleotide Phosphate (NAD(P)), which act as cofactors for oxidoreductase enzymes. In microbial catabolism, glucose is oxidized by enzymes using the oxidized form of the cofactors (NAD(P)+ and/or NAD+) as cofactor thus generating reducing equivalents in the form of the reduced cofactor (NAD(P)H and NADH). In order for fermentation to continue, redox-balanced metabolism is required, i.e., the cofactors must be regenerated by the reduction of microbial cell metabolic compounds.

Microorganism-catalyzed fermentation for the production of natural products is a widely known application of biocatalysis. Industrial microorganisms can affect multistep conversions of renewable feedstocks to high value chemical products in a single reactor. Products of microorganism-catalyzed fermentation processes range from chemicals such as ethanol, lactic acid, amino acids and vitamins, to high value small molecule pharmaceuticals, protein pharmaceuticals, and industrial enzymes. In many of these processes, the biocatalysts are whole-cell microorganisms, including microorganisms that have been genetically modified to express heterologous genes.

Some key parameters for efficient microorganism-catalyzed fermentation processes include the ability to grow microorganisms to a greater cell density, increased yield of desired products, increased amount of volumetric productivity, removal of unwanted co-metabolites, improved utilization of inexpensive carbon and nitrogen sources, adaptation to varying fermenter conditions, increased production of a primary metabolite, increased production of a secondary metabolite, increased tolerance to acidic conditions, increased tolerance to basic conditions, increased tolerance to organic solvents, increased tolerance to high salt conditions and increased tolerance to high or low temperatures. Inefficiencies in any of these parameters can result in high manufacturing costs, inability to capture or maintain market share, and/or failure to bring fermented end-products to market.

The methods and compositions of the present disclosure can be adapted to conventional fermentation bioreactors (e.g., batch, fed-batch, cell recycle, and continuous fermentation).

In some embodiments, a microorganism (e.g., a genetically modified microorganism) as provided herein is cultivated in liquid fermentation media (i.e., a submerged culture) which leads to excretion of the fermented product(s) into the fermentation media. In one embodiment, the fermented end product(s) can be isolated from the fermentation media using any suitable method known in the art.

In some embodiments, formation of the fermented product occurs during an initial, fast growth period of the microorganism. In one embodiment, formation of the fermented product occurs during a second period in which the culture is maintained in a slow-growing or quiescent state. In one embodiment, formation of the fermented product occurs during more than one growth period of the microorganism. In such embodiments, the amount of fermented product formed per unit of time is generally a function of the metabolic activity of the microorganism, the physiological culture conditions (e.g., pH, temperature, medium composition), and the amount of microorganisms present in the fermentation process.

In some embodiments, the fermentation product is recovered from the periplasm or culture medium as a secreted metabolite. In one embodiment, the fermentation product is extracted from the microorganism, for example when the microorganism lacks a secretory signal corresponding to the fermentation product. In one embodiment, the microorganisms are ruptured and the culture medium or lysate is centrifuged to remove particulate cell debris. The membrane and soluble protein fractions may then be separated if necessary. The fermentation product of interest may then be purified from the remaining supernatant solution or suspension by, for example, distillation, fractionation, chromatography, precipitation, filtration, and the like. In one embodiment, the microorganism cells (or portions thereof) may be used as biocatalysts or for other functions in a subsequent process without substantial purification.

Methods of Modifying Transporter Proteins

An energy independent transporter (e.g., uniporter) for a given saccharide can be selected or identified from a set of unspecified transporters, evolved (e.g. modified) from a known energy dependent transporter, or improved from an existing uniporter wildtype. All three of these can be accomplished by selecting the desired uniport activity through growth selection.

Libraries of mutated candidate genes can be used to select candidate genes. The selected candidate genes are then expressed in a microorganism, such as yeast, that is deficient in the uptake or transport of the oligosaccharide of interest, but otherwise capable of metabolizing saccharides. In an embodiment, the *S. cerevisiae* INV8 or SUSY7 strain for sucrose transport is used to express candidate genes. (Riesmeier et al. 1992.)

The microorganism strains expressing the candidate genes are then grown on or in minimal media with the saccharide of interest as the only carbon source. For example, the strains expressing candidate genes can be grown in a chemostat or turbidostat. Growth of a strain on this minimal media indicates that the candidate gene encodes a saccharide transporter. The strains expressing candidate genes for the most efficient saccharide transporters will have the highest growth rate. A strain that has a candidate gene encoding an improved saccharide transporter will outcompete other clones in the same culture and, eventually, will dominate the culture.

This approach is also known as evolutionary fermentation. Through the above-described process, saccharide transporters can be identified from non-transporters. Additionally, this process can be used to continuously improve a known uniporter, such as by lowering the substance-transporter binding constant (Km), improving the expression of the protein, increasing the transport speed, or altering the substrate specificity of the protein, for a substrate of choice and in a strain of choice. For example, the well known *S. cerevisiae* hexose uniporters of the Hxt family could be mutated and selected from sucrose acceptance. In another example, the sucrose uniporters mentioned in this application can be optimized for maltose or cellobiose acceptance, particularly since SBP1 already demonstrates maltose transport activity. In yet another example, the *E. coli* glycerol uniporter can be evolved to accept maltose, sucrose or cellobiose.

The above-described process can also be used to evolve an energy dependent transporter into an energy independent transporter. Instead of assessing the growth rate of the cultured strains, the biomass formation of the strains should be measured. Strains that express an energy independent transporter would have more ATP and, therefore, higher biomass formation (e.g., an increase in biomass formation of, for example, 25% or 33%) from growth on limited media than strains expressing an energy dependent transporter. In an embodiment, the strains expressing candidate genes are cultured individually, such as in 96 well plates, to avoid competition by growth speed instead of total biomass formation. The biomass of each strain is then measured using simple, high throughput optical density methods, such as by using an OD600 plate reader. For example, the bacterial maltose/sucrose H+ symporter Suc from *Xanthomonas campestris* can be evolved to function as an uniporter.

Symporters could potentially be evolved into uniporters using the above-described process. This is based, in part, on the fact that some SUF sucrose uniporters are closely related to sucrose H+ (SUT) symporters in clade I (PvSUT3 and PvSUF1) and clade II (LjSUT4 and PsSUF4) of the sucrose transporter family (Zhou et al. 2007). The close relationship of SUF uniporters and SUT symporters suggests that symporters could be successfully evolved into uniporters.

Additionally, transporters utilizing energy in the form of ATP or GTP could potentially be evolved into energy independent uniporters. This is based on the fact that sucrose binding protein 2 (SBP2) binds GTP, but mutant versions of SBP2 unable to bind GTP still function as sucrose transporters in yeast (Pirovani et al. 2002). While SBP2 can bind GTP and presumably use its energy, it obviously does not need GTP to function as importer. Thus, it seems possible that an energy independent uniporter could be evolved from some transporters that usually utilize PEP, ATP, or GTP.

EXAMPLES

Example 1

Modification of Microorganism to Optimize Oligosaccharide Utilization

A microorganism such as yeast or bacteria is genetically modified to optimize its utilization of oligosaccharides.

In an exemplary method, a microorganism, such as the bacterium *E. coli*, is genetically engineered by any methods known in the art to comprise a maltose uniporter, a maltose phosphorylase, and a β-phosphoglucomutase for the transport, phosphorolysis and inversion of maltose, for instance by expressing a glycerol uniporter GlpF mutant from *E. coli* evolved to accept sucrose or a maltose/sucrose H+ symporter Suc mutant from *Xanthomonas campestris* evolved to function as uniporter, LVIS_0358 from *Lactobacillus brevis* and PgmB from *Lactococcus lactis.*

In another exemplary method, a microorganism, such as the yeast *S. cerevisiae*, is genetically engineered by any methods known in the art to comprise a maltose uniporter, a maltose phosphorylase, and a β-phosphoglucomutase for the transport, phosphorolysis and inversion of maltose, for instance by expressing SBP1 from *Glycine max*, LVIS_0358 from *Lactobacillus brevis* and PgmB from *Lactococcus lactis.*

In an exemplary method, a microorganism, such as the bacterium *E. coli*, is genetically engineered by any methods known in the art to comprise a cellobiose uniporter, a cellobiose phosphorylase, and an α-phosphoglucomutase for the transport, phosphorolysis and inversion of cellobiose, for instance by expressing a glycerol uniporter GlpF mutant from *E. coli* evolved to accept cellobiose, Cbp from *Clostridium thermocellum* and PGM1 from *S. cerevisiae.*

In another exemplary method, a microorganism, such as the yeast *S. cerevisiae*, is genetically engineered by any methods known in the art to comprise a cellobiose uniporter, a cellobiose phosphorylase, and an α-phosphoglucomutase for the transport, phosphorolysis and inversion of cellobiose, for instance by expressing CDT2 from *Neurospora crassa*, Cbp from *Clostridium thermocellum* and PGM1 from *S. cerevisiae.*

In another exemplary method, a microorganism, such as the bacterium *E. coli*, is genetically engineered by any methods known in the art to comprise a sucrose uniporter, a sucrose phosphorylase, and an α-phosphoglucomutase for the transport, phosphorolysis and inversion of sucrose, for instance by expressing a glycerol uniporter GlpF mutant from *E. coli* evolved to accept sucrose or a maltose/sucrose H+ symporter Suc mutant from *Xanthomonas campestris* evolved to function as uniporter, SucP from *Leuconostoc mesenteroides* and PGM1 from *S. cerevisiae.*

In another exemplary method, a microorganism, such as the yeast *S. cerevisiae*, is genetically engineered by any methods known in the art to comprise a sucrose uniporter, a sucrose phosphorylase, and an α-phosphoglucomutase for the transport, phosphorolysis and inversion of sucrose, for instance by expressing SUF1 from *Pisum sativum*, SucP from *Leuconostoc mesenteroides* and PGM1 from *S. cerevisiae.*

The sucrose uniporter passively imports the sucrose to the microorganism without using any energy. The phosphorylase utilizes the energy content of the glycoside bond to yield a phosphorylated glucose and a non-phosphorylated fructose. The α-phosphoglucomutase then converts the phosphorylated glucose to an isomer that is utilized by the microorganism. The phosphorylated glucose is then degraded into pyruvate and ATP by glycolysis. The steps involved and the resulting ATP production from the use of the optimized oligosaccharide utilization system are set forth below:

Import: sucrose→(uniporter)→sucrose

Phosphorylation: sucrose+phosphate→(phosphorylase)→glucose-1-phosphate+fructose

Conversion: glucose-1-phosphate+fructose→(phosphoglucomutase)→glucose-6-phosphate+fructose Glycolysis Summary: sucrose+5ADP+5phosphate→4 pyruvate+5ATP A naturally occurring oligosaccharide utilization system does not produce as much ATP as the optimized oligosaccharide utilization system described above. For example, *S. cerevisiae* naturally uses an excreted invertase (EC 3.2.1.26) to hydrolyze sucrose to glucose and fructose. This results in the loss of the energy present in the glycolytic bond. The glucose and fructose are then passively imported into the yeast and phosphorylated to glucose-6-phosphate and fructose-6-phosphate, using one ATP for each hexose (Barnett 1976, Lagunas 1993). The steps involved in this process and the resulting ATP production are set forth below:

Hydrolysis: sucrose→(invertase)→glucose+fructose

Import: glucose+fructose→glucose+fructose

Phosphorylation: glucose+ATP→glucose-6-phosphate+ADP→fructose-6-phosphate+ADP fructose+ATP→fructose-6-phosphate+ADP Glycolysis: 2 fructose-6-phosphate+6 ADP+6 phosphate→4 pyruvate+6 ATP Summary: sucrose+4ADP+4 phosphate→4 pyruvate+4 ATP Likewise, other sucrose utilization systems, including heterologous systems for microbial use, also do not produce as much ATP as the optimized oligosaccharide utilization system. Heterologous systems for microbial use mainly utilize sucrose/proton ($H^+$) symporters where sucrose is imported in an energy dependent manner. This manner of importing sucrose is energy dependent because the imported proton must then be exported by an ATPase, which requires the use of one ATP per proton (Serrano 1984). In the majority of systems, once imported the sucrose is then hydrolyzed to glucose and fructose, which, as mentioned above, causes the loss of the energy present in the glycolytic bond. The steps involved in this process and the resulting ATP production are set forth below:

Import: sucrose+$H^+$→(symporter)→sucrose+$H^+$

Export: $H^+$+ATP→$H^+$+ADP+P

Hydrolysis: sucrose→(hydrolase)→glucose+fructose

Glycolysis

Summary: sucrose+3 ADP+3 phosphate→4 pyruvate+3 ATP

The examples above show differences in ATP yield from 3 to 5 ATP per sucrose. Use of the disclosed optimized oligosaccharide utilization system on larger saccharides will lead to a higher ATP gain per released hexose. Large saccharides up to tetra-saccharides can be imported by the disclosed transporters, although at low efficiency. Table 5 below shows the effect of the optimized oligosaccharide utilization system on ATP yield per hexose. The values provided are shown for degradation of the saccharide to pyruvate, which is a common intermediate for aerobic and anaerobic conditions. During anaerobic fermentation, pyruvate would be further reduced to ethanol to re-oxidize the NADH produced during glycolysis.

TABLE 5

Effect of optimized oligosaccharide utilization on ATP yield per hexose.

| | ATP per hexose (degradation to pyruvate using glycolysis) | | | |
|---|---|---|---|---|
| saccharide | active transport, hydrolysis | hydrolysis, passive transport | active transport, phosphorolysis | passive transport, phosphorolysis (the optimized oligosaccharide utilization system) |
| mono- | 1 | 2 | 1 | 2 |
| di- | 1.5 | 2 | 2 | 2.5 |
| tri- | 1.67 | 2 | 2.33 | 2.67 |
| tetra- | 1.75 | 2 | 2.5 | 2.75 |

As shown in Table 5, above, the impact of the optimized oligosaccharide utilization system is particularly high under anaerobic conditions, where di-saccharide fermentation to ethanol usually yields 2 ATP per hexose. The use of the disclosed optimized oligosaccharide utilization system increases the ATP yield to 2.5 ATP per hexose for di-saccharides, an increase of 25%. A 25% increase in ATP production can translate into 25% more of the resulting product. In industrial applications, where the microorganism has also been genetically modified to produce a desired chemical, this can mean a significant increase in chemical production.

The use of higher order oligosaccharides can result in a greater increase in the ATP yield per hexose. The use of higher order oligosaccharides, such as tri-saccharides, even with the use of phosphorolysis with active transport, can significantly increase the ATP yield per hexose. However, the uptake or import of these higher order oligosaccharides is very inefficient (Zhou et al. 2007) and they are not commonly used as feedstocks.

Example 2

Impact of Optimization of Sucrose Utilization in a Microorganism Anaerobically Producing the Organic Molecules Isoprene and Ethanol As an example, the potential impact of optimized oligosaccharide utilization on the anaerobic production of isoprene in *S. cerevisiae* is calculated. In U.S. Provisional Patent Application No. 62/003,919, anaerobic isoprene production via mevalonate pathway is claimed, utilizing partial non-oxydative glycolysis via PK/PTA pathway to achieve redox neutrality and therefore retaining maximum carbon in the product. Optimized for maximum isoprene production, the theoretic maximum yields are 17.45 wt % isoprene and 23.60 wt % ethanol, which is a necessary co-product to deliver ATP (+2 ATP per molecule of ethanol produced), as calculated by a metabolic model. This maximum yield is calculated for redox and ATP neutral conditions (0 NADH, 0 ATP). This scenario applies to fermentations based on glucose as well as sucrose, where a *S. cerevisiae* strain naturally utilizes secreted sucrose invertase and passive hexose uptake.

Using a strain with implemented optimized oligo-saccharide utilization for sucrose, assuming 100% efficiency, the maximum theoretical yield would be 21.81 wt % isoprene and 16.72 wt % ethanol on sucrose. The increase from 17.45 wt % to 21.81 wt % equals +25%. This +25% increase stems from the fact that the optimized system delivers +25% ATP per hexose, thus 25% less saccharide is needed to form ethanol and can be used for synthesis of the main product isoprene instead. This increase will have a dramatic effect on the economic viability of the anaerobic fermentative production of this bulk chemical in a highly competitive market with low margins, where feedstock costs are usually by far the main factor in production costs (~50% of total costs). It also shows the advantage of using a method that combines an engineered strain with implemented optimized oligosaccharide utilization and the feedstock sugar cane juice, in contrast to using natural sucrose utilization or in contrast to using glucose as feedstock.

Example 3

Establishing *S. cerevisiae* S288c with an Optimized Sucrose Uptake System

In order to test and demonstrate functionality of the individual components and the entire optimized oligo-saccharide optimization system for sucrose in *S. cerevisiae* intrinsic, competing utilization pathways, like energy dependent transport, in the utilized strain were knocked-out (i.e., deleted). These deletions also ensure that the full benefit of the optimized oligo-sacharose utilization system can obtained and that no energy is lost. In addition to the secreted sucrose invertase SUC2 (GeneID 854644), parts of the maltose utilization system, the maltose transporters MAL11 (Gene ID 853207) and MAL31 (Gene ID 852601) and maltases MAL12 (Gene ID: 853209) and MAL32 (Gene ID: 852602), are known to be involved in the transport of sucrose (Mwesigye et al. 1994, Stambuk et al. 1999). Thus, these five genes may be deleted to obtain a strain without a natural sucrose utilization system, regarding transport as well as hydrolysis. Briefly, the KanMX4 marker gene was amplified from the plasmid pUG6 (GenBank: AM701829.1) with primers BKO1008 (SEQ ID NO: 76) and BKO1009 (SEQ ID NO: 77). These primers contain 40 bp sequence identity to the regions upstream and downstream of the MAL11-MAL12 genes, which are located at adjacent loci in the S288c genome.

Figure 2:
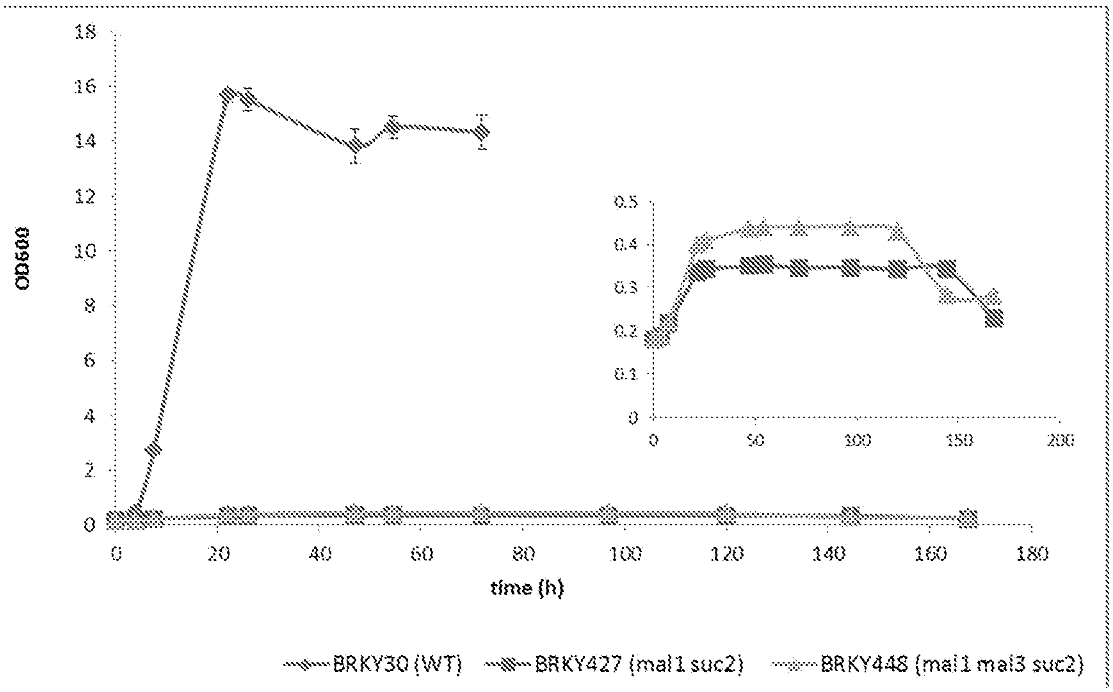
FIG. 2. Growth profile of strains BRKY30, BRKY427 and BRKY448 with sucrose as sole carbon source.

The resulting linear DNA cassette BKO1008-BKO1009 (SEQ ID NO. 68) was transformed into wild-type S288c (ATCC 204508, with auxotrophies his3 leu2 ura3 and trp1), creating the deletion mutant S288c (mal11 mal12). G418 (Gentamycin) resistant candidates, demonstrating successful replacement of the targeted MAL11-MAL12 gene region with the KanMX4 marker gene, were confirmed by colony PCR and sequencing. Likewise, the SUC2 gene was deleted: The HIS3 marker gene (GeneID 854377) was amplified from chromosomal DNA isolated from *S. cerevisiae* S288c strain (ATCC 204508) using the primers BKO1016 (SEQ ID NO: 78) and BKO1017 (SEQ ID NO: 79) with 40 bp sequence identity to the regions upstream and downstream of the SUC2 gene. The resulting PCR product BKO1016-BKO1017 (SEQ ID NO. 69) was transformed into S288c (mal11 mal12) to generate BRKY427 (mal11 mal12 suc2), selected through complementation of the histidine auxotrophy, and verified by colony-PCR and sequencing. MAL31 and MAL32, also co-located in the genome, were deleted through markerless deletion from position 802631 to 807105 on chromosome 2, and verified by colony-PCR and sequencing. The constructed strain should be unable to utilize sucrose. In order to confirm the suc$^-$ phenotype of the constructed strain, growth tests were conducted in shake flasks in triplicate with strains BRKY30 (S288c wildtype), BRKY427 (mal11 mal12 suc2) and BRKY448 (mal11 mal12 mal31 mal32 suc2) (FIG. 2). The strains were pre-grown in YNB media with 2% glucose overnight, washed and inoculated in YNB with 2% sucrose as sole carbon source to an OD of 0.2. To complement the remaining auxotrophies of the parent strain, all cultures required addition of leucine, tryptophan and uracil in a minimal media. The flasks were incubated at 30° C. and 250 rpm.

Figure 3:
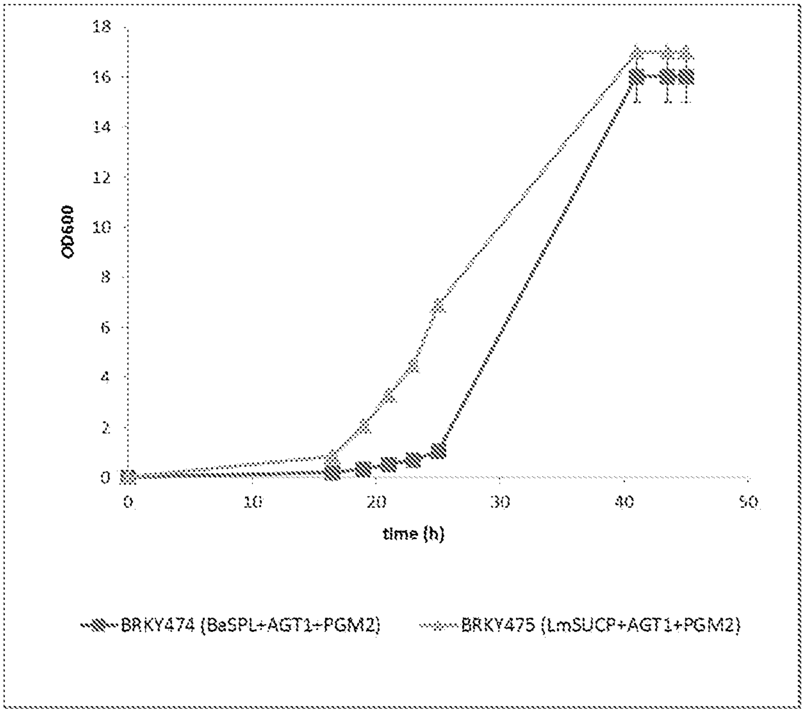
FIG. 3. Growth profile of strains BRKY474 and BRKY475 with sucrose as sole carbon source.

As expected, the wildtype (WT) strain consumed all the sucrose within 20 hours. Both BRKY427 and BRKY448 were unable to grow with sucrose as sole carbon source even after 160 hours of cultivation, proving that the suc$^-$ mal$^-$ phenotype was established and is stable over a long period of time under the assayed conditions. Two sucrose phosphorylase candidates, SucP from *Leuconostoc mesenteroides* (LmSUCP) and SPL from *Bifidobacterium adolescent* (BaSPL), were tested in BRKY448 overexpressing its natural, energy dependent sucrose/maltose H+ symporter AGT1 (MAL11) (see FIG. 3). The genes were cloned as transcription units with the promotor and terminator as described in table 6 by standard means and methods known to a person skilled in the art into and expressed episomally from the plasmid pRS415 (GenBank: U03449.1) (SEQ ID NO. 70). Expression and growth tests were performed as described above. Both strains showed strong growth, albeit slower than the wildtype. A phosphoglucomutase gene was not overexpressed in this test, suggesting that there is sufficient induction and activity of the intrinsic PGM2. As LmSUCP demonstrated faster growth complementation, it was selected to establish the full optimized sucrose utilization system.

Plant based uniporter candidate genes were cloned, as a transcription unit with a strong promotor and terminator (SEQ IDs 71-75), on the plasmid pRS415 and combined with the transcription units pTDH3-LmSUCP-tTDH3 and pTDH3-PGM2-tADH1, to establish the complete optimized sucrose utilization system (see, Table 6). The given promotor sequences were cloned by standard methods directly upstream of the gene start codon and terminator sequences directly downstream of the stop codon of the given gene. Growth complementation tests of BRKY448 harboring those plasmids were performed as described previously, using glass tubes with liquid media. Each experiment was stopped with an end-point OD-measurement after 8 days, or earlier if significant growth occurred before (Table 6). For strains not showing growth at 2% sucrose, the experiment was repeated with 4% sucrose, and AtSWEET14 as positive control. Transcription units for LmSUCP and PGM2 were episomally expressed in BRKY448 without a transporter gene as a negative control, the S288C wildtype without further genetic modifications served as positive control. While growing slower than the wildtype, 9 out of 13 tested uniporter candidates showed growth complementation in YNB with 2% or 4% succrose. Thus, for all uniporter candidate families tested, at least one member each was able to complement growth of BRKY448 if co-expressed with a functional sucrose phosphorylase and phosphoglucomutase (Table 6). None of the uniporter candidates could complement growth of BRKY448 with sucrose as sole carbon source if expressed without a functional phosphorylase (data not shown).

TABLE 6

Aerobic growth complementation of BRKY448 from sucrose uniporter candidate genes, cloned together with pTDH3-LmSPase-tTDH3 and pTDH3-PGM2-tADH1.

| Tested transcription unit (promoter/ gene/terminator) | Function/Protein Family | Growth with 2% sucrose (days)* | Growth with 4% sucrose (days)* |
|---|---|---|---|
| pTDH3-PsSUF1-tTDH3 | sucrose uptake facilitator (SUF) | — | 5.9 (5 d) |
| pTDH3-PsSUF4-tTDH3 | sucrose uptake facilitator (SUF) | — | — |
| pTDH3-PvSUF1-tTDH3 | sucrose uptake facilitator (SUF) | — | 5.0 (6 d) |
| pTDH3-GmSBP1-tTDH3 | sucrose binding protein (SBP) | 5.8 (8 d) | ND |
| pTDH3-GmSBP2-tTDH3 | sucrose binding protein (SBP) | — | 5.1 (3 d) |
| pTDH3-AtSWEET10-tTDH3 | SWEET transporter | 4.0 (7 d) | ND |
| pTDH3-AtSWEET11-tTDH3 | SWEET transporter | 4.2 (7 d) | ND |
| pTDH3-AtSWEET12-tTDH3 | SWEET transporter | — | — |
| pTDH3-AtSWEET13-tTDH3 | SWEET transporter | — | ND |
| pTDH3-AtSWEET14-tTDH3 | SWEET transporter | 3.4 (8 d) | 5.1 (6 d) |
| pTDH3-AtSWEET15-tTDH3 | SWEET transporter | 3.2 (8 d) | ND |
| pTDH3-OzSWEET11-tTDH3 | SWEET transporter | — | — |
| pTDH3-OzSWEET12-tTDH3 | SWEET transporter | — | 6.1 (3 d) |
| No transporter | Negative control | — | — |
| Wildtype | Positive control | 6.0 (2 d) | ND |

*ND: not determined/assayed. "—": no detectable growth observed within 8 days.

Figure 4:
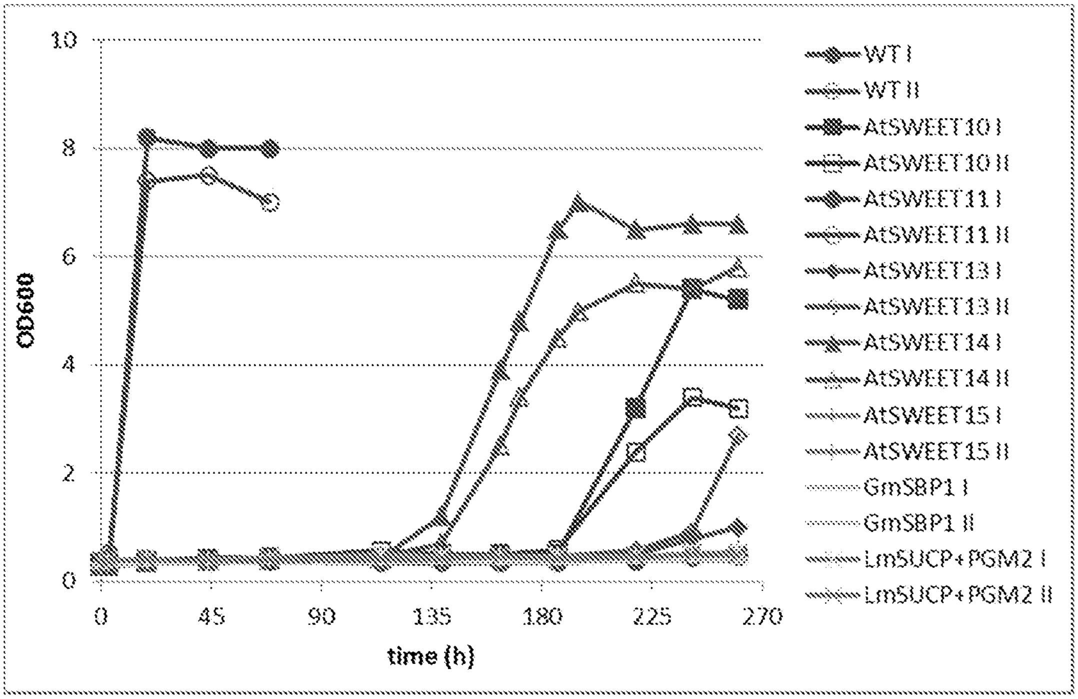
FIG. 4. Growth kinetics for six uniporter candidates in anaerobic flasks (2% sucrose).

For a further characterization, some uniporter candidates were tested in an anaerobic growth complementation assay, in duplicate (FIG. 4). The conditions were as described previously (2% sucrose), but utilizing an anaerobic, closed flask system with separately operable gas and sample lines for the main culture. The main-culture was sparged with nitrogen before and for 2 h after inoculation, closed and shaken at 30° C./250 rpm. The wildtype strain was capable of reaching the stationary phase after around 20 hours. Several BRKY448 strains were modified for an optimized uptake system which showed growth complementation after a lag phase of more than 100 h (FIG. 4), in contrast to the negative control lacking a transporter.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

What is claimed is:

1. A method of optimizing utilization of an oligosaccharide in a *Saccharomyces* microorganism comprising:

a) providing an oligosaccharide source, wherein the oligosaccharide is sucrose;

b) expressing one or more polynucleotides in the *Saccharomyces* microorganism that encode an energy-independent oligosaccharide transporter for transporting the oligosaccharide into the *Saccharomyces* microorganism, wherein the oligosaccharide transporter is selected from 'sugars will eventually be exported transporter' (SWEET) proteins, wherein the SWEET protein is SWEET14 from *Arabidopsis thaliana;* c) disrupting or deleting all energy-dependent transporters which transport the oligosaccharide into the *Saccharomyces* microorganism;

d) expressing one or more polynucleotides in the *Saccharomyces* microorganism that encode a phosphorylase for catalyzing a conversion of the oligosaccharide into at least one phosphorylated saccharide;

e) expressing one or more polynucleotides in the *Saccharomyces* microorganism that encode a phosphoglucomutase for catalyzing a conversion of the phosphorylated saccharide into an isomer of the phosphorylated saccharide, wherein the isomer of the phosphorylated saccharide is utilized in one or more enzymatic pathways in the *Saccharomyces* microorganism; and f) contacting the oligosaccharide source with the *Saccharomyces* microorganism.

2. The method of claim 1, wherein the polynucleotides encoding the phosphorylase are genes selected from the group consisting of: spl of *Bifidobacterium adolescentis*, sucP of *Leuconostoc mesenteroides*, LVIS_0358 of *Lactobacillus brevis*, mapA of *Lactobacillus sanfranciscensis*, and cbp from *Clostridium thermocellum.*

3. The method of claim 1, wherein the phosphoglucomutase is selected from the group consisting of: α-phosphoglucomutase and β-phosphoglucomutase.

4. The method of claim 1, wherein the phosphoglucomutase is selected from the group consisting of: pgm1 and pgm2 from *Saccharomyces cerevisiae*, pgmA from *Lactobacillus sanfranciscensis*, and pgmB from *Lactococcus lactis*.

5. The method of claim 1, wherein the oligosaccharide source is contacted with the *Saccharomyces* microorganism prior to expressing one or more polynucleotides in the *Saccharomyces* microorganism that encode an energy-independent oligosaccharide transporter for transporting the oligosaccharide into the *Saccharomyces* microorganism; expressing one or more polynucleotides in the *Saccharomyces* microorganism that encode a phosphorylase for catalyzing a conversion of the oligosaccharide into at least one phosphorylated saccharide; and expressing one or more polynucleotides in the *Saccharomyces* microorganism that encode a phosphoglucomutase for catalyzing a conversion of the phosphorylated saccharide into an isomer of the phosphorylated saccharide, wherein the isomer of the phosphorylated saccharide is utilized in one or more enzymatic pathways in the *Saccharomyces* microorganism.

6. The method of claim 1, wherein the isomer of the phosphorylated saccharide is utilized in a pathway for the production of an organic molecule.

7. The method of claim 1, wherein the microorganism is *S. cerevisiae* and one or more of suc2, mal 11, mal12, mal31, or mal32 may be knocked out, or one or more of suc2, mal11, mal12, mal31, mal32, mph2, or mph3 may be knocked out.

8. A method of optimizing utilization of an oligosaccharide in a *Saccharomyces* microorganism to produce an organic molecule comprising:

a) providing an oligosaccharide source, wherein the oligosaccharide is sucrose;

b) expressing one or more polynucleotides in the *Saccharomyces* microorganism that encode an energy-independent oligosaccharide transporter for transporting the oligosaccharide into the *Saccharomyces* microorganism, wherein the oligosaccharide transporter is selected from 'sugars will eventually be exported transporter' (SWEET) proteins, wherein the SWEET protein is SWEET14 from *Arabidopsis thaliana;* c) disrupting or deleting all energy-dependent transporters which transport the oligosaccharide into the *Saccharomyces* microorganism;

d) expressing one or more polynucleotides in the *Saccharomyces* microorganism that encode a phosphorylase for catalyzing a conversion of the oligosaccharide into at least one phosphorylated saccharide;

e) expressing one or more polynucleotides in the *Saccharomyces* microorganism that encode a phosphoglucomutase for catalyzing a conversion of the phosphorylated saccharide into an isomer of the phosphorylated saccharide;

f) expressing one or more polynucleotides in the *Saccharomyces* microorganism for catalyzing a conversion of the isomer into an organic molecule, wherein the organic molecule is isopropanol; and g) contacting the oligosaccharide source with the *Saccharomyces* microorganism.

9. A method of increasing the yield of an organic molecule produced by a *Saccharomyces* microorganism under anaerobic conditions, the method comprising:

a) providing an oligosaccharide source for use by the *Saccharomyces* microorganism, wherein the oligosaccharide is sucrose;

b) expressing one or more polynucleotides in the *Saccharomyces* microorganism that encode an energy-independent oligosaccharide transporter for transporting the oligosaccharide into the *Saccharomyces* microorganism, wherein the oligosaccharide transporter is selected from 'sugars will eventually be exported transporter' (SWEET) proteins, wherein the SWEET protein is SWEET14 from *Arabidopsis thaliana;* c) disrupting or deleting all energy-dependent transporters which transport the oligosaccharide into the *Saccharomyces* microorganism;

d) expressing one or more polynucleotides in the *Saccharomyces* microorganism that encode a phosphorylase for catalyzing a conversion of the oligosaccharide into at least one phosphorylated saccharide;

e) expressing one or more polynucleotides in the *Saccharomyces* microorganism that encode a phosphoglucomutase for catalyzing a conversion of the phosphorylated saccharide into an isomer of the phosphorylated saccharide;

f) expressing one or more polynucleotides in the *Saccharomyces* microorganism for catalyzing a conversion of the isomer into an organic molecule, wherein the organic molecule is isopropanol; and g) contacting the oligosaccharide source with the *Saccharomyces* microorganism.

10. The method of claim 1, wherein the phosphorylase is sucP of *Leuconostoc mesenteroides.*

11. The method of claim 8, wherein the phosphorylase is sucP of *Leuconostoc mesenteroides.*

12. The method of claim 9, wherein the phosphorylase is sucP of *Leuconostoc mesenteroides.*

13. The method of claim 1, wherein the oligosaccharide transporter, phosphorylase, and phosphoglucomutase are expressed using a constitutive strong promoter.

* * * * *